(12) United States Patent
Fong et al.

(10) Patent No.: US 8,124,082 B2
(45) Date of Patent: Feb. 28, 2012

(54) HUMANIZED ANTI-BETA7 ANTAGONISTS AND USES THEREFOR

(75) Inventors: Sherman Fong, Alameda, CA (US); Mark S. Dennis, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 119 days.

(21) Appl. No.: 12/390,730

(22) Filed: Feb. 23, 2009

(65) Prior Publication Data

US 2009/0226437 A1    Sep. 10, 2009

Related U.S. Application Data

(62) Division of application No. 11/219,121, filed on Sep. 2, 2005, now Pat. No. 7,528,236.

(60) Provisional application No. 60/607,377, filed on Sep. 3, 2004.

(51) Int. Cl.
*A61K 39/395* (2006.01)

(52) U.S. Cl. ............... 424/133.1; 424/141.1; 424/143.1; 424/152.1; 424/156.1; 424/174.1

(58) Field of Classification Search ................. None
See application file for complete search history.

(56) References Cited

U.S. PATENT DOCUMENTS

| | | | |
|---|---|---|---|
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,563,304 A | 1/1986 | Carlsson et al. |
| 4,816,567 A | 3/1989 | Cabilly et al. |
| 4,970,198 A | 11/1990 | Lee et al. |
| 4,975,278 A | 12/1990 | Senter et al. |
| 5,053,394 A | 10/1991 | Ellestad et al. |
| 5,079,233 A | 1/1992 | Lee et al. |
| 5,208,020 A | 5/1993 | Chari et al. |
| 5,416,064 A | 5/1995 | Chari et al. |
| 5,580,717 A | 12/1996 | Dower et al. |
| 5,585,089 A | 12/1996 | Queen et al. |
| 5,606,040 A | 2/1997 | McGahren et al. |
| 5,624,821 A | 4/1997 | Winter et al. |
| 5,648,260 A | 7/1997 | Winter et al. |
| 5,658,727 A | 8/1997 | Barbas et al. |
| 5,693,762 A | 12/1997 | Queen et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,733,743 A | 3/1998 | Johnson et al. |
| 5,739,116 A | 4/1998 | Hamann et al. |
| 5,750,373 A | 5/1998 | Garrard et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,837,242 A | 11/1998 | Holliger et al. |
| 5,877,296 A | 3/1999 | Hamann et al. |
| 5,969,108 A | 10/1999 | McCafferty et al. |
| 6,172,197 B1 | 1/2001 | McCafferty et al. |
| 6,300,080 B1 | 10/2001 | Brenner et al. |
| 6,551,593 B1 | 4/2003 | Ringler et al. |
| 7,528,236 B2 | 5/2009 | Fong et al. |
| 7,687,605 B2 | 3/2010 | Fong et al. |
| 2001/0046496 A1 | 11/2001 | Brettman et al. |
| 2005/0095238 A1 | 5/2005 | Brettman et al. |

FOREIGN PATENT DOCUMENTS

| | | |
|---|---|---|
| EP | 0425235 B1 | 9/1996 |
| EP | 1391213 A1 | 2/2004 |
| EP | 1133315 B1 | 2/2006 |
| WO | WO93/06213 | 4/1993 |
| WO | WO 93/21232 | 10/1993 |
| WO | WO 94/11026 | 5/1994 |
| WO | WO 94/29351 | 12/1994 |
| WO | WO 96/24673 | 8/1996 |
| WO | WO 98/06248 | 2/1998 |
| WO | WO 99/51642 | 10/1999 |
| WO | WO 00/30681 | 6/2000 |
| WO | 00/40604 | 7/2000 |
| WO | WO01/78779 | 10/2001 |
| WO | 2005/080432 A2 | 9/2005 |

OTHER PUBLICATIONS

Chen, et al., *Journal of Molecular Biology*—293:865-881 (1999).
Clark (Protein Engineering of Antibody Molecules for Prophylactic and Therapeutic Applications in an, 1993, pp. 4-5).
Holm, et al., *Molecular Immunology*—44:1075-1084 (2007).
Malmborg, et al., *Journal of Immunological Methods*—183:7-13 (1995).
Pascalis, et al., *Journal of Immunology*—169:3076-3084 (2002).
Wu, et al., *Journal of Molecular Biology*—294:151-162 (1999).
Vajdos, et al., *Journal of Molecular Biology*—320:415-428 (2002).
Andrew, D.P. et al., "Distinct but overlapping epitopes are involved in $\alpha_4\beta_7$-mediated adhesion to vascular cell adhesion molecule-1, mucosal addressin-1, fibronectin, and lymphocyte aggregation" *J. Immunol.* 153:3847-3861 (1994).
Baldwin et al., "Monoclonal Antibodies In Cancer Treatment" *Lancet, The* pp. 603-605 (Mar. 15, 1986).
Barbadillo, C. et al., "Anti-integrin immunotherapy in rheumatoid arthritis: protective effect of anti-$\alpha$4 antibody in adjuvant arthritis" *Springer Semin. Immunopathol.* 16:427-436 (1995).

(Continued)

*Primary Examiner* — Karen Canella
(74) *Attorney, Agent, or Firm* — Jennifer L. Davis

(57) ABSTRACT

The invention provides therapeutic anti-beta7 antibodies, compositions comprising, and methods of using these antibodies.

14 Claims, 22 Drawing Sheets

OTHER PUBLICATIONS

Barbas III et al., "In Vitro Evolution of a Neutralizing Human Antibody to Human Immunodeficiency Virus Type 1 to Enhance Affinity and Broaden Strain Cross-Reactivity" *Proc. Natl. Acad. Sci. USA* 91(9):3809-3813 (Apr. 1994).

Carlsson, J. et al., "Protein Thiolation and Reversible Protein-Protein Conjugation" *Biochemical Journal* 173:723-737 (1978).

Carter et al., "Humanization of an Anti-p185$^{HER2}$ Antibody for Human Cancer Therapy" *Proc. Natl. Acad. Sci. USA* 89(10):4285-4289 (May 1992).

Cepek, K.L. et al., "Integran $\alpha^E\beta_7$ mediates adhesion of T lymphocytes to epithelial cells" *J. Immunol*, 150:3459-3470 (1993).

Chari et al., "Immunoconjugates Containing Novel Maytansinoids: Promising Anticancer Drugs" *Cancer Research* 52:127-131 (Jan. 1992).

Chothia, et al., "Canonical Structures for the Hypervariable Regions of Immunoglobulins" *J. Mol. Biol.* 196:901-917 (1987).

Cunningham and Wells, "High-Resolution Epitope Mapping of hGH-Receptor Interactions by Alanine-Scanning Mutagenesis" *Science* 244:1081-1085 (Jun. 2, 1989).

Doronina et al., "Development of potent monoclonal antibody auristatin conjugates for cancer therapy" *Nature Biotechnology* 21:778-784 (2003).

Duncan and Winter, "The binding site or C1q on IgG" *Nature* 322:738-740 1988.

Ebert, M. et al., "CD8+CD103+ T cells analogous to intestinal intraepithelial lymphocytes infiltrate the pancreas in chronic pancreatitis" *Am. J. Gastroenterol*, 93:2141-2147 (1998).

Erle et al., "Complete amino acid sequence of an integrin β subunit ($\beta_7$) identified in leukocytes" *Journal of Biological Chemistry* 266(17):11009-11016 (Jun. 15, 1991).

Fraker and Speck Jr., "Protein and cell membrane iodinations with a sparingly soluble chloroamide, 1,3,4,6-tetrachloro-3a,6a-diphenylglycoluril" *Biochemical & Biophysical Research Communications* 80(4):849-857 (1978).

Francisco et al., "cAC10-vcMMAE, an anti- CD30 monomethyl auristatin E conjugate with potent and selective antitumor activity" *Blood* 102:1458-1465 (2003).

Gallop et al., "Applications of Combinatorial Technologies to Drug Discovery Background and peptide combinatorial libraries" *Journal of Medicinal Chemistry* 37(9):1233-1251 (Apr. 29, 1994).

"Gemtuzumab Ozogamicin" *Drugs of The Future* 25(7):686-692 (2000).

Grant, A.J. et al., "MadCAM-1 expressed in chronic inflammatory liver disease supports mucosal lymphocyte adhesion to hepatic endothelium (MAdCAM-1 in chronic inflammatory liver disease)" *Hepatology* 33(5):1065-1072 (2001).

Gurish et al., "Expression of murine $\beta_7$, $\alpha_4$, and $\alpha_1$ integrin genes by rodent mast cells" *Journal of Immunology* 149(6):1964-1972 (Sep. 15, 1992).

Hadley et al., "CD103+ CTL accumulate within the graft epithelium during clinical renal allograft rejection" *Transplantation* 72 (9) :1548-1555 (2001).

Hakimi et al., "Reduced immunogenicity and improved pharmacokinetics of humanized anti-Tac in cynomolgus monkeys" *J Immunol.* 147(4):1352-1359 (Aug. 15, 1991).

Harris, "Production of humanized monoclonal antibodies or in vivo imaging and therapy" *Biochemical Society Transactions* 23:1035-1038 (1995).

Hawkins et al., "Selection of Phage Antibodies by Binding Affinity Mimicking Affinity Maturation" *J. Mol. Biol.* 226:889-896 (1992).

Hillan, K. et al., "Expression of the mucosal vascular addressan, MAdCAM-1, in inflammatory liver disease" *Liver* 19(6):509-518 (1999).

Hinman et al., "Preparation and Characterization of Monoclonal Antibody conjugates of the Calicheamicins: A Novel and Potent Family of Antitumor Antibiotics" *Cancer Research* 53:3336-3342 (Jul. 15, 1993).

Hurle and Gross, "Protein Engineering Techniques for Antibody Humanization" *Curr. Op. Biotech.* 5:428-433 (1994).

Jackson et al., "In vitro antibody maturation: Improvement of a high affinity, neutralizing antibody against IL-1 beta" *J. Immunol.* 154(7):3310-3319 (1995).

Jaffers et al., "Monoclonal Antibody Therapy, Anti-Idiotypic and Non-Anti-Idiotypic Antibodies to OKT3 Arising Despite Intense Immunosuppression" *Transplantation* 41(5):572-578 (May 1986).

Jones et al., "Replacing the Complementarity-Determining Regions in a Human Antibody with Those From a Mouse" *Nature* 321:522-525 (May 29, 1986).

Junghans et al., "Anti-Tac-H, a Humanized Antibody to the Interleukin 2 Receptor with New Features for Immunotherapy in Malignant and Immune Disorders" *Cancer Research* 50(5):1495-1502 (Mar. 1, 1990).

Kanwar, J. et al., "$\beta7$ integrins contribute to demyelinating disease of the central nervous system" *J. Neuroimmunology* 103:146-152 (2000).

Khazaeli et al., "Phase I trial of multiple large doses of murine monoclonal antibody C017-1A. II. Pharmacokinetics and immune response" *J Natl Cancer Inst.*80(12):937-942 (Aug. 17, 1988).

Kilger and Holzmann, "Molecular analysis of the physiological and pathophysiological role of $\alpha_4$-integrins" *Journal of Molecular Medicine* 73(7):347-354 (Jul. 1995).

Kilshaw and Murant, "Expression and regulation of $\beta_7$($\beta$p) integrins on mouse lymphocytes: relevance to the mucosal immune system" *European Journal of Immunology* 21(10):2591-2597 (Oct. 1991).

Kroneld, U. et al., "Expression of the mucosal lymphocyte integrin $\beta$sup$E\beta_7$ and its Ligand E-cadherin in salivary glands of patietns with Sjogren's syndrome" *Scand J Rheumatol* 27:215-218 (1998).

Kunkel et al., "Rapid and Efficient Site-specific Mutagenesis Without Phenotypic Selection" *Methods in Enzymology* 154:367-382 (1987).

Laberge, S. et al., "Role of VLA-4 and LFA-1 in Allergen-Induced Airway Hyperrespnosiveness and Lung Inflammation in the Rat" *Am. J. Respir. Crit. Care Med.* 151:822-829 (1995).

Leckie et al., "Sputum T lymphocytes in asthma, COPD and healthy subjects have the phenotype of activated intraepithelial T cells (CD69+ CD103+)" *Thorax* 58:23-20 (2003).

Lee et al., "High-affinity human antibodies from phage-displayed synthetic Fab libraries with a single framework scaffold" *J Mol Biol.* 340(5):1073-1093 (Jul. 23, 2004).

Liu et al., "Eradication of Large Colon Tumor Xenografts by Targeted Delivery of Maytansinolds." *Proc. Natl. Acad. Sci. USA* 93:8618-8623 (1996).

Lode et al., "Targeted Therapy with a Novel Enediyene Antibiotic Calicheamicin 0 I1 Effectively Suppresses Growth and Dissemination of Liver Metastases in a Syngeneic Model of Murine Neuroblastoma" *Cancer Research* 58:2925-2928 (Jul. 15, 1998).

Ludviksson, B. et al., "Administration of mAb against $\alpha^E\beta_7$ prevents and ameliorates immunization-induced colitis in IL-2-/- mice" *J. Immunol.* 162:4975-4982 (1999).

MacCallum, R. M. et al., "Antibody-antigen interactions: contact analysis and binding site topography" *J. Mol. Biol.* 262:732-745 (1996).

Mandler et al., "Modifications in synthesis strategy improve the yield and efficacy of geldanamycin—herceptin immunoconjugates" *Bioconjugate Chem.* 13:786-791 (2002).

Mandler, Raya, et al., "Immunoconjugates of Geldanamycin and Anti-HER2 Monoclonal Antibodies: Antiproliferative Activity on Human Breast Carcinoma Cell Lines" *Journal of the National Cancer Institute* 92(19):1573-1581 (Oct. 4, 2000).

Mandler, Raya, et al., "Synthesis and Evaluation of Antiproliferative Activity of a Geldanamycin-Herceptin(tm) Immunoconjugate" *Bioorganic & Medicinal Chemistry Letters* 10:1025-1028 (2000).

Marks et al., "By-Passing Immunization: Building High Affinity Human Antibodies by Chain Shuffling" *Bio/Technology* 10:779-783 (Jul. 1992).

Meresse, B. et al., "CD28+ intraepithelial lymphocytes with Long Telomeres are recruited within the inflamed Ileal Mucosa in Crohn Disease" *Human Immunol.* 62:694-700 (2001).

Miller, R. et al., "Monoclonal antibody therapeutic trials in seven patients with T-cell lymphoma" *Blood* 62:988-995 (1983).

Niculescu-Duvaz and Springer, "Antibody-Directed Enzyme prodrug Therapy (ADEPT): A Review" *Adv. Drg. Del. Rev.* 26:151-172 (1997).

Oshitani, N. et al., "Differential expression of homing receptor CD103 on lamina propria lymphocytes and association of CD103 with epithelial adhesion molecules in inflammatory bowel disease" *International J Molecule Med.* 12:715-719 (2003).

Pang, M. et al., "Up-regulation of αEβ7, a novel integrin adhesion molecule, on T cells from systemic lupus erythematosus patients with specific epithelial involvement" *Arthritis and Rheumatism* 41:1456-1463 (1998).

Picarella et al., "Monoclonal antibodies specific for β7 integrin and mucosal addressin cell adhesion molecule-1 (MAdCAM-I) reduce inflammation in the colon of scid mice reconstituted with CD45RB$^{high}$ CD4$^+$ T cells" *Journal of Immunology* 158(5):2099-2106 (Mar. 1, 1997).

Podolsky, D.K., "Inflammatory Bowel Disease" *New England J. of Medicine* 325:928-937 (1991).

Powrie and Leach, "Genetic and Spontaneous Models of Inflammatory Bowel Disease in rodents: Evidence for Abnormalities in Mucosal Immune Regulation" *Ther. Immunol.* 2:115-123 (1995).

Presta et al., "Humanization of an Anti-Vascular Endothelial Growth Factor Monoclonal Antibody for the Therapy of Solid Tumors and Other Disorders" *Cancer Research* 57(20):4593-4599 (Oct. 15, 1997).

Presta, et al., "Humanization of an Antibody Directed Against IgE" *Journal of Immunology* 151(5):2623-2632 (Sep. 1993).

Presta, Leonard G., "Antibody Engineering" *Current Opinion in Structure Biology* 2:593-596 (1992).

Reichmann, L. et al., "Reshaping human antibodies for therapy" *Nature* 332:323-337 (1988).

Rowland et al., "Drug Localisation and Growth Inhibition Studies of Vindesine-Monoclonal anti-CEA Conjugates in a Human Tumour Xenograft" *Cancer Immunol. Immunother.* 21:183-187 (1986).

Schier et al., "Identification of functional and structural amino-acid residues by parsimonious mutagenesis" *Gene* 169:147-155 (1996).

Sears et al., "Effects of monoclonal antibody immunotherapy on patients with gastrointestinal adenocarcinoma" *J Biol Response Mod.* 3(2):138-150 (1984).

Shaw, S.K. and Brenner, M.B., "The β7 integrins in mucosal homing and retention" *Semin. Immunol.* 7335-342 (1995).

Shawler, D. L. et al., "Human immune response to multiple injections of murine monoclonal IgG$^1$" *J. Immunol.* 135(2):1530-1535 (1985).

Shimizu, Y. et al., "Preferential accumulation of CD103+ T cells in human livers; its association with extrathymic T cells" *J Hepatology* 39:918-924 (2003).

Sims et al., "A Humanized CD18 Antibody Can Block Function without Cell Destruction" *Journal of Immunology* 151 (4) :2296-2308 (Aug. 1993).

Souza, H. et al., "Expression of lymphocyte-endothelial receptor-ligand pairs, α4β7/MAdCAM-1 and OX40/OX40 ligand in the colon and jejunum of patients with inflammatory bowel disease" *Gut* 45:856-863 (1999).

Sun, X. et al., "β7 integrins contribute to skin graft rejection" *Transplantation* 74:1202-1203 (2002).

Syrigos, K. N. et al., "Antibody Directed Enzyme Prodrug Therapy (ADEPT): A Review of the Experimental and Clinical Considerations" *Anticancer Research* 19:605-614 (1999).

Teraki and Shiohara, "Preferential expression of αEβ7 integrin (CD103) on CD8+T cells in the psoriatic epidermis: regulation by interleukins 4 and 12 and transforming growth factor-β" *Br J Dermatology* 147:1118-1126 (2002).

Thorpe, P.E., "Antibody Carriers of Cytotoxic Agents in Cancer Therapy: A Review" *Monoclonal Antibodies 84: Biological and Clinical Applications*, A. Pinchera, G. Doria, F. Dammacco & Bargellesi, Editrice Kurtis s.r.l. pp. 475-506 (1985).

Tidswell, M. et al., "Structure-function analysis of the integrin β7 subunit. Identification of domains involved in adhesion to MadCAM-1$^{1,2}$" *J. Immunol.* 169:1497-1505 (1997).

Vaswani and Hamilton, "Humanized antibodies as potential therapeutic drugs" *Ann. Allergy, Asthma & Immunol.* 1:105-115 (1998).

Verhoeyen et al., "Reshaping Human Antibodies: Grafting an Antilysozyme Activity" *Science* 239:1534-1536 (Mar. 25, 1988).

Viney et al., "Mucosal addressin cell adhesion molecule-1: a structural functional analysis demarcates the integrin binding motif" *Journal of Immunology* 157(6):2488-2497 (Sep. 15, 1996).

Vitetta et al., "Redesigning Nature's Poisons to Create Anti-Tumor Reagents" *Science* 238:1098-1104 (1987).

Wiseman et al, "Ibritumomab tiuxetan radioimmunotherapy for patients with relapsed or refractory non-Hodgkin lymphoma and mild thrombocytopenia: a phase II multicenter trial" *Blood* 99(12):4336-4342 (Jun. 15, 2002).

Wiseman, G.A. et al., "Phase I/II $^{90}$Y-Zevalin (yttrium-90 ibritumomab tiuxetan, IDEC-Y2B8) radioimmunotherapy dosimetry results in relapsed or refractory non-Hodgkin's lymphoma" *European Nuclear Med.* 27(7):766-777 (2000).

Witzig, Thomas E. et al, "Randomized Controlled Trial of Yttrium-90—Labeled Ibritumomab Tiuxetan Radioimmunotherapy Versus Rituximab Immunotherapy for Patients With Relapsed or Refractory Low-Grade, Follicular, or Transformed B-Cell Non-Hodgkin's Lymphoma" *Journal of Clinical Oncology* 20(10):2453-2463.

Witzig, Thomas E. et al, "Treatment With Ibritumomab Tiuxetan Radioimmunotherapy in Patients With Rituximab-Refractory Follicular Non-Hodgkin's Lymphoma" *Journal of Clinical Oncology* 20(15):3262-3269 (Aug. 1, 2002).

Yelton et al., "Affinity Maturation of the BR96 Anti-Carcinoma Antibody by Codon-Based Mutagenesis" *The Journal of Immunology* 155:1994-2004 (1995).

Yoshitake et al., "Conjugation of glucose oxidase from *Aspergillus niger* and rabbit antibodies using N-hydroxysuccinimide ester of N-(4-carboxycyclohexylmethyl)-maleimide" *European Journal of Biochemistry* 101:395-399 (1979).

Zoller et al., "Oligonucleotide-Directed Mutagenesis Using M13-Derived Vectors: An Efficient and General Procedure for the Production of Point Mutations in Any Fragment of DNA" *Nucleic Acids Research* 10:6487-6504 (1987).

Database Biosis, "Methods in Molecular Biology" *Biosciences Information Service* (Database accession No. PREV200600158659) (2004).

Hanes et al., "Picomolar affinity antibodies from a fully synthetic naive library selected and evolved by ribosome display" *Nature Biotechnolgoy* 18:1287-1292 (Dec. 2000).

Kabat et al. *Sequences of Proteins of Immunological Interest* (Table of Contents, Introduction and Constant Region Sequences sections), 5th edition, Bethesda, MD:NIH vol. 1:iii-xcvi and 647-723 (1991).

Radar et al. "A phage display approach for rapid antibody humanization: Designed combinatorial V gene libraries" *Proc. Natl. Acad. Sci. USA* 95:8910-8915 (Jul. 1998).

Toran et al., "Improvement in affinity and HIV-1 neutralization by somati mutation in the heavy chain first complementarity-determining region of antibodies triggered by HIV-1 infection" *European Journal of Immunology* 31:128-137 (Jan. 2001).

Wu et al., "Stepwise in vitro affinity maturation of Vitaxin, an α$_v$β$_3$-specific humanized mAb" *Proc. Natl. Acad. Sci. USA* 95(11):6037-6042 (May 26, 1998).

Yang et al., "CDR walking mutagenesis for the affinity maturation of a potent human anti-HIV-1 antibody into the picomolar range" *Journal of Molecular Biology* 254(3):392-403 (Dec. 1, 1995).

Boerner et al., "Production of Antigen-Specific Human Monoclonal Antibodies From In Vitro-Primed Human Splenocytes" *J Immunol.* 147(1):86-95 (Jul. 1991).

Briskin et al., "MAdCAM-1 has homology to immunoglobulin and mucin-like adhesion receptors and to IgA1" *Nature* 363(6428):461-464 (Jun. 3, 1993).

Bruggermann et al., "Designer Mice: The Production of Human Antibody Repertoires in Transgenic Animals" *Generation of Antibodies by Cell and Gene Immortalization: The Year in Immunology* 7:33-40 (1993).

Butcher et al., "Lymphocyte Homing and Homeostasis" *Science* 272:60-66 (1996).

Butcher et al., "Lymphocyte trafficking and regional immunity" *Adv. Immunol.* 72:209-253 (1999).

Chuluyan et al., "α4-Integrin-dependent emigration of monocytes" *Springer Semin. Immunopathology* 16:391-404 (1995).

Elices et al., "VCAM-1 on activated endothelium interacts with the leukocyte integrin VLA-4 at a site distinct from the VLA-4/fibronectin binding site" *Cell* 60:577-584 (1990).

Hemler, "VLA proteins in the integrin family: structures, functions, and their role on leukocytes" *Annu. Rev. Immunol.* 8:365-400 (1990).

Hesterberg et al., "Rapid resolution of chronic colitis in the cottontop tamarin with an antibody to a gut-homing integrin α4β7" *Gastroenterology* 111(5):1373-1380 (Nov. 1996).

Holzmann et al., "Identification of a Murine Peyer's Patch-specific lymphocyte homing receptor as an integrin molecule with an α chain homologous to human VLA-4α" *Cell* 56:37-46 (1989).

Hoogenboom et al., "Multi-subunit proteins on the surface of filamentous phage: methodologies for displaying antibody (Fab) heavy and light chains" *Nucleic Acids Research* 19(15):4133-4137 (1991).

Hu et al., "Cloning and expression of mouse integrin $\beta_p(\beta_7)$: A functional role in Peyer's patch-specific lymphocyte homing" *Proc. Natl. Acad. Sci. USA* 89:8254-8258 (Sep. 1992).

Hynes, "Integrins: versatility, modulation, and signaling in cell adhesion" *Cell* 69(1):11-25 (1992).

Ishikawa et al., "Interleukin-6, CD45 and the Src-kinases in myeloma cell proliferation" *Leuk. Lymphoma* 44(9):1477-1481 (2003).

Makarem et al., "Competitive binding of vascular cell adhesion molecule-1 and the HepII/IIICS domain of fibronectin to the integrin α4β1" *Journal of Biological Chemistry* 269:4005-4011 (1994).

Marks et al., "By-Passing Immunization: Human Antibodies From V-gene Libraries Displayed on Phage" *J Mol Biol.* 222(3):581-597 (Dec. 5, 1991).

Meenan et al., "Altered expression of $\beta_4\beta_7$, a gut homing integrin, by circulating and mucosal T cells in colonic mucosal inflammation" *Gut* 40:241-246 (1997).

Nakajima et al., "Role of vascular cell adhesion molecule 1/very late activation antigen 4 and intercellular adhesion molecule 1/lymphocyte function-associated antigen 1 interactions in antigen-induced eosinophil and T cell recruitment into the tissue" *J Exp. Med.* 179:1145-1154 (1994).

Rabasseda et al., "Gemtuzumab Ozogamicin" *Drugs of the Future* 25(7):686-692 (2000).

Rose et al., "Expression of the mucosal homing receptor $\alpha_4\beta_7$ correlates with the ability of CD8+ memory T cells to clear rotavirus infection" *Journal of Virology* 72(1):726-730 (Jan. 1998).

Rott et al., "A fundamental subdivision of circulating lymphocytes defined by adhesion to mucosal addressin cell adhesion molecule-1. Comparison with vascular cell adhesion molecule-1 and correlation with β7 integrins and memory differentiation." *J. Immunol.* 156:3727-3736 (1996).

Rott et al., "Expression of mucosal homing receptor $\alpha_4\beta_7$ by circulating CD4+ cells with memory for intestinal rotavirus." *J. Clin. Invest.* 100(5):1204-1208 (Sep. 1997).

Shyjan et al., "Human mucosal addressin cell adhesion molecule-1 (MAdCAM-1) demonstrates structural and functional similarities to the $\alpha_4\beta_7$-integrin binding domains of murine MAdCAM-1, but extreme divergence of mucin-like sequences" *Journal of Immunology* 156(8):2851-2857 (Apr. 15, 1996).

Stanton et al., "CD45 variant alleles: possibly increased frequency os a novel exon 4 CD45 polymorphism in HIV seropositive Ugandans" *Immunegenetics* 56(2):107-110 (2004).

Tchilian and Beverly, "CD45 in memory and disease" *Arch. Immunol. Ther. Exp.* 50(2):85-93 (2002).

Williams and Butcher, "Homing of naive and memory T lymphocyte subsets to Peyer's patches, lymph nodes, and spleen" *J. Immunol.* 159:1746-1752 (1997).

Williams et al., "The memory B cell subset responsible for the secretory IgA response and protective humoral immunity to rotavirus expresses the intestinal homing receptor, $\alpha_4\beta_7$" *J. Immunol.* 161:4227-4235 (1998).

"Extended European Search Report mailed Mar. 25, 2011 in European Application No. 10177407.3".

Rudikoff et al., "Single amino acid substitution altering antigen-binding specificity" *Proc. Natl. Acad. Sci. USA* 79:1979-1983 (Mar. 1982).

Foote et al., "Antibody Framework Residues Affecting the Conformation of the Hypervariable Loops" *J. Mol. Biol.* 224:487-499 (1992).

Winter et al., "Humanized antibodies" *Immunology Today* 14(6):243-246 (1993).

FIG. 1A, FIG. 1B: Sequence alignment of huKI, Fib504, 504K graft, hu504-5, hu504-16, hu504-32 (variable light chain) and humIII, Fib504, 504K graft (variable heavy chain). SEQ ID NOs: 23, 10, 25, 24, 11, 26.

FIG. 1C

Humanized Variants of Fib504

HVR-L1 and L2 substitutions,
Fib504•K RF framework

| Variant | L1: R A S E S V D T L H | L2: K Y A S Q S I S | BIAcore Affinity Assay (nM) |
|---|---|---|---|
| 504K-RF residues | R A S E S V D T L H | K Y A S Q S I S | |
| 68 | R A S E S V D T L H | K Y A S Q S I S | |
| 74 | R A S E S V D T L H | K Y A S Q S I S | 11 |
| 504-32 | | | |
| 51 | R A S E S V D T L H | K Y A S Q S I S | |
| 59 | R A S E S V D T L H | K Y A S Q S I S | 3.5 |
| 504-5 | | | |
| 60 | R A S E S V D T L H | K Y A S Q R I S | |
| 96 | R A S E S V D T L H | K Y A S Q S I S | |
| 83 | R A S S E S V D T L H | K Y A S Q S I S | 9 |
| 504-16 (8) | R A S E S V D T L H | K Y A S Q S I S | 23.4 |
| 504-RF (29) | R A S E S V D T Y L H | K Y A S Q S I S | 132 |

Human Consensus

FIG. 2A

Light chain (kappa I)

DIQMTQSPSSLSASVGDRVTITC<u>RASQSISNYLA</u>WYQQKPGKAPKLLI<u>YAASSLES</u>
GVPSRFSGSGSGTDFTLTISSLQPEDFATYYC<u>QQYNSLPWT</u>FGQGTKVEIKRTVA
APSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC (SEQ ID
NO:27)

FIG. 2B

Heavy chain (subgroup III)

EVQLVESGGGLVQPGGSLRLSCAAS<u>GFTFSSYAMS</u>WVRQAPGKGLEWV<u>SVISGD</u>
<u>GGSTYYADSVKG</u>RFTISRDNSKNTLYLQMNSLRAEDTAVYYCA<u>MTGSSGYFDF</u>
WGQGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMHEAL
HNHYTQKSLSLSPGK (SEQ ID NO:28)

Fib504 graft

FIG. 3A

Light chain

DIQMTQSPSSLSASVGDRVTITC<u>RASESVDTYLH</u>WYQQKPGKAPKLLIY<u>YASQSIS</u>
GVPSRFSGSGSGTDFTLTISSLQPEDFATYYC<u>QQGNSLPNT</u>FGQGTKVEIKRTVAA
PSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC (SEQ ID
NO:29)

FIG 3B

Heavy chain

EVQLVESGGGLVQPGGSLRLSCAAS<u>GFFITNNYW</u>GWVRQAPGKGLEWV<u>GYISY
SGSTSYNPSLKS</u>RFTISADTSKNTAYLQMNSLRAEDTAVYYCA<u>MTGSSGYFDFW</u>
GQGTLVTVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALH
NHYTQKSLSLSPGK (SEQ ID NO:30)

Fib504K graft

FIG. 4A

Light chain

DIQMTQSPSSLSASVGDRVTITC<u>RASESVDTYLH</u>WYQQKPGKAPKLLI<u>KYASQSIS</u>
GVPSRFSGSGSGTDFTLTISSLQPEDFATYYC<u>QQGNSLPNT</u>FGQGTKVEIKRTVAA
PSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC (SEQ ID NO:31)

FIG. 4B

Heavy chain

EVQLVESGGGLVQPGGSLRLSCAAS<u>GFFITNNYWG</u>WVRQAPGKGLEWVG<u>YISY
SGSTSYNPSLKS</u>RFTISADTSKNTAYLQMNSLRAEDTAVYYCA<u>MTGSSGYFDF</u>W
GQGTLVTVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALH
NHYTQKSLSLSPGK (SEQ ID NO:30)

Fib504K-RF graft

FIG. 5A

Light chain

DIQMTQSPSSLSASVGDRVTITC<u>RASESVDTYLH</u>WYQQKPGKAPKLL<u>IKYASQSIS</u>GVPSRFSGSGSGTDFTLTISSLQPEDFATYYC<u>QQGNSLPNT</u>FGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:31)

FIG. 5B

Heavy chain

EVQLVESGGGLVQPGGSLRLSCAAS<u>GFFITNNYW</u>GWVRQAPGKGLEWVG<u>YISYSGSTSYNPSLKS</u>RFTISRDTSKNTFYLQMNSLRAEDTAVYYCA<u>MTGSSGYFDF</u>WGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO:32)

Humanized variant 504.32

FIG. 6A

Light chain

DIQMTQSPSSLSASVGDRVTITC<u>RASESVDDLLH</u>WYQQKPGKAPKLLI<u>KYASQSIS</u>
GVPSRFSGSGSGTDFTLTISSLQPEDFATYYC<u>QQGNSLPNT</u>FGQGTKVEIKRTVAA
PSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC (SEQ ID
NO:33)

FIG. 6B

Heavy chain

EVQLVESGGGLVQPGGSLRLSCAAS<u>GFFITNNYWG</u>WVRQAPGKGLEWVG<u>YISY
SGSTSYNPSLKS</u>RFTISRDTSKNTFYLQMNSLRAEDTAVYYCA<u>MTGSSGYFDF</u>W
GQGTLVTVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALH
NHYTQKSLSLSPGK (SEQ ID NO:32)

```
κV1   ZDIQMTQSPSSLSASVGDRVTITC[   ]WYQQKPGKAPKLLIY[L2]GVPSRFSGSGSGTDFTLTISSLQP
κV1X  DIQMTQSPSSLSASVGDRVTITC[   ]WYQQKPGKAPKLLI [L2]GVPSRFSGSGSGTDFTLTISSLQP
κV2   DIVMTQSPLSLPVTPGEPASISC[   ]WYLQKPGQSPQLLIY[L2]GVPDRFSGSGSGTDFTLKISRVEA
κV3   EIVLTQSPGTLSLSPGERATLSC[   ]WYQQKPGQAPRLLIY[L2]GIPDRFSGSGSGTDFTLTISRLEP
κV4   DIVMTQSPDSLAVSLGERATINC[   ]WYQQKPGQPPKLLIY[L2]GVPDRFSGSGSGTDFTLTISSLQA
```

FIG. 7A

E D F A T Y Y C [CDR-L3] F G Q G T K V E I K    SEQ ID NO 14

E D F A T Y Y C [CDR-L3] F G Q G T K V E I K    SEQ ID NO 15

E D V G V Y Y C [CDR-L3] F G Q G T K V E I K    SEQ ID NO 16

E D F A V Y Y C [CDR-L3] F G Q G T K V E I K    SEQ ID NO 17

E D V A V Y Y C [CDR-L3] F G Q G T K V E I K    SEQ ID NO 18

FIG. 7B

| | | | | | |
|---|---|---|---|---|---|
| I | | | | | |
| A | QVQLVQSGAEVKKPGASVKVSCKAS | GYTFT | [CDR1] | WVRQAPGQGLEWMG | [CDR2] |
| B | QVQLVQSGAEVKKPGASVKVSCKAS | | | WVRQAPGQGLEWM | |
| C | QVQLVQSGAEVKKPGASVKVSCKAS | | | WVRQAPGQGLEWM | |
| D | QVQLVQSGAEVKKPGASVKVSCKAS | | | WVRQAPGQGLEWM | |
| II | | | | | |
| A | QVQLQESGPGLVKPSQTLSLTCTVS | GGSVS | | WIRQPPGKGLEWIG | |
| B | QVQLQESGPGLVKPSQTLSLTCTVS | | | WIRQPPGKGLEWI | |
| C | QVQLQESGPGLVKPSQTLSLTCTVS | | | WIRQPPGKGLEWI | |
| D | QVQLQESGPGLVKPSQTLSLTCTVS | | | WIRQPPGKGLEWI | |
| III | | | | | |
| A | EVQLVESGGGLVQPGGSLRLSCAAS | GFTFS | | WVRQAPGKGLEWVS | |
| B | EVQLVESGGGLVQPGGSLRLSCAAS | | | WVRQAPGKGLEWV | |
| C | EVQLVESGGGLVQPGGSLRLSCAAS | | | WVRQAPGKGLEWV | |
| D | EVQLVESGGGLVQPGGSLRLSCAAS | | | WVRQAPGKGLEWV | |
| Acceptor | | | | | |
| A | EVQLVESGGGLVQPGGSLRLSCAAS | GFNIK | | WVRQAPGKGLEWVS | |
| B | EVQLVESGGGLVQPGGSLRLSCAAS | | | WVRQAPGKGLEWV | |
| C | EVQLVESGGGLVQPGGSLRLSCAAS | | | WVRQAPGKGLEWV | |
| Second Acceptor | | | | | |
| A | EVQLVESGGGLVQPGGSLRLSCAAS | GFNIK | | WVRQAPGKGLEWVS | |
| B | EVQLVESGGGLVQPGGSLRLSCAAS | | | WVRQAPGKGLEWV | |
| C | EVQLVESGGGLVQPGGSLRLSCAAS | | | WVRQAPGKGLEWV | |
| D | EVQLVESGGGLVQPGGSLRLSCAAS | | | WVRQAPGKGLEWV | |

FIG. 8A

| | | | | | | | | | | | | | | | | | | | | |
|---|---|---|---|---|---|---|---|---|---|---|---|---|---|---|---|---|---|---|---|---|
| R V T I T A D T S T S T A Y M E L S S L R S E D T A V Y Y C A R | ... | W G Q G T L V T V S S | SEQ ID NO:19 |
| R V T I T A D T S T S T A Y M E L S S L R S E D T A V Y Y C A R | ... | W G Q G T L V T V S S | SEQ ID NO:20 |
| R V T I T A D T S T S T A Y M E L S S L R S E D T A V Y Y C A R | ... | W G Q G T L V T V S S | SEQ ID NO:21 |
| R V T I T A D T S T S T A Y M E L S S L R S E D T A V Y Y C | ... | W G Q G T L V T V S S | SEQ ID NO:22 |
| R V T I S V D T S K N Q F S L K L S S V T A A D T A V Y Y C A R | ... | W G Q G T L V T V S S | SEQ ID NO:48 |
| R V T I S V D T S K N Q F S L K L S S V T A A D T A V Y Y C A R | ... | W G Q G T L V T V S S | SEQ ID NO:49 |
| R V T I S V D T S K N Q F S L K L S S V T A A D T A V Y Y C A | ... | W G Q G T L V T V S S | SEQ ID NO:50 |
| R V T I S V D T S K N Q F S L K L S S V T A A D T A V Y Y C | ... | W G Q G T L V T V S S | SEQ ID NO:51 |
| R F T I S R D N S K N T L Y L Q M N S L R A E D T A V Y Y C A R | ... | W G Q G T L V T V S S | SEQ ID NO:52 |
| R F T I S R D N S K N T L Y L Q M N S L R A E D T A V Y Y C A R | ... | W G Q G T L V T V S S | SEQ ID NO:53 |
| R F T I S R D N S K N T L Y L Q M N S L R A E D T A V Y Y C A | ... | W G Q G T L V T V S S | SEQ ID NO:54 |
| R F T I S R D N S K N T L Y L Q M N S L R A E D T A V Y Y C | ... | W G Q G T L V T V S S | SEQ ID NO:55 |
| R F T I S D S K N T Y L Q M N S L R A E D T A V Y Y C R | ... | W G Q G T L V T V S S | SEQ ID NO:56 |
| R F T I S D S K N T Y L Q M N S L R A E D T A V Y Y C R | ... | W G Q G T L V T V S S | SEQ ID NO:57 |
| R F T I S D S K N T Y L Q M N S L R A E D T A V Y Y C | ... | W G Q G T L V T V S S | SEQ ID NO:58 |
| R F T I S D S K N T Y L Q M N S L R A E D T A V Y Y C A R | ... | W G Q G T L V T V S S | SEQ ID NO:59 |
| R F T I S D S K N T Y L Q M N S L R A E D T A V Y Y C A R | ... | W G Q G T L V T V S S | SEQ ID NO:60 |
| R F T I S D S K N T Y L Q M N S L R A E D T A V Y Y C A | ... | W G Q G T L V T V S S | SEQ ID NO:61 |
| R F T I S D S K N T Y L Q M N S L R A E D T A V Y Y C | ... | W G Q G T L V T V S S | SEQ ID NO:62 |

FIG. 8B

Rat anti-mouse Fib504 variable domains

FIG. 9A

Variable Light chain

DVVMTQSPATLSVTPGERISLSC<u>RASESVDTYLH</u>WYQQKPNESPRLLI<u>KYASQSIS</u>
GIPSRFSGSGSGTDFTLSINGVELEDLSIYYC<u>QQGNSLPNT</u>FGAGTKLELKRADAA
PTVSIFPPSMEQLTSGGATVVCFVNNFYPRDISVKWKIDGSEQRDGVLDSVTDQD
SKDSTYS  (SEQ ID NO:12)

FIG. 9B

Variable Heavy chain

EVQLQESGPGLVKPSQSLSLTCSVT<u>GFFITNNYWG</u>WIRKFPGNKMEWMG<u>YISYS
GSTSYNPSLKS</u>RISITRDTSKNQFFLQLNSVTTEDTATYYCA<u>MTGSSGYFDF</u>WGP
GTMVTVSSAETTAPSVYPLAPGTALKSNSMVTLGCLV  (SEQ ID NO:13)

FIG. 10A

Comparison of VH Framework Sequences

| | _____ Framework Region H3 _____ | | | | | | | |
|---|---|---|---|---|---|---|---|---|
| | 71 | 72 | 73 | 74 | 75 | 76 | 77 | 78 |
| hu subgroup I | A | D | T | S | T | S | T | A |
| hu subgroup II | V | D | T | S | K | N | Q | F |
| hu subgroup III | R | D | N | S | K | N | T | L |
| Herceptin | A | D | T | S | K | N | T | A |
| Fib504 | R | D | T | S | K | N | Q | F |
| Fib504-RL | R | D | T | S | K | N | T | L |
| Fib504-RF | R | D | T | S | K | N | T | F |

NOTE: Z is a stop codon. The most frequently observed amino acid is boxed.

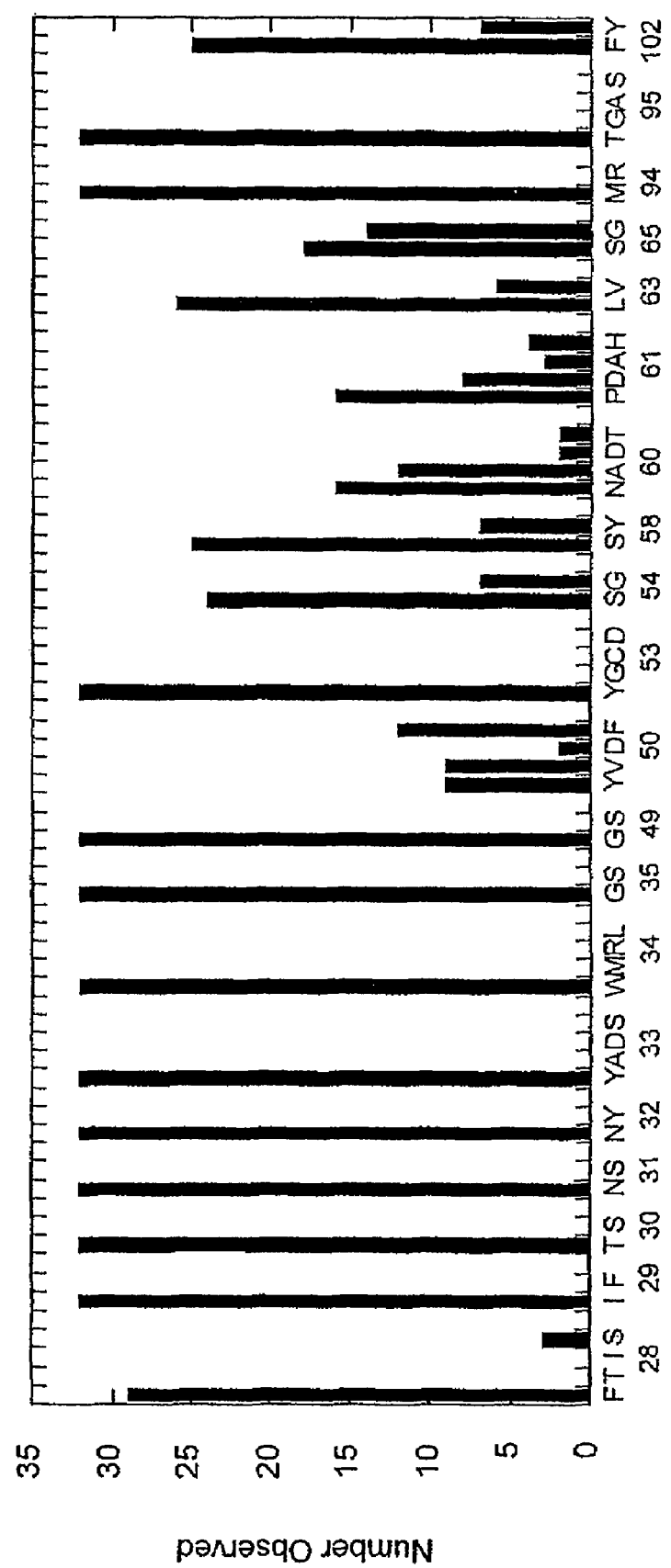

FIG. 12

| | amino acid position | amino acid number of times observed | | | | | | | | | | | |
|---|---|---|---|---|---|---|---|---|---|---|---|---|---|
| HVR-L1 | A25 | A 64 | G 2 | S 11 | T 7 | V 9 | | | | | | | |
| | S26 | G 4 | I 2 | K 3 | N 8 | P 1 | Q 1 | R 7 | S 64 | T 6 | | | |
| | E27 | A 6 | D 8 | E 60 | G 2 | H 1 | I 1 | K 4 | L 1 | N 2 | Q 5 | R 1 | V 2 |
| | S28 | A 1 | D 1 | G 7 | H 1 | I 1 | K 1 | N 1 | P 9 | R 3 | S 56 | T 4 | V 1 | Y 1 |
| | V29 | A 11 | G 6 | I 3 | K 1 | L 9 | M 6 | Q 1 | R 1 | V 55 | | | |
| | D30 | A 3 | D 59 | E 9 | G 3 | H 3 | I 1 | K 1 | L 1 | N 6 | P 1 | S 1 | T 2 | V 3 |
| | D31 | D 74 | E 13 | G 2 | N 1 | | | | | | | | |
| | L32 | I 1 | L 88 | M 4 | | | | | | | | | |
| | L33 | A 1 | I 5 | L 64 | M 1 | V 22 | | | | | | | |
| | H34 | F 1 | H 87 | Y 4 | S 1 | | | | | | | | |
| HVR L3 | N96 | A 2 | F 6 | H 1 | I 3 | L 47 | M 3 | N 2 | R 2 | S 2 | T 4 | V 2 | W 16 | Y 3 |
| HVR H3 | M94 | A 1 | E 3 | G 1 | M 48 | Q 10 | R 24 | S 8 | | | | | |

NOTE: The most frequently observed amino acid is shaded.

| | | rat FIB504 | human consensus | All Observed Amino Acids | Limited scan | Broad scan | Soft random (changes to 504) |
|---|---|---|---|---|---|---|---|
| | | R | R | | | | |
| CDR-L1 | 25 | A | A | AGSTV | | A G S T V | S |
| | | S | S | GIKNPQRST | | G I K N P Q R S T | |
| | 27 | E | Q | ADEGHIKLNQRV | E Q | A D E G H I K L N Q R V | D |
| | | S | S | ADGHIKNPRSTVY | | A D G H I K N P R S T V Y | D N |
| | 29 | V | I | AGIKLMQRV | V I | A G I K L M Q R V | |
| | | D | S | ADEGHIKLNPSTV | D S A | A D E G H I K L N P S T V | |
| | 31 | T | N | DEGNSP | D N | D E G N | S P N D |
| | | Y | Y | ILM | L | I L M | I L |
| | 33 | L | L | AILMV | | A I L M V | V |
| | | H | A | FHYS | H | F H Y S | |
| CDR-L2 | 49 | K | Y | KN | K N | | |
| | | Y | A | Y | Y | | |
| | 51 | A | A | | | | |
| | | S | S | | | | |
| | 53 | Q | S | QS | Q S | | |
| | | S | L | SLR | S L | | R |
| | 55 | I | E | EIKTV | I E K V | | T |
| | | S | S | | | | |
| CDR-L3 | 89 | Q | Q | | | | |
| | | Q | Q | | | | |
| | 91 | G | Y | G | G | | |
| | | N | N | | | | |
| | 93 | S | S | | | | |
| | | L | L | | | | |
| | 95 | P | P | | | | |
| | | N | W | AFHILMNRSTVWY | N W Y R S | A F H I L M N R S T V W Y | |
| | 97 | T | T | | | | |
| CDR-H1 | 26 | G | G | | | | |
| | | F | F | | | | |
| | 28 | F | T | F | F | | |
| | | I | F | I | I | | |
| | 30 | T | S | T | T | | |
| | | N | S | N | N | | |
| | 32 | N | Y | N | N | | |
| | | Y | A | Y | Y | | |
| | 34 | W | M | W | W | | |
| | | G | S | G | G | | |
| CDR-H2 | 49 | G | S | G | G | | |
| | | Y | V | DFVY | Y V D F | | |
| | 51 | I | I | | | | |
| | | S | S | | | | |
| | 53 | Y | G | Y | Y | | |
| | | S | G | GS | S G | | |
| | 55 | G | G | | | | |
| | | S | S | | | | |
| | 57 | T | T | | | | |
| | | S | Y | SY | S Y | | |
| | 59 | Y | Y | | | | |
| | | N | A | ADNT | N A D T | | |
| | 61 | P | D | ADHP | P D A H | | |
| | | S | S | | | | |
| | 63 | L | V | LV | L V | | |
| | | K | K | | | | |
| | 65 | S | G | GS | S G | | |
| CDR-H3 | 93 | A | A | | | | |
| | | M | R | AEGMQRS | M | A E G M Q R S | |
| | 95 | T | G | T | T | | |
| | | G | | | | | |
| | 97 | S | | | | | |
| | | S | | | | | |
| | 99 | G | | | | | |
| | | Y | | | | | |
| | | F | F | | | | |
| | # | D | D | | | | |
| | | F | Y | FY | F Y | | |

FIG. 13

| | Position | | 504.32R | Amino Acid Substitutions | | | | | | | | | | | | |
|---|---|---|---|---|---|---|---|---|---|---|---|---|---|---|---|---|
| | Kabat # | Relative | amino acid | | | | | | | | | | | | | |
| HVR-L1 | 24 | A1 | R | | | | | | | | | | | | | |
| | 25 | A2 | A | G | S | T | V | | | | | | | | | |
| | 26 | A3 | S | G | I | K | N | P | Q | R | T | | | | | |
| | 27 | A4 | E | V | Q | A | D | G | H | I | K | L | N | R | | |
| | 28 | A5 | S | Y | A | D | G | H | L | K | N | P | R | T | V |
| | 29 | A6 | V | R | I | A | G | K | G | S | Q | | | | | |
| | 30 | A7 | D | V | S | E | E | P | | | | L | N | P | S | T |
| | 31 | A8 | D | G | N | M | T | | | | | | | | | |
| | 32 | A9 | L | Y | I | M | | | | | | | | | | |
| | 33 | A10 | L | A | I | M | V | | | | | | | | | |
| | 34 | A11 | H | Y | F | S | | | | | | | | | | |
| HVR-L2 | 49 | B1 | K | Y | N | | | | | | | | | | | |
| | 50 | B2 | Y | | | | | | | | | | | | | |
| | 51 | B3 | A | | | | | | | | | | | | | |
| | 52 | B4 | S | D | | | | | | | | | | | | |
| | 53 | B5 | Q | S | | | | | | | | | | | | |
| | 54 | B6 | S | D | L | R | | | | | | | | | | |
| | 55 | B7 | I | V | E | K | T | | | | | | | | | |
| | 56 | B8 | S | | | | | | | | | | | | | |
| HVR-L3 | 89 | C1 | Q | | | | | | | | | | | | | |
| | 90 | C2 | Q | | | | | | | | | | | | | |
| | 91 | C3 | G | | | | | | | | | | | | | |
| | 92 | C4 | N | | | | | | | | | | | | | |
| | 93 | C5 | S | | | | | | | | | | | | | |
| | 94 | C6 | L | | | | | | | | | | | | | |
| | 95 | C7 | P | | | | | | | | | | | | | |
| | 96 | C8 | N | V | W | Y | R | S | T | A | F | H | I | L | M |
| | 97 | C9 | T | | | | | | | | | | | | | |
| HVR-H1 | 26 | D1 | G | | | | | | | | | | | | | |
| | 27 | D2 | F | | | | | | | | | | | | | |
| | 28 | D3 | F | | | | | | | | | | | | | |
| | 29 | D4 | I | | | | | | | | | | | | | |
| | 30 | D5 | T | | | | | | | | | | | | | |
| | 31 | D6 | N | | | | | | | | | | | | | |
| | 32 | D7 | N | | | | | | | | | | | | | |
| | 33 | D8 | Y | | | | | | | | | | | | | |
| | 34 | D9 | W | | | | | | | | | | | | | |
| | 35 | D10 | G | | | | | | | | | | | | | |
| HVR-H2 | 49 | E1 | G | | | | | | | | | | | | | |
| | 50 | E2 | Y | F | V | D | | | | | | | | | | |
| | 51 | E3 | I | | | | | | | | | | | | | |
| | 52 | E4 | S | | | | | | | | | | | | | |
| | 53 | E5 | Y | | | | | | | | | | | | | |
| | 54 | E6 | S | G | | | | | | | | | | | | |
| | 55 | E7 | G | | | | | | | | | | | | | |
| | 56 | E8 | S | | | | | | | | | | | | | |
| | 57 | E9 | T | | | | | | | | | | | | | |
| | 58 | E10 | S | Y | | | | | | | | | | | | |
| | 59 | E11 | Y | | | | | | | | | | | | | |
| | 60 | E12 | N | T | A | D | | | | | | | | | | |
| | 61 | E13 | P | H | D | A | | | | | | | | | | |
| | 62 | E14 | S | | | | | | | | | | | | | |
| | 63 | E15 | L | V | | | | | | | | | | | | |
| | 64 | E16 | K | | | | | | | | | | | | | |
| | 65 | E17 | S | G | | | | | | | | | | | | |
| HVR-H3 | 93 | F1 | A | | | | | | | | | | | | | |
| | 94 | F2 | R | M | A | E | G | Q | S | | | | | | | |
| | 95 | F3 | T | | | | | | | | | | | | | |
| | 96 | F4 | G | | | | | | | | | | | | | |
| | 97 | F5 | S | | | | | | | | | | | | | |
| | 98 | F6 | S | | | | | | | | | | | | | |
| | 99 | F7 | G | | | | | | | | | | | | | |
| | 100 | F8 | Y | | | | | | | | | | | | | |
| | k | F9 | F | | | | | | | | | | | | | |
| | 101 | F10 | D | | | | | | | | | | | | | |
| | 102 | F11 | F | Y | | | | | | | | | | | | |
| Heavy chain FR3 | 71 | | R | A | T | | | | | | | | | | | |
| | 73 | | T | N | | | | | | | | | | | | |
| | 78 | | F | A | F | L | | | | | | | | | | |

Fig. 15

SEQUENCE LISTING

<160> NUMBER OF SEQ ID NOS: 68

<210> SEQ ID NO 1
<211> LENGTH: 11
<212> TYPE: PRT
<213> ORGANISM: Artificial sequence
<220> FEATURE:
<223> OTHER INFORMATION: sequence is synthesized

<400> SEQUENCE: 1

Arg Ala Ser Glu Ser Val Asp Thr Tyr Leu His
                 5                   10

```
<210> SEQ ID NO 2
<211> LENGTH: 8
<212> TYPE: PRT
<213> ORGANISM: Artificial sequence
<220> FEATURE:
<223> OTHER INFORMATION: sequence is synthesized

<400> SEQUENCE: 2

Lys Tyr Ala Ser Gln Ser Ile Ser
                5

<210> SEQ ID NO 3
<211> LENGTH: 9
<212> TYPE: PRT
<213> ORGANISM: Artificial sequence
<220> FEATURE:
<223> OTHER INFORMATION: sequence is synthesized

<400> SEQUENCE: 3

Gln Gln Gly Asn Ser Leu Pro Asn Thr
                5

<210> SEQ ID NO 4
<211> LENGTH: 10
<212> TYPE: PRT
<213> ORGANISM: Artificial sequence
<220> FEATURE:
<223> OTHER INFORMATION: sequence is synthesized

<400> SEQUENCE: 4

Gly Phe Phe Ile Thr Asn Asn Tyr Trp Gly
                5                   10

<210> SEQ ID NO 5
<211> LENGTH: 17
<212> TYPE: PRT
<213> ORGANISM: Artificial sequence
<220> FEATURE:
<223> OTHER INFORMATION: sequence is synthesized

<400> SEQUENCE: 5

Gly Tyr Ile Ser Tyr Ser Gly Ser Thr Ser Tyr Asn Pro Ser Leu
 1               5                  10                  15

Lys Ser

<210> SEQ ID NO 6
<211> LENGTH: 10
<212> TYPE: PRT
<213> ORGANISM: Artificial sequence
<220> FEATURE:
<223> OTHER INFORMATION: sequence is synthesized

<400> SEQUENCE: 6

Met Thr Gly Ser Ser Gly Tyr Phe Asp Phe
                5                   10

<210> SEQ ID NO 7
<211> LENGTH: 11
<212> TYPE: PRT
<213> ORGANISM: Artificial sequence
<220> FEATURE:
<223> OTHER INFORMATION: sequence is synthesized

<400> SEQUENCE: 7

Arg Ala Ser Glu Ser Val Asp Ser Leu Leu His
                5                   10
```

```
<210> SEQ ID NO 8
<211> LENGTH: 11
<212> TYPE: PRT
<213> ORGANISM: Artificial sequence
<220> FEATURE:
<223> OTHER INFORMATION: sequence is synthesized

<400> SEQUENCE: 8

Arg Ala Ser Glu Ser Val Asp Thr Leu Leu His
                 5                  10

<210> SEQ ID NO 9
<211> LENGTH: 11
<212> TYPE: PRT
<213> ORGANISM: Artificial sequence
<220> FEATURE:
<223> OTHER INFORMATION: sequence is synthesized

<400> SEQUENCE: 9

Arg Ala Ser Glu Ser Val Asp Asp Leu Leu His
                 5                  10

<210> SEQ ID NO 10
<211> LENGTH: 108
<212> TYPE: PRT
<213> ORGANISM: Artificial sequence
<220> FEATURE:
<223> OTHER INFORMATION: sequence is synthesized

<400> SEQUENCE: 10

Asp Val Val Met Thr Gln Ser Pro Ala Thr Leu Ser Val Thr Pro
 1               5                  10                  15

Gly Glu Arg Ile Ser Leu Ser Cys Arg Ala Ser Glu Ser Val Asp
                20                  25                  30

Thr Tyr Leu His Trp Tyr Gln Gln Lys Pro Asn Glu Ser Pro Arg
                35                  40                  45

Leu Leu Ile Lys Tyr Ala Ser Gln Ser Ile Ser Gly Ile Pro Ser
                50                  55                  60

Arg Phe Ser Gly Ser Gly Ser Gly Thr Asp Phe Thr Leu Ser Ile
                65                  70                  75

Asn Gly Val Glu Leu Glu Asp Leu Ser Ile Tyr Tyr Cys Gln Gln
                80                  85                  90

Gly Asn Ser Leu Pro Asn Thr Phe Gly Ala Gly Thr Lys Leu Glu
                95                  100                 105

Leu Lys Arg

<210> SEQ ID NO 11
<211> LENGTH: 117
<212> TYPE: PRT
<213> ORGANISM: Artificial sequence
<220> FEATURE:
<223> OTHER INFORMATION: sequence is synthesized

<400> SEQUENCE: 11

Glu Val Gln Leu Gln Glu Ser Gly Pro Gly Leu Val Lys Pro Ser
 1               5                  10                  15

Gln Ser Leu Ser Leu Thr Cys Ser Val Thr Gly Phe Phe Ile Thr
                20                  25                  30

Asn Asn Tyr Trp Gly Trp Ile Arg Lys Phe Pro Gly Asn Lys Met
                35                  40                  45

Glu Trp Met Gly Tyr Ile Ser Tyr Ser Gly Ser Thr Ser Tyr Asn
                50                  55                  60
```

```
Pro Ser Leu Lys Ser Arg Ile Ser Ile Thr Arg Asp Thr Ser Lys
            65                  70                  75

Asn Gln Phe Phe Leu Gln Leu Asn Ser Val Thr Thr Glu Asp Thr
                80                  85                  90

Ala Thr Tyr Tyr Cys Ala Met Thr Gly Ser Ser Gly Tyr Phe Asp
                95                 100                 105

Phe Trp Gly Pro Gly Thr Met Val Thr Val Ser Ser
                110                 115

<210> SEQ ID NO 12
<211> LENGTH: 174
<212> TYPE: PRT
<213> ORGANISM: Artificial sequence
<220> FEATURE:
<223> OTHER INFORMATION: sequence is synthesized

<400> SEQUENCE: 12

Asp Val Val Met Thr Gln Ser Pro Ala Thr Leu Ser Val Thr Pro
 1               5                  10                  15

Gly Glu Arg Ile Ser Leu Ser Cys Arg Ala Ser Glu Ser Val Asp
                20                  25                  30

Thr Tyr Leu His Trp Tyr Gln Gln Lys Pro Asn Glu Ser Pro Arg
                35                  40                  45

Leu Leu Ile Lys Tyr Ala Ser Gln Ser Ile Ser Gly Ile Pro Ser
                50                  55                  60

Arg Phe Ser Gly Ser Gly Ser Gly Thr Asp Phe Thr Leu Ser Ile
            65                  70                  75

Asn Gly Val Glu Leu Glu Asp Leu Ser Ile Tyr Tyr Cys Gln Gln
                80                  85                  90

Gly Asn Ser Leu Pro Asn Thr Phe Gly Ala Gly Thr Lys Leu Glu
                95                 100                 105

Leu Lys Arg Ala Asp Ala Ala Pro Thr Val Ser Ile Phe Pro Pro
                110                 115                 120

Ser Met Glu Gln Leu Thr Ser Gly Gly Ala Thr Val Val Cys Phe
                125                 130                 135

Val Asn Asn Phe Tyr Pro Arg Asp Ile Ser Val Lys Trp Lys Ile
                140                 145                 150

Asp Gly Ser Glu Gln Arg Asp Gly Val Leu Asp Ser Val Thr Asp
                155                 160                 165

Gln Asp Ser Lys Asp Ser Thr Tyr Ser
                170

<210> SEQ ID NO 13
<211> LENGTH: 146
<212> TYPE: PRT
<213> ORGANISM: Artificial sequence
<220> FEATURE:
<223> OTHER INFORMATION: sequence is synthesized

<400> SEQUENCE: 13

Glu Val Gln Leu Gln Glu Ser Gly Pro Gly Leu Val Lys Pro Ser
 1               5                  10                  15

Gln Ser Leu Ser Leu Thr Cys Ser Val Thr Gly Phe Ile Thr
                20                  25                  30

Asn Asn Tyr Trp Gly Trp Ile Arg Lys Phe Pro Gly Asn Lys Met
                35                  40                  45

Glu Trp Met Gly Tyr Ile Ser Tyr Ser Gly Ser Thr Ser Tyr Asn
                50                  55                  60
```

```
Pro Ser Leu Lys Ser Arg Ile Ser Ile Thr Arg Asp Thr Lys
            65                  70                  75

Asn Gln Phe Phe Leu Gln Leu Asn Ser Val Thr Thr Glu Asp Thr
                80                  85                  90

Ala Thr Tyr Tyr Cys Ala Met Thr Gly Ser Ser Gly Tyr Phe Asp
                95                 100                 105

Phe Trp Gly Pro Gly Thr Met Val Thr Val Ser Ser Ala Glu Thr
               110                 115                 120

Thr Ala Pro Ser Val Tyr Pro Leu Ala Pro Gly Thr Ala Leu Lys
               125                 130                 135

Ser Asn Ser Met Val Thr Leu Gly Cys Leu Val
               140                 145
```

<210> SEQ ID NO 14
<211> LENGTH: 80
<212> TYPE: PRT
<213> ORGANISM: Artificial sequence
<220> FEATURE:
<223> OTHER INFORMATION: sequence is synthesized

<400> SEQUENCE: 14

```
Asp Ile Gln Met Thr Gln Ser Pro Ser Ser Leu Ser Ala Ser Val
  1               5                  10                  15

Gly Asp Arg Val Thr Ile Thr Cys Trp Tyr Gln Gln Lys Pro Gly
                 20                  25                  30

Lys Ala Pro Lys Leu Leu Ile Tyr Gly Val Pro Ser Arg Phe Ser
                 35                  40                  45

Gly Ser Gly Ser Gly Thr Asp Phe Thr Leu Thr Ile Ser Ser Leu
                 50                  55                  60

Gln Pro Glu Asp Phe Ala Thr Tyr Tyr Cys Phe Gly Gln Gly Thr
                 65                  70                  75

Lys Val Glu Ile Lys
                 80
```

<210> SEQ ID NO 15
<211> LENGTH: 79
<212> TYPE: PRT
<213> ORGANISM: Artificial sequence
<220> FEATURE:
<223> OTHER INFORMATION: sequence is synthesized

<400> SEQUENCE: 15

```
Asp Ile Gln Met Thr Gln Ser Pro Ser Ser Leu Ser Ala Ser Val
  1               5                  10                  15

Gly Asp Arg Val Thr Ile Thr Cys Trp Tyr Gln Gln Lys Pro Gly
                 20                  25                  30

Lys Ala Pro Lys Leu Leu Ile Gly Val Pro Ser Arg Phe Ser Gly
                 35                  40                  45

Ser Gly Ser Gly Thr Asp Phe Thr Leu Thr Ile Ser Ser Leu Gln
                 50                  55                  60

Pro Glu Asp Phe Ala Thr Tyr Tyr Cys Phe Gly Gln Gly Thr Lys
                 65                  70                  75

Val Glu Ile Lys
```

<210> SEQ ID NO 16
<211> LENGTH: 80
<212> TYPE: PRT
<213> ORGANISM: Artificial sequence
<220> FEATURE:
<223> OTHER INFORMATION: sequence is synthesized

<400> SEQUENCE: 16

Asp Ile Val Met Thr Gln Ser Pro Leu Ser Leu Pro Val Thr Pro
1               5                  10                  15

Gly Glu Pro Ala Ser Ile Ser Cys Trp Tyr Leu Gln Lys Pro Gly
            20                  25                  30

Gln Ser Pro Gln Leu Leu Ile Tyr Gly Val Pro Asp Arg Phe Ser
        35                  40                  45

Gly Ser Gly Ser Gly Thr Asp Phe Thr Leu Lys Ile Ser Arg Val
    50                  55                  60

Glu Ala Glu Asp Val Gly Val Tyr Tyr Cys Phe Gly Gln Gly Thr
65                  70                  75

Lys Val Glu Ile Lys
            80

<210> SEQ ID NO 17
<211> LENGTH: 80
<212> TYPE: PRT
<213> ORGANISM: Artificial sequence
<220> FEATURE:
<223> OTHER INFORMATION: sequence is synthesized

<400> SEQUENCE: 17

Glu Ile Val Leu Thr Gln Ser Pro Gly Thr Leu Ser Leu Ser Pro
1               5                  10                  15

Gly Glu Arg Ala Thr Leu Ser Cys Trp Tyr Gln Gln Lys Pro Gly
            20                  25                  30

Gln Ala Pro Arg Leu Leu Ile Tyr Gly Ile Pro Asp Arg Phe Ser
        35                  40                  45

Gly Ser Gly Ser Gly Thr Asp Phe Thr Leu Thr Ile Ser Arg Leu
    50                  55                  60

Glu Pro Glu Asp Phe Ala Val Tyr Tyr Cys Phe Gly Gln Gly Thr
65                  70                  75

Lys Val Glu Ile Lys
            80

<210> SEQ ID NO 18
<211> LENGTH: 80
<212> TYPE: PRT
<213> ORGANISM: Artificial sequence
<220> FEATURE:
<223> OTHER INFORMATION: sequence is synthesized

<400> SEQUENCE: 18

Asp Ile Val Met Thr Gln Ser Pro Asp Ser Leu Ala Val Ser Leu
1               5                  10                  15

Gly Glu Arg Ala Thr Ile Asn Cys Trp Tyr Gln Gln Lys Pro Gly
            20                  25                  30

Gln Pro Pro Lys Leu Leu Ile Tyr Gly Val Pro Asp Arg Phe Ser
        35                  40                  45

Gly Ser Gly Ser Gly Thr Asp Phe Thr Leu Thr Ile Ser Ser Leu
    50                  55                  60

Gln Ala Glu Asp Val Ala Val Tyr Tyr Cys Phe Gly Gln Gly Thr
65                  70                  75

Lys Val Glu Ile Lys
            80

<210> SEQ ID NO 19
<211> LENGTH: 87

```
<212> TYPE: PRT
<213> ORGANISM: Artificial sequence
<220> FEATURE:
<223> OTHER INFORMATION: sequence is synthesized

<400> SEQUENCE: 19

Gln Val Gln Leu Val Gln Ser Gly Ala Glu Val Lys Lys Pro Gly
 1               5                  10                  15

Ala Ser Val Lys Val Ser Cys Lys Ala Ser Gly Tyr Thr Phe Thr
            20                  25                  30

Trp Val Arg Gln Ala Pro Gly Gln Gly Leu Glu Trp Met Gly Arg
        35                  40                  45

Val Thr Ile Thr Ala Asp Thr Ser Thr Ser Thr Ala Tyr Met Glu
    50                  55                  60

Leu Ser Ser Leu Arg Ser Glu Asp Thr Ala Val Tyr Tyr Cys Ala
65                  70                  75

Arg Trp Gly Gln Gly Thr Leu Val Thr Val Ser Ser
            80                  85

<210> SEQ ID NO 20
<211> LENGTH: 81
<212> TYPE: PRT
<213> ORGANISM: Artificial sequence
<220> FEATURE:
<223> OTHER INFORMATION: sequence is synthesized

<400> SEQUENCE: 20

Gln Val Gln Leu Val Gln Ser Gly Ala Glu Val Lys Lys Pro Gly
 1               5                  10                  15

Ala Ser Val Lys Val Ser Cys Lys Ala Ser Trp Val Arg Gln Ala
            20                  25                  30

Pro Gly Gln Gly Leu Glu Trp Met Arg Val Thr Ile Thr Ala Asp
        35                  40                  45

Thr Ser Thr Ser Thr Ala Tyr Met Glu Leu Ser Ser Leu Arg Ser
    50                  55                  60

Glu Asp Thr Ala Val Tyr Tyr Cys Ala Arg Trp Gly Gln Gly Thr
65                  70                  75

Leu Val Thr Val Ser Ser
            80

<210> SEQ ID NO 21
<211> LENGTH: 80
<212> TYPE: PRT
<213> ORGANISM: Artificial sequence
<220> FEATURE:
<223> OTHER INFORMATION: sequence is synthesized

<400> SEQUENCE: 21

Gln Val Gln Leu Val Gln Ser Gly Ala Glu Val Lys Lys Pro Gly
 1               5                  10                  15

Ala Ser Val Lys Val Ser Cys Lys Ala Ser Trp Val Arg Gln Ala
            20                  25                  30

Pro Gly Gln Gly Leu Glu Trp Met Arg Val Thr Ile Thr Ala Asp
        35                  40                  45

Thr Ser Thr Ser Thr Ala Tyr Met Glu Leu Ser Ser Leu Arg Ser
    50                  55                  60

Glu Asp Thr Ala Val Tyr Tyr Cys Ala Trp Gly Gln Gly Thr Leu
65                  70                  75

Val Thr Val Ser Ser
            80
```

```
<210> SEQ ID NO 22
<211> LENGTH: 79
<212> TYPE: PRT
<213> ORGANISM: Artificial sequence
<220> FEATURE:
<223> OTHER INFORMATION: sequence is synthesized

<400> SEQUENCE: 22

Gln Val Gln Leu Val Gln Ser Gly Ala Glu Val Lys Lys Pro Gly
 1               5                  10                  15

Ala Ser Val Lys Val Ser Cys Lys Ala Ser Trp Val Arg Gln Ala
                20                  25                  30

Pro Gly Gln Gly Leu Glu Trp Met Arg Val Thr Ile Thr Ala Asp
                35                  40                  45

Thr Ser Thr Ser Thr Ala Tyr Met Glu Leu Ser Ser Leu Arg Ser
                50                  55                  60

Glu Asp Thr Ala Val Tyr Tyr Cys Trp Gly Gln Gly Thr Leu Val
                65                  70                  75

Thr Val Ser Ser

<210> SEQ ID NO 23
<211> LENGTH: 108
<212> TYPE: PRT
<213> ORGANISM: Artificial sequence
<220> FEATURE:
<223> OTHER INFORMATION: sequence is synthesized

<400> SEQUENCE: 23

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
                35                  40                  45

Leu Leu Ile Tyr Ala Ala Ser Ser Leu Glu Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Asn Ser Leu Pro Trp Thr Phe Gly Gln Gly Thr Lys Val Glu
                95                 100                 105

Ile Lys Arg

<210> SEQ ID NO 24
<211> LENGTH: 113
<212> TYPE: PRT
<213> ORGANISM: Artificial sequence
<220> FEATURE:
<223> OTHER INFORMATION: sequence is synthesized

<400> SEQUENCE: 24

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
                35                  40                  45
```

```
Glu Trp Val Ser Val Ile Ser Gly Asp Gly Ser Thr Tyr Tyr
             50                  55                  60

Ala Asp Ser Val Lys Gly Arg Phe Thr Ile Ser Arg Asp Asn Ser
            65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Phe Asp Tyr Trp Gly Gln
                95                 100                 105

Gly Thr Leu Val Thr Val Ser Ser
            110

<210> SEQ ID NO 25
<211> LENGTH: 108
<212> TYPE: PRT
<213> ORGANISM: Artificial sequence
<220> FEATURE:
<223> OTHER INFORMATION: sequence is synthesized

<400> SEQUENCE: 25

Asp Ile Gln Met Thr Gln Ser Pro Ser Ser Leu Ser Ala Ser Val
 1               5                  10                  15

Gly Asp Arg Val Thr Ile Thr Cys Arg Ala Ser Glu Ser Val Asp
                20                  25                  30

Thr Tyr Leu His Trp Tyr Gln Gln Lys Pro Gly Lys Ala Pro Lys
                35                  40                  45

Leu Leu Ile Lys Tyr Ala Ser Gln Ser Ile Ser Gly Val Pro Ser
            50                  55                  60

Arg Phe Ser Gly Ser Gly Ser Gly Thr Asp Phe Thr Leu Thr Ile
 65                 70                  75

Ser Ser Leu Gln Pro Glu Asp Phe Ala Thr Tyr Tyr Cys Gln Gln
                80                  85                  90

Gly Asn Ser Leu Pro Asn Thr Phe Gly Gln Gly Thr Lys Val Glu
                95                 100                 105

Ile Lys Arg

<210> SEQ ID NO 26
<211> LENGTH: 117
<212> TYPE: PRT
<213> ORGANISM: Artificial sequence
<220> FEATURE:
<223> OTHER INFORMATION: sequence is synthesized

<400> SEQUENCE: 26

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Phe Ile Thr
                20                  25                  30

Asn Asn Tyr Trp Gly Trp Val Arg Gln Ala Pro Gly Lys Gly Leu
                35                  40                  45

Glu Trp Val Gly Tyr Ile Ser Tyr Ser Gly Ser Thr Ser Tyr Asn
                50                  55                  60

Pro Ser Leu Lys Ser Arg Phe Thr Ile Ser Ala Asp Thr Ser Lys
            65                  70                  75

Asn Thr Ala Tyr Leu Gln Met Asn Ser Leu Arg Ala Glu Asp Thr
                80                  85                  90

Ala Val Tyr Tyr Cys Ala Met Thr Gly Ser Ser Gly Tyr Phe Asp
                95                 100                 105

Phe Trp Gly Gln Gly Thr Leu Val Thr Val Ser Ser
```

<210> SEQ ID NO 27
<211> LENGTH: 214
<212> TYPE: PRT
<213> ORGANISM: Artificial sequence
<220> FEATURE:
<223> OTHER INFORMATION: sequence is synthesized

<400> SEQUENCE: 27

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser
            20                  25                  30

Asn Tyr Leu Ala Trp Tyr Gln Gln Lys Pro Gly Lys Ala Pro Lys
            35                  40                  45

Leu Leu Ile Tyr Ala Ala Ser Ser Leu Glu Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Asn Ser Leu Pro Trp Thr Phe Gly Gln Gly Thr Lys Val Glu
            95                  100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 28
<211> LENGTH: 448
<212> TYPE: PRT
<213> ORGANISM: Artificial sequence
<220> FEATURE:
<223> OTHER INFORMATION: sequence is synthesized

<400> SEQUENCE: 28

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu
            35                  40                  45

Glu Trp Val Ser Val Ile Ser Gly Asp Gly Gly Ser Thr Tyr Tyr
            50                  55                  60

Ala Asp Ser Val Lys Gly Arg Phe Thr Ile Ser Arg Asp Asn Ser
            65                  70                  75

Lys Asn Thr Leu Tyr Leu Gln Met Asn Ser Leu Arg Ala Glu Asp
            80                  85                  90

Thr Ala Val Tyr Tyr Cys Ala Met Thr Gly Ser Ser Gly Tyr Phe
            95                 100                 105

Asp Phe Trp Gly Gln Gly Thr Leu Val Thr Val Ser Ser Ala Ser
           110                 115                 120

Thr Lys Gly Pro Ser Val Phe Pro Leu Ala Pro Ser Ser Lys Ser
           125                 130                 135

Thr Ser Gly Gly Thr Ala Ala Leu Gly Cys Leu Val Lys Asp Tyr
           140                 145                 150

Phe Pro Glu Pro Val Thr Val Ser Trp Asn Ser Gly Ala Leu Thr
           155                 160                 165

Ser Gly Val His Thr Phe Pro Ala Val Leu Gln Ser Ser Gly Leu
           170                 175                 180

Tyr Ser Leu Ser Ser Val Val Thr Val Pro Ser Ser Ser Leu Gly
           185                 190                 195

Thr Gln Thr Tyr Ile Cys Asn Val Asn His Lys Pro Ser Asn Thr
           200                 205                 210

Lys Val Asp Lys Lys Val Glu Pro Lys Ser Cys Asp Lys Thr His
           215                 220                 225

Thr Cys Pro Pro Cys Pro Ala Pro Glu Leu Leu Gly Gly Pro Ser
           230                 235                 240

Val Phe Leu Phe Pro Pro Lys Pro Lys Asp Thr Leu Met Ile Ser
           245                 250                 255

Arg Thr Pro Glu Val Thr Cys Val Val Asp Val Ser His Glu
           260                 265                 270

Asp Pro Glu Val Lys Phe Asn Trp Tyr Val Asp Gly Val Glu Val
           275                 280                 285

His Asn Ala Lys Thr Lys Pro Arg Glu Glu Gln Tyr Asn Ser Thr
           290                 295                 300

Tyr Arg Val Val Ser Val Leu Thr Val Leu His Gln Asp Trp Leu
           305                 310                 315

Asn Gly Lys Glu Tyr Lys Cys Lys Val Ser Asn Lys Ala Leu Pro
           320                 325                 330

Ala Pro Ile Glu Lys Thr Ile Ser Lys Ala Lys Gly Gln Pro Arg
           335                 340                 345

Glu Pro Gln Val Tyr Thr Leu Pro Pro Ser Arg Glu Glu Met Thr
           350                 355                 360

Lys Asn Gln Val Ser Leu Thr Cys Leu Val Lys Gly Phe Tyr Pro
           365                 370                 375

Ser Asp Ile Ala Val Glu Trp Glu Ser Asn Gly Gln Pro Glu Asn
           380                 385                 390

Asn Tyr Lys Thr Thr Pro Pro Val Leu Asp Ser Asp Gly Ser Phe
           395                 400                 405

Phe Leu Tyr Ser Lys Leu Thr Val Asp Lys Ser Arg Trp Gln Gln
           410                 415                 420

Gly Asn Val Phe Ser Cys Ser Val Met His Glu Ala Leu His Asn
           425                 430                 435

His Tyr Thr Gln Lys Ser Leu Ser Leu Ser Pro Gly Lys
           440                 445

<210> SEQ ID NO 29
<211> LENGTH: 214
<212> TYPE: PRT

<213> ORGANISM: Artificial sequence
<220> FEATURE:
<223> OTHER INFORMATION: sequence is synthesized

<400> SEQUENCE: 29

```
Asp Ile Gln Met Thr Gln Ser Pro Ser Ser Leu Ser Ala Ser Val
 1               5                  10                  15

Gly Asp Arg Val Thr Ile Thr Cys Arg Ala Ser Glu Ser Val Asp
                20                  25                  30

Thr Tyr Leu His Trp Tyr Gln Gln Lys Pro Gly Lys Ala Pro Lys
                35                  40                  45

Leu Leu Ile Tyr Tyr Ala Ser Gln Ser Ile Ser Gly Val Pro Ser
                50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
                80                  85                  90

Gly Asn Ser Leu Pro Asn Thr Phe Gly Gln Gly Thr Lys Val Glu
                95                 100                 105

Ile Lys Arg Thr Val Ala Ala Pro Ser Val Phe Ile Phe Pro Pro
                110                 115                 120

Ser Asp Glu Gln Leu Lys Ser Gly Thr Ala Ser Val Val Cys Leu
                125                 130                 135

Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195

Val Thr His Gln Gly Leu Ser Ser Pro Val Thr Lys Ser Phe Asn
                200                 205                 210

Arg Gly Glu Cys
```

<210> SEQ ID NO 30
<211> LENGTH: 447
<212> TYPE: PRT
<213> ORGANISM: Artificial sequence
<220> FEATURE:
<223> OTHER INFORMATION: sequence is synthesized

<400> SEQUENCE: 30

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Ile Thr
                20                  25                  30

Asn Asn Tyr Trp Gly Trp Val Arg Gln Ala Pro Gly Lys Gly Leu
                35                  40                  45

Glu Trp Val Gly Tyr Ile Ser Tyr Ser Gly Ser Thr Tyr Tyr Asn
                50                  55                  60

Pro Ser Leu Lys Ser Arg Phe Thr Ile Ser Ala Asp Thr Ser Lys
 65                  70                  75

Asn Thr Ala Tyr Leu Gln Met Asn Ser Leu Arg Ala Glu Asp Thr
                80                  85                  90

Ala Val Tyr Tyr Cys Ala Met Thr Gly Ser Ser Gly Tyr Phe Asp
                95                 100                 105
```

-continued

```
Phe Trp Gly Gln Gly Thr Leu Val Thr Val Ser Ser Ala Ser Thr
            110                 115                 120

Lys Gly Pro Ser Val Phe Pro Leu Ala Pro Ser Ser Lys Ser Thr
            125                 130                 135

Ser Gly Gly Thr Ala Ala Leu Gly Cys Leu Val Lys Asp Tyr Phe
            140                 145                 150

Pro Glu Pro Val Thr Val Ser Trp Asn Ser Gly Ala Leu Thr Ser
            155                 160                 165

Gly Val His Thr Phe Pro Ala Val Leu Gln Ser Ser Gly Leu Tyr
            170                 175                 180

Ser Leu Ser Ser Val Val Thr Val Pro Ser Ser Ser Leu Gly Thr
            185                 190                 195

Gln Thr Tyr Ile Cys Asn Val Asn His Lys Pro Ser Asn Thr Lys
            200                 205                 210

Val Asp Lys Lys Val Glu Pro Lys Ser Cys Asp Lys Thr His Thr
            215                 220                 225

Cys Pro Pro Cys Pro Ala Pro Glu Leu Leu Gly Gly Pro Ser Val
            230                 235                 240

Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp
            260                 265                 270

Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn
            305                 310                 315

Gly Lys Glu Tyr Lys Cys Lys Val Ser Asn Lys Ala Leu Pro Ala
            320                 325                 330

Pro Ile Glu Lys Thr Ile Ser Lys Ala Lys Gly Gln Pro Arg Glu
            335                 340                 345

Pro Gln Val Tyr Thr Leu Pro Pro Ser Arg Glu Glu Met Thr Lys
            350                 355                 360

Asn Gln Val Ser Leu Thr Cys Leu Val Lys Gly Phe Tyr Pro Ser
            365                 370                 375

Asp Ile Ala Val Glu Trp Glu Ser Asn Gly Gln Pro Glu Asn Asn
            380                 385                 390

Tyr Lys Thr Thr Pro Pro Val Leu Asp Ser Asp Gly Ser Phe Phe
            395                 400                 405

Leu Tyr Ser Lys Leu Thr Val Asp Lys Ser Arg Trp Gln Gln Gly
            410                 415                 420

Asn Val Phe Ser Cys Ser Val Met His Glu Ala Leu His Asn His
            425                 430                 435

Tyr Thr Gln Lys Ser Leu Ser Leu Ser Pro Gly Lys
            440                 445
```

<210> SEQ ID NO 31
<211> LENGTH: 214
<212> TYPE: PRT
<213> ORGANISM: Artificial sequence
<220> FEATURE:
<223> OTHER INFORMATION: sequence is synthesized

<400> SEQUENCE: 31

```
Asp Ile Gln Met Thr Gln Ser Pro Ser Ser Leu Ser Ala Ser Val
  1               5                  10                  15

Gly Asp Arg Val Thr Ile Thr Cys Arg Ala Ser Glu Ser Val Asp
             20                  25                  30

Thr Tyr Leu His Trp Tyr Gln Gln Lys Pro Gly Lys Ala Pro Lys
             35                  40                  45

Leu Leu Ile Lys Tyr Ala Ser Gln Ser Ile Ser Gly Val Pro Ser
             50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
             80                  85                  90

Gly Asn Ser Leu Pro Asn Thr Phe Gly Gln Gly Thr Lys Val Glu
             95                 100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 32
<211> LENGTH: 447
<212> TYPE: PRT
<213> ORGANISM: Artificial sequence
<220> FEATURE:
<223> OTHER INFORMATION: sequence is synthesized

<400> SEQUENCE: 32

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Phe Ile Thr
             20                  25                  30

Asn Asn Tyr Trp Gly Trp Val Arg Gln Ala Pro Gly Lys Gly Leu
             35                  40                  45

Glu Trp Val Gly Tyr Ile Ser Tyr Ser Gly Ser Thr Ser Tyr Asn
             50                  55                  60

Pro Ser Leu Lys Ser Arg Phe Thr Ile Ser Arg Asp Thr Ser Lys
 65                  70                  75

Asn Thr Phe Tyr Leu Gln Met Asn Ser Leu Arg Ala Glu Asp Thr
             80                  85                  90

Ala Val Tyr Tyr Cys Ala Met Thr Gly Ser Ser Gly Tyr Phe Asp
             95                 100                 105

Phe Trp Gly Gln Gly Thr Leu Val Thr Val Ser Ser Ala Ser Thr
            110                 115                 120

Lys Gly Pro Ser Val Phe Pro Leu Ala Pro Ser Ser Lys Ser Thr
            125                 130                 135
```

Ser Gly Gly Thr Ala Ala Leu Gly Cys Leu Val Lys Asp Tyr Phe
            140                 145                 150

Pro Glu Pro Val Thr Val Ser Trp Asn Ser Gly Ala Leu Thr Ser
            155                 160                 165

Gly Val His Thr Phe Pro Ala Val Leu Gln Ser Ser Gly Leu Tyr
            170                 175                 180

Ser Leu Ser Ser Val Val Thr Val Pro Ser Ser Ser Leu Gly Thr
            185                 190                 195

Gln Thr Tyr Ile Cys Asn Val Asn His Lys Pro Ser Asn Thr Lys
            200                 205                 210

Val Asp Lys Lys Val Glu Pro Lys Ser Cys Asp Lys Thr His Thr
            215                 220                 225

Cys Pro Pro Cys Pro Ala Pro Glu Leu Leu Gly Gly Pro Ser Val
            230                 235                 240

Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp
            260                 265                 270

Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn
            305                 310                 315

Gly Lys Glu Tyr Lys Cys Lys Val Ser Asn Lys Ala Leu Pro Ala
            320                 325                 330

Pro Ile Glu Lys Thr Ile Ser Lys Ala Lys Gly Gln Pro Arg Glu
            335                 340                 345

Pro Gln Val Tyr Thr Leu Pro Pro Ser Arg Glu Glu Met Thr Lys
            350                 355                 360

Asn Gln Val Ser Leu Thr Cys Leu Val Lys Gly Phe Tyr Pro Ser
            365                 370                 375

Asp Ile Ala Val Glu Trp Glu Ser Asn Gly Gln Pro Glu Asn Asn
            380                 385                 390

Tyr Lys Thr Thr Pro Pro Val Leu Asp Ser Asp Gly Ser Phe Phe
            395                 400                 405

Leu Tyr Ser Lys Leu Thr Val Asp Lys Ser Arg Trp Gln Gln Gly
            410                 415                 420

Asn Val Phe Ser Cys Ser Val Met His Glu Ala Leu His Asn His
            425                 430                 435

Tyr Thr Gln Lys Ser Leu Ser Leu Ser Pro Gly Lys
            440                 445

<210> SEQ ID NO 33
<211> LENGTH: 214
<212> TYPE: PRT
<213> ORGANISM: Artificial sequence
<220> FEATURE:
<223> OTHER INFORMATION: sequence is synthesized

<400> SEQUENCE: 33

Asp Ile Gln Met Thr Gln Ser Pro Ser Ser Leu Ser Ala Ser Val
 1               5                  10                  15

Gly Asp Arg Val Thr Ile Thr Cys Arg Ala Ser Glu Ser Val Asp
            20                  25                  30

```
Asp Leu Leu His Trp Tyr Gln Gln Lys Pro Gly Lys Ala Pro Lys
             35                  40                  45

Leu Leu Ile Lys Tyr Ala Ser Gln Ser Ile Ser Gly Val Pro Ser
         50                  55                  60

Arg Phe Ser Gly Ser Gly Ser Gly Thr Asp Phe Thr Leu Thr Ile
     65                  70                  75

Ser Ser Leu Gln Pro Glu Asp Phe Ala Thr Tyr Tyr Cys Gln Gln
 80                  85                  90

Gly Asn Ser Leu Pro Asn Thr Phe Gly Gln Gly Thr Lys Val Glu
             95                 100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 34
<211> LENGTH: 23
<212> TYPE: PRT
<213> ORGANISM: Artificial sequence
<220> FEATURE:
<223> OTHER INFORMATION: sequence is synthesized

<400> SEQUENCE: 34

Asp Ile Gln Met Thr Gln Ser Pro Ser Ser Leu Ser Ala Ser Val
  1               5                  10                  15

Gly Asp Arg Val Thr Ile Thr Cys
                 20

<210> SEQ ID NO 35
<211> LENGTH: 14
<212> TYPE: PRT
<213> ORGANISM: Artificial sequence
<220> FEATURE:
<223> OTHER INFORMATION: sequence is synthesized

<400> SEQUENCE: 35

Trp Tyr Gln Gln Lys Pro Gly Lys Ala Pro Lys Leu Leu Ile
  1               5                  10

<210> SEQ ID NO 36
<211> LENGTH: 32
<212> TYPE: PRT
<213> ORGANISM: Artificial sequence
<220> FEATURE:
<223> OTHER INFORMATION: sequence is synthesized

<400> SEQUENCE: 36

Gly Val Pro Ser Arg Phe Ser Gly Ser Gly Ser Gly Thr Asp Phe
  1               5                  10                  15
```

```
Thr Leu Thr Ile Ser Ser Leu Gln Pro Glu Asp Phe Ala Thr Tyr
            20                  25                  30

Tyr Cys

<210> SEQ ID NO 37
<211> LENGTH: 11
<212> TYPE: PRT
<213> ORGANISM: Artificial sequence
<220> FEATURE:
<223> OTHER INFORMATION: sequence is synthesized

<400> SEQUENCE: 37

Phe Gly Gln Gly Thr Lys Val Glu Ile Lys Arg
                 5                  10

<210> SEQ ID NO 38
<211> LENGTH: 25
<212> TYPE: PRT
<213> ORGANISM: Artificial sequence
<220> FEATURE:
<223> OTHER INFORMATION: sequence is synthesized

<400> SEQUENCE: 38

Glu Val Gln Leu Val Glu Ser Gly Gly Gly Leu Val Gln Pro Gly
 1               5                  10                  15

Gly Ser Leu Arg Leu Ser Cys Ala Ala Ser
            20                  25

<210> SEQ ID NO 39
<211> LENGTH: 13
<212> TYPE: PRT
<213> ORGANISM: Artificial sequence
<220> FEATURE:
<223> OTHER INFORMATION: sequence is synthesized

<400> SEQUENCE: 39

Trp Val Arg Gln Ala Pro Gly Lys Gly Leu Glu Trp Val
                 5                  10

<210> SEQ ID NO 40
<211> LENGTH: 31
<212> TYPE: PRT
<213> ORGANISM: Artificial sequence
<220> FEATURE:
<223> OTHER INFORMATION: sequence is synthesized

<400> SEQUENCE: 40

Arg Phe Thr Ile Ser Arg Asp Asn Ser Lys Asn Thr Leu Tyr Leu
 1               5                  10                  15

Gln Met Asn Ser Leu Arg Ala Glu Asp Thr Ala Val Tyr Tyr Cys
            20                  25                  30

Ala

<210> SEQ ID NO 41
<211> LENGTH: 11
<212> TYPE: PRT
<213> ORGANISM: Artificial sequence
<220> FEATURE:
<223> OTHER INFORMATION: sequence is synthesized

<400> SEQUENCE: 41

Trp Gly Gln Gly Thr Leu Val Thr Val Ser Ser
                 5                  10

<210> SEQ ID NO 42
```

```
<211> LENGTH: 31
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 6
<223> OTHER INFORMATION: Unknown amino acid
<220> FEATURE:
<221> NAME/KEY: Unsure
<222> LOCATION: 8
<223> OTHER INFORMATION: Unknown amino acid
<220> FEATURE:
<221> NAME/KEY: Unsure
<222> LOCATION: 13
<223> OTHER INFORMATION: Unknown amino acid

<400> SEQUENCE: 42

Arg Phe Thr Ile Ser Xaa Asp Xaa Ser Lys Asn Thr Xaa Tyr Leu
 1               5                  10                  15

Gln Met Asn Ser Leu Arg Ala Glu Asp Thr Ala Val Tyr Tyr Cys
                20                  25                  30

Ala

<210> SEQ ID NO 43
<211> LENGTH: 31
<212> TYPE: PRT
<213> ORGANISM: Artificial sequence
<220> FEATURE:
<223> OTHER INFORMATION: sequence is synthesized

<400> SEQUENCE: 43

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

Ala

<210> SEQ ID NO 44
<211> LENGTH: 31
<212> TYPE: PRT
<213> ORGANISM: Artificial sequence
<220> FEATURE:
<223> OTHER INFORMATION: sequence is synthesized

<400> SEQUENCE: 44

Arg Phe Thr Ile Ser Arg Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

Ala

<210> SEQ ID NO 45
<211> LENGTH: 31
<212> TYPE: PRT
<213> ORGANISM: Artificial sequence
<220> FEATURE:
<223> OTHER INFORMATION: sequence is synthesized

<400> SEQUENCE: 45

Arg Phe Thr Ile Ser Arg Asp Thr Ser Lys Asn Thr Phe Tyr Leu
 1               5                  10                  15

Gln Met Asn Ser Leu Arg Ala Glu Asp Thr Ala Val Tyr Tyr Cys
                20                  25                  30
```

Ala

<210> SEQ ID NO 46
<211> LENGTH: 31
<212> TYPE: PRT
<213> ORGANISM: Artificial sequence
<220> FEATURE:
<223> OTHER INFORMATION: sequence is synthesized

<400> SEQUENCE: 46

Arg Phe Thr Ile Ser Ala Asp Thr Ser Lys Asn Thr Phe Tyr Leu
 1               5                  10                  15

Gln Met Asn Ser Leu Arg Ala Glu Asp Thr Ala Val Tyr Tyr Cys
                20                  25                  30

Ala

<210> SEQ ID NO 47
<211> LENGTH: 10
<212> TYPE: PRT
<213> ORGANISM: Artificial sequence
<220> FEATURE:
<223> OTHER INFORMATION: sequence is synthesized

<400> SEQUENCE: 47

Ala Ser Glu Ser Val Asp Asp Leu Leu His
 1               5                  10

<210> SEQ ID NO 48
<211> LENGTH: 87
<212> TYPE: PRT
<213> ORGANISM: Artificial sequence
<220> FEATURE:
<223> OTHER INFORMATION: sequence is synthesized

<400> SEQUENCE: 48

Gln Val Gln Leu Gln Glu Ser Gly Pro Gly Leu Val Lys Pro Ser
 1               5                  10                  15

Gln Thr Leu Ser Leu Thr Cys Thr Val Ser Gly Gly Ser Val Ser
                20                  25                  30

Trp Ile Arg Gln Pro Pro Gly Lys Gly Leu Glu Trp Ile Gly Arg
                35                  40                  45

Val Thr Ile Ser Val Asp Thr Ser Lys Asn Gln Phe Ser Leu Lys
                50                  55                  60

Leu Ser Ser Val Thr Ala Ala Asp Thr Ala Val Tyr Tyr Cys Ala
                65                  70                  75

Arg Trp Gly Gln Gly Thr Leu Val Thr Val Ser Ser
                80                  85

<210> SEQ ID NO 49
<211> LENGTH: 81
<212> TYPE: PRT
<213> ORGANISM: Artificial sequence
<220> FEATURE:
<223> OTHER INFORMATION: sequence is synthesized

<400> SEQUENCE: 49

Gln Val Gln Leu Gln Glu Ser Gly Pro Gly Leu Val Lys Pro Ser
 1               5                  10                  15

Gln Thr Leu Ser Leu Thr Cys Thr Val Ser Trp Ile Arg Gln Pro
                20                  25                  30

Pro Gly Lys Gly Leu Glu Trp Ile Arg Val Thr Ile Ser Val Asp
                35                  40                  45

```
Thr Ser Lys Asn Gln Phe Ser Leu Lys Leu Ser Ser Val Thr Ala
            50                  55                  60

Ala Asp Thr Ala Val Tyr Tyr Cys Ala Arg Trp Gly Gln Gly Thr
65                  70                  75

Leu Val Thr Val Ser Ser
            80

<210> SEQ ID NO 50
<211> LENGTH: 80
<212> TYPE: PRT
<213> ORGANISM: Artificial sequence
<220> FEATURE:
<223> OTHER INFORMATION: sequence is synthesized

<400> SEQUENCE: 50

Gln Val Gln Leu Gln Glu Ser Gly Pro Gly Leu Val Lys Pro Ser
1               5                   10                  15

Gln Thr Leu Ser Leu Thr Cys Thr Val Ser Trp Ile Arg Gln Pro
            20                  25                  30

Pro Gly Lys Gly Leu Glu Trp Ile Arg Val Thr Ile Ser Val Asp
        35                  40                  45

Thr Ser Lys Asn Gln Phe Ser Leu Lys Leu Ser Ser Val Thr Ala
            50                  55                  60

Ala Asp Thr Ala Val Tyr Tyr Cys Ala Trp Gly Gln Gly Thr Leu
65                  70                  75

Val Thr Val Ser Ser
            80

<210> SEQ ID NO 51
<211> LENGTH: 79
<212> TYPE: PRT
<213> ORGANISM: Artificial sequence
<220> FEATURE:
<223> OTHER INFORMATION: sequence is synthesized

<400> SEQUENCE: 51

Gln Val Gln Leu Gln Glu Ser Gly Pro Gly Leu Val Lys Pro Ser
1               5                   10                  15

Gln Thr Leu Ser Leu Thr Cys Thr Val Ser Trp Ile Arg Gln Pro
            20                  25                  30

Pro Gly Lys Gly Leu Glu Trp Ile Arg Val Thr Ile Ser Val Asp
        35                  40                  45

Thr Ser Lys Asn Gln Phe Ser Leu Lys Leu Ser Ser Val Thr Ala
            50                  55                  60

Ala Asp Thr Ala Val Tyr Tyr Cys Trp Gly Gln Gly Thr Leu Val
65                  70                  75

Thr Val Ser Ser

<210> SEQ ID NO 52
<211> LENGTH: 87
<212> TYPE: PRT
<213> ORGANISM: Artificial sequence
<220> FEATURE:
<223> OTHER INFORMATION: sequence is synthesized

<400> SEQUENCE: 52

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
            20                  25                  30
```

```
Trp Val Arg Gln Ala Pro Gly Lys Gly Leu Glu Trp Val Ser Arg
             35                  40                  45

Phe Thr Ile Ser Arg Asp Asn Ser Lys Asn Thr Leu Tyr Leu Gln
         50                  55                  60

Met Asn Ser Leu Arg Ala Glu Asp Thr Ala Val Tyr Tyr Cys Ala
 65                  70                  75

Arg Trp Gly Gln Gly Thr Leu Val Thr Val Ser Ser
                 80                  85
```

```
<210> SEQ ID NO 53
<211> LENGTH: 81
<212> TYPE: PRT
<213> ORGANISM: Artificial sequence
<220> FEATURE:
<223> OTHER INFORMATION: sequence is synthesized

<400> SEQUENCE: 53

Glu Val Gln Leu Val Glu Ser Gly Gly Gly Leu Val Gln Pro Gly
  1               5                  10                  15

Gly Ser Leu Arg Leu Ser Cys Ala Ala Ser Trp Val Arg Gln Ala
                 20                  25                  30

Pro Gly Lys Gly Leu Glu Trp Val Arg Phe Thr Ile Ser Arg Asp
             35                  40                  45

Asn Ser Lys Asn Thr Leu Tyr Leu Gln Met Asn Ser Leu Arg Ala
         50                  55                  60

Glu Asp Thr Ala Val Tyr Tyr Cys Ala Arg Trp Gly Gln Gly Thr
 65                  70                  75

Leu Val Thr Val Ser Ser
                 80
```

```
<210> SEQ ID NO 54
<211> LENGTH: 80
<212> TYPE: PRT
<213> ORGANISM: Artificial sequence
<220> FEATURE:
<223> OTHER INFORMATION: sequence is synthesized

<400> SEQUENCE: 54

Glu Val Gln Leu Val Glu Ser Gly Gly Gly Leu Val Gln Pro Gly
  1               5                  10                  15

Gly Ser Leu Arg Leu Ser Cys Ala Ala Ser Trp Val Arg Gln Ala
                 20                  25                  30

Pro Gly Lys Gly Leu Glu Trp Val Arg Phe Thr Ile Ser Arg Asp
             35                  40                  45

Asn Ser Lys Asn Thr Leu Tyr Leu Gln Met Asn Ser Leu Arg Ala
         50                  55                  60

Glu Asp Thr Ala Val Tyr Tyr Cys Ala Trp Gly Gln Gly Thr Leu
 65                  70                  75

Val Thr Val Ser Ser
                 80
```

```
<210> SEQ ID NO 55
<211> LENGTH: 79
<212> TYPE: PRT
<213> ORGANISM: Artificial sequence
<220> FEATURE:
<223> OTHER INFORMATION: sequence is synthesized

<400> SEQUENCE: 55

Glu Val Gln Leu Val Glu Ser Gly Gly Gly Leu Val Gln Pro Gly
  1               5                  10                  15
```

```
Gly Ser Leu Arg Leu Ser Cys Ala Ala Ser Trp Val Arg Gln Ala
            20                  25                  30

Pro Gly Lys Gly Leu Glu Trp Val Arg Phe Thr Ile Ser Arg Asp
            35                  40                  45

Asn Ser Lys Asn Thr Leu Tyr Leu Gln Met Asn Ser Leu Arg Ala
            50                  55                  60

Glu Asp Thr Ala Val Tyr Tyr Cys Trp Gly Gln Gly Thr Leu Val
            65                  70                  75

Thr Val Ser Ser

<210> SEQ ID NO 56
<211> LENGTH: 87
<212> TYPE: PRT
<213> ORGANISM: Artificial sequence
<220> FEATURE:
<223> OTHER INFORMATION: sequence is synthesized

<400> SEQUENCE: 56

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
            20                  25                  30

Trp Val Arg Gln Ala Pro Gly Lys Gly Leu Glu Trp Val Ser Arg
            35                  40                  45

Phe Thr Ile Ser Ala Asp Thr Ser Lys Asn Thr Ala Tyr Leu Gln
            50                  55                  60

Met Asn Ser Leu Arg Ala Glu Asp Thr Ala Val Tyr Tyr Cys Ser
            65                  70                  75

Arg Trp Gly Gln Gly Thr Leu Val Thr Val Ser Ser
            80                  85

<210> SEQ ID NO 57
<211> LENGTH: 81
<212> TYPE: PRT
<213> ORGANISM: Artificial sequence
<220> FEATURE:
<223> OTHER INFORMATION: sequence is synthesized

<400> SEQUENCE: 57

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
            20                  25                  30

Pro Gly Lys Gly Leu Glu Trp Val Arg Phe Thr Ile Ser Ala Asp
            35                  40                  45

Thr Ser Lys Asn Thr Ala Tyr Leu Gln Met Asn Ser Leu Arg Ala
            50                  55                  60

Glu Asp Thr Ala Val Tyr Tyr Cys Ser Arg Trp Gly Gln Gly Thr
            65                  70                  75

Leu Val Thr Val Ser Ser
            80

<210> SEQ ID NO 58
<211> LENGTH: 80
<212> TYPE: PRT
<213> ORGANISM: Artificial sequence
<220> FEATURE:
<223> OTHER INFORMATION: sequence is synthesized

<400> SEQUENCE: 58
```

-continued

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
            20                  25                  30

Pro Gly Lys Gly Leu Glu Trp Val Arg Phe Thr Ile Ser Ala Asp
        35                  40                  45

Thr Ser Lys Asn Thr Ala Tyr Leu Gln Met Asn Ser Leu Arg Ala
    50                  55                  60

Glu Asp Thr Ala Val Tyr Tyr Cys Ser Trp Gly Gln Gly Thr Leu
65                  70                  75

Val Thr Val Ser Ser
            80

<210> SEQ ID NO 59
<211> LENGTH: 87
<212> TYPE: PRT
<213> ORGANISM: Artificial sequence
<220> FEATURE:
<223> OTHER INFORMATION: sequence is synthesized

<400> SEQUENCE: 59

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
            20                  25                  30

Trp Val Arg Gln Ala Pro Gly Lys Gly Leu Glu Trp Val Ser Arg
        35                  40                  45

Phe Thr Ile Ser Ala Asp Thr Ser Lys Asn Thr Ala Tyr Leu Gln
    50                  55                  60

Met Asn Ser Leu Arg Ala Glu Asp Thr Ala Val Tyr Tyr Cys Ala
65                  70                  75

Arg Trp Gly Gln Gly Thr Leu Val Thr Val Ser Ser
            80                  85

<210> SEQ ID NO 60
<211> LENGTH: 81
<212> TYPE: PRT
<213> ORGANISM: Artificial sequence
<220> FEATURE:
<223> OTHER INFORMATION: sequence is synthesized

<400> SEQUENCE: 60

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
            20                  25                  30

Pro Gly Lys Gly Leu Glu Trp Val Arg Phe Thr Ile Ser Ala Asp
        35                  40                  45

Thr Ser Lys Asn Thr Ala Tyr Leu Gln Met Asn Ser Leu Arg Ala
    50                  55                  60

Glu Asp Thr Ala Val Tyr Tyr Cys Ala Arg Trp Gly Gln Gly Thr
65                  70                  75

Leu Val Thr Val Ser Ser
            80

<210> SEQ ID NO 61
<211> LENGTH: 80
<212> TYPE: PRT
<213> ORGANISM: Artificial sequence
<220> FEATURE:
<223> OTHER INFORMATION: sequence is synthesized

<400> SEQUENCE: 61

```
Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
             20                  25                  30

Pro Gly Lys Gly Leu Glu Trp Val Arg Phe Thr Ile Ser Ala Asp
         35                  40                  45

Thr Ser Lys Asn Thr Ala Tyr Leu Gln Met Asn Ser Leu Arg Ala
     50                  55                  60

Glu Asp Thr Ala Val Tyr Tyr Cys Ala Trp Gly Gln Gly Thr Leu
 65                  70                  75

Val Thr Val Ser Ser
             80
```

<210> SEQ ID NO 62
<211> LENGTH: 79
<212> TYPE: PRT
<213> ORGANISM: Artificial sequence
<220> FEATURE:
<223> OTHER INFORMATION: sequence is synthesized

<400> SEQUENCE: 62

```
Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
             20                  25                  30

Pro Gly Lys Gly Leu Glu Trp Val Arg Phe Thr Ile Ser Ala Asp
         35                  40                  45

Thr Ser Lys Asn Thr Ala Tyr Leu Gln Met Asn Ser Leu Arg Ala
     50                  55                  60

Glu Asp Thr Ala Val Tyr Tyr Cys Trp Gly Gln Gly Thr Leu Val
 65                  70                  75

Thr Val Ser Ser
```

<210> SEQ ID NO 63
<211> LENGTH: 11
<212> TYPE: PRT
<213> ORGANISM: Artificial sequence
<220> FEATURE:
<223> OTHER INFORMATION: sequence is synthesized

<400> SEQUENCE: 63

```
Ala Met Thr Gly Ser Ser Gly Tyr Phe Asp Phe
                 5                  10
```

<210> SEQ ID NO 64
<211> LENGTH: 11
<212> TYPE: PRT
<213> ORGANISM: Artificial sequence
<220> FEATURE:
<223> OTHER INFORMATION: sequence is synthesized

<400> SEQUENCE: 64

```
Ala Arg Thr Gly Ser Ser Gly Tyr Phe Asp Phe
                 5                  10
```

<210> SEQ ID NO 65
<211> LENGTH: 11
<212> TYPE: PRT

```
<213> ORGANISM: Artificial sequence
<220> FEATURE:
<223> OTHER INFORMATION: sequence is synthesized

<400> SEQUENCE: 65

Ala Gln Thr Gly Ser Ser Gly Tyr Phe Asp Phe
                  5                   10

<210> SEQ ID NO 66
<211> LENGTH: 10
<212> TYPE: PRT
<213> ORGANISM: Artificial sequence
<220> FEATURE:
<223> OTHER INFORMATION: sequence is synthesized

<400> SEQUENCE: 66

Arg Thr Gly Ser Ser Gly Tyr Phe Asp Phe
              5                   10

<210> SEQ ID NO 67
<211> LENGTH: 8
<212> TYPE: PRT
<213> ORGANISM: Artificial sequence
<220> FEATURE:
<223> OTHER INFORMATION: sequence is synthesized

<400> SEQUENCE: 67

Arg Tyr Ala Ser Gln Ser Ile Ser
                  5

<210> SEQ ID NO 68
<211> LENGTH: 8
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 1
<223> OTHER INFORMATION: Unknown amino acid

<400> SEQUENCE: 68

Xaa Tyr Ala Ser Gln Ser Ile Ser
                  5
```

HUMANIZED ANTI-BETA7 ANTAGONISTS AND USES THEREFOR

RELATED APPLICATIONS

This is a divisional application of U.S. patent application Ser. No. 11/219,121 filed Sep. 2, 2005, now U.S. Pat. No. 7,528,236, which claims the benefit under 35 U.S.C. §119(e) to U.S. Provisional Application Ser. No. 60/607,377, filed Sep. 3, 2004, the entire contents of which is hereby incorporated by reference.

TECHNICAL FIELD

The present invention relates generally to the fields of molecular biology and growth factor regulation. More specifically, the invention concerns modulators of the biological activity of integrins containing the beta7 subunit, and uses of said modulators.

BACKGROUND

The integrins are α/β heterodimeric cell surface receptors involved in numerous cellular processes from cell adhesion to gene regulation (Hynes, R. O., Cell, 1992, 69:11-25; and Hemler, M. E., Annu. Rev. Immunol., 1990, 8:365-368). Several integrins have been implicated in disease processes and have generated widespread interest as potential targets for drug discovery (Sharar, S. R. et al., Springer Semin. Immunopathol., 1995, 16:359-378). In the immune system, integrins are involved in leukocyte trafficking, adhesion and infiltration during inflammatory processes (Nakajima, H. et al., J. Exp. Med., 1994, 179:1145-1154). Differential expression of integrins regulates the adhesive properties of cells and different integrins are involved in different inflammatory responses. Butcher, E. C. et al., Science, 1996, 272:60-66. The beta7 integrins (i.e. alpha4beta7 (α4β7) and alphaEbeta7 (αEβ7)) are expressed primarily on monocytes, lymphocytes, eosinophils, basophils, and macrophages but not on neutrophils. Elices, M. J. et al., Cell, 1990, 60:577-584. The primary ligands for α4β7 integrin are the endothelial surface proteins mucosal addressin cell adhesion molecule (MAdCAM) and vascular cell adhesion molecule (VCAM-1) (Makarem, R. et al., J. Biol. Chem., 1994, 269:4005-4011). The binding of the α4β7 to MAdCAM and/or VCAM expressed on high endothelial venules (HEVs) at sites of inflammation results in firm adhesion of the leukocyte to the endothelium followed by extravasation into the inflamed tissue (Chuluyan, H. E. et al., Springer Semin. Immunopathol., 1995, 16:391-404). A primary ligand for αEβ7 integrin is the intra-epithelial lymphocyte (IEL) surface protein, E-cadherein, which facilitates adherence of the αEβ7-bearing cell to epithelial lymphocytes. Monoclonal antibodies directed against α4β7, MAdCAM or VCAM have been shown to be effective modulators in animal models of chronic inflammatory diseases such as asthma (Laberge, S. et al., Am. J. Respir. Crit. Care Med., 1995, 151:822-829.), rheumatoid arthritis (RA; Barbadillo, C. et al., Springer Semin. Immunopathol., 1995, 16:375-379), colitis (Viney et al, J. Immunol., 1996, 157: 2488-2497) and inflammatory bowel diseases (IBD; Podalski, D. K., N. Eng. J. Med., 1991, 325:928-937; Powrie, F. et al., Ther. Immunol., 1995, 2:115-123). Monoclonal antibodies directed against beta7 subunit have been shown to bind the integrin subunit (Tidswell, M. et al. (1997) J. Immunol. 159:1497-1505) but as non-human or non-humanized antibodies, they lack clinical usefulness.

A need exists for highly specific compounds, such as humanized antibodies or binding fragments thereof which inhibit the interaction between the alpha4beta7 integrin and its ligands MAdCAM and/or VCAM as well as the interaction between the alphaEbeta7 integrin and its ligand E-cadherin. These compounds are useful for treatment of chronic inflammatory diseases such as asthma, Crohn's disease, ulcerative colitis, diabetes, complications of organ transplantation, and allograft-related disorders.

All references cited herein, including patent applications and publications, are incorporated by reference in their entirety.

DISCLOSURE OF THE INVENTION

The invention is in part based on the identification of a variety of antagonists of biological pathways involving beta7-containing integrins, which are generally biological/cellular processes that presents as an important and advantageous therapeutic target. Such biological pathways include, without limitation, inflammation, particularly chronic inflammation disorders such as asthma, allergy, IBD, diabetes, transplantation and grafts versus host disorders. The invention provides compositions and methods based on interfering with beta7 integrin-mediated cellular adhesion and/or recruitment, including but not limited to interfering with MAdCAM and VCAM-1 binding to the extracellular portion of alpha4beta7 integrin and E-cadherin interaction with the alphaEbeta7 integrin intereaction. Antagonists of the invention, as described herein, provide important therapeutic and diagnostic agents for use in targeting pathological conditions associated with abnormal or unwanted signaling via a beta7 integrin. Accordingly, the invention provides methods, compositions, kits and articles of manufacture related to modulating beta7 integrin-mediated pathways, including modulation of MAdCAM-alpha4beta7 binding and leukocyte recruitment to gastrointestinal epithelium, binding and allergy, asthma, IBD (such as Crohn's disease and ulcerative colitis), diabetes, inflammation associated with transplantation, graft versus host disorder and/or allograft disorders and other biological/physiological activities mediated by beta7 integrin.

In one aspect, the invention provides anti-beta7 therapeutic agents suitable for therapeutic use and capable of effecting varying degrees of disruption of a beta7 integrin-mediated pathway. For example, in one embodiment, the invention provides a humanized anti-beta7 antibody wherein the antibody as a Fab fragment has substantially the same binding affinity to human beta7 as a murine Fab fragment comprising, consisting or consisting essentially of a light chain and heavy chain variable domain sequence as depicted in FIGS. 1A and 1B or FIGS. 9A and 9B. In another embodiment, the invention provides a humanized anti-beta7 antibody wherein the antibody as a Fab fragment has a binding affinity to human beta7 that is lower, for example at least 3, at least 5, at least 7 or at least 10-fold lower, than that of a murine or rat Fab fragment comprising, consisting or consisting essentially of a light chain and heavy chain variable domain sequence as depicted in FIGS. 1A and 1B or the variable domain sequences depicted in FIGS. 9A and 9B. Alternatively, a humanized anti-beta7 antibody, or beta7 binding fragment thereof, of the invention exhibits monovalent affinity to human beta7, which affinity is substantially the same as or greater than monovalent affinity to human beta7 of an antibody comprising light chain and heavy chain variable sequences as depicted in FIG. 1A (SEQ ID NO: 10) and/or FIG. 1B (SEQ ID NO:11), or FIG. 9A (SEQ ID NO: 12)

and/or FIG. 9B (SEQ ID NO: 13). The antibody or binding fragment thereof having great affinity to human beta7 exhibits an affinity which is at least 2-fold, at least 5-fold, at least 10-fold, at least 50-fold, at least 100-fold, at least 500-fold, at least 1000-fold, at least 5000-fold, or at least 10,000-fold greater than an antibody comprising the light chain and heavy chain sequences depicted in FIG. 1A (SEQ ID NO:10) and/or FIG. 1B (SEQ ID NO:11), or FIG. 9A (SEQ ID NO:12) and/or FIG. 9B (SEQ ID NO:13).

In another embodiment, the invention provides an anti-beta7 humanized antibody wherein the antibody as a Fab fragment has a binding affinity to human beta7 that is greater, for example at least 3, at least 5, at least 7, at least 9, at least 10, at least 15, at least 20, or at least 100-fold greater than that of a rodent (such as rat or murine) Fab fragment comprising, consisting or consisting essentially of a light chain and heavy chain variable domain sequence as depicted in FIG. 1A and FIG. 1B, respectively. In one embodiment, said rodent Fab fragment has the binding affinity of a Fab fragment comprising variable domain sequences of a rat antibody designated FIB504.64 produced by hybridoma cell line deposited under American Type Culture Collection Accession Number ATCC HB-293. In a further embodiment, a humanized Fab fragment of the invention has the binding affinity of a Fab fragment comprising variable domain sequences of an antibody produced by anyone of the humanized anti-beta7 antibodies of the invention. As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. As described in greater detail herein, fold difference in binding affinity can be quantified in terms of the ratio of the binding affinity value of a humanized antibody in Fab form and the binding affinity value of a reference/comparator Fab antibody (e.g., a murine antibody having donor hypervariable region sequences), wherein the binding affinity values are determined under similar assay conditions. Thus, in one embodiment, the fold difference in binding affinity is determined as the ratio of the Kd values of the humanized antibody in Fab form and said reference/comparator Fab antibody. Any of a number of assays known in the art, including those described herein, can be used to obtain binding affinity measurements, including, for example, Biacore® (Biacore International Ab, Uppsala, Sweden) and ELISA.

In its various aspects and embodiments, the beta7 antagonist antibody of the invention is directed to the following set of potential claims for this application: Antibody comprising an anti-beta7 antibody or beta7 binding fragment thereof comprising:

(a) at least one, two, three, four, or five hypervariable region (HVR) sequences selected from the group consisting of:

(i) HVR-L1 comprising sequence A1-A11, wherein A1-A11 is RASESVDTYLH (SEQ ID NO:1)
(ii) HVR-L2 comprising sequence B1-B8, wherein B1-B8 is KYASQSIS (SEQ ID NO:2)
(iii) HVR-L3 comprising sequence C1-C9, wherein C1-C9 is QQGNSLPNT (SEQ ID NO:3)
(iv) HVR-H1 comprising sequence D1-D10, wherein D1-D10 is GFFITNNYWG (SEQ ID NO:4)
(v) HVR-H2 comprising sequence E1-E17, wherein E1-E17 is GYISYSGSTSYNPSLKS (SEQ ID NO:5); and
(vi) HVR-H3 comprising sequence F2-F11, wherein F2-F11 is MTGSSGYFDF (SEQ ID NO:6).

In an embodiment of the polypeptide or antibody of claim 1, the polypeptide or antibody comprises at least one variant HVR, wherein the variant HVR sequence comprises modification of at least one residue of at least one of the sequences depicted in SEQ ID NOs:1, 2, 3, 4, 5, 6, 7, 8, and 9. In another embodiment of claim 1 or claim 2, the invention comprises an an anti-beta7 antibody or beta7 binding fragment thereof comprising one, two, three, four, five or six hypervariable regions (HVRs) selected from the group consisting of HVR-L1, HVR-L2, HVR-L3, HVR-H1, HVR-H2, and HVR-H3, wherein:

(i) HVR-L1 comprises amino acid sequence RASESVDTYLH (SEQ ID NO:1); RASESVDSLLH (SEQ ID NO:7), RASESVDTLLH (SEQ ID NO:8), or RASESVDDLLH (SEQ ID NO:9);
(ii) HVR-L2 comprises amino acid sequence KYASQSIS (SEQ ID NO:2), RYASQSIS (SEQ ID NO:67, or XYASQSIS (SEQ ID NO:68, where X represents any amino acid),
(iii) HVR-L3 comprises QQGNSLPNT (SEQ ID NO:3),
(iv) HVR-H1 comprises amino acid sequence GFFITNNYWG (SEQ ID NO:4),
(v) HVR-H2 comprises amino acid sequence GYISYSGSTSYNPSLKS (SEQ ID NO:5), and
(vi) HVR-H3 comprises amino acid sequence MTGSSGYFDF (SEQ ID NO:6) or RTGSSGYFDF (SEQ ID NO:66) for relative positions F2-F11; or comprises amino acid sequence F1-F11, wherein F1-F11 is AMTGSSGYFDF (SEQ ID NO:63), ARTGSSGYFDF (SEQ ID NO:64), or AQTGSSGYFDF (SEQ ID NO:65).

In still another embodiment of claim 1 or any of the embodiments, the invention comprises an an anti-beta7 antibody or beta7 binding fragment thereof comprising one, two, three, four, five or six hypervariable regions (HVRs) selected from the group consisting of HVR-L1, HVR-L2, HVR-L3, HVR-H1, HVR-H2, and HVR-H3, wherein:

(i) HVR-L1 comprises amino acid sequence A1-A11, wherein A1-A11 is RASESVDTYLH (SEQ ID NO:1); RASESVDSLLH (SEQ ID NO:7), RASESVDTLLH (SEQ ID NO:8), or RASESVDDLLH (SEQ ID NO:9) or a variant of SEQ ID NOs:1, 7, 8 or 9 wherein amino acid A2 is selected from the group consisting of A, G, S, T, and V and/or amino acid A3 is selected from the group consisting of S, G, I, K, N, P, Q, R, and T, and/or A4 is selected from the group consisting of E, V, Q, A, D, G, H, I, K, L, N, and R, and/or amino acid A5 is selected from the group consisting of S, Y, A, D, G, H, I, K, N, P, R, T, and V, and/or amino acid A6 is selected from the group consisting of V, R, I, A, G, K, L, M, and Q, and/or amino acid A7 is selected from the group consisting of D, V, S, A, E, G, H, I, K, L, N, P, S, and T, and/or amino acid A8 is selected from the group consisting of D, G, N, E, T, P and S, and/or amino acid A9 is selected from the group consisting of L, Y, I and M, and/or amino acid A10 is selected from the group consisting of L, A, I, M, and V and/or amino acid A11 is selected from the group consisting of H, Y, F, and S;
(ii) HVR-L2 comprises amino acid sequence B1-B8, wherein B1-B8 is KYASQSIS (SEQ ID NO:2), RYASQSIS (SEQ ID NO:67, or XYASQSIS (SEQ ID NO:68, where X represents any amino acid) or a variant of SEQ ID NOs:2, 67 or 68 wherein amino acid B1 is selected from the group consisting of K, R, N, V, A, F, Q, H, P, I, L, Y and X (where X represents any amino acid), and/or amino acid B4 is selected from the group consisting of S and D, and/or amino acid B5 is selected from the group consisting of Q and S, and/or amino acid B6 is selected from the group consisting of S, D, L, and R, and/or amino acid B7 is selected from the group consisting of I, V, E, and K;

(iii) HVR-L3 comprises amino acid sequence C1-C9, wherein C1-C9 is QQGNSLPNT (SEQ ID NO:3) or a variant of SEQ ID NO:3 wherein amino acid C8 is selected from the group consisting of N, V, W, Y, R, S, T, A, F, H, I, L, M, and Y;

(iv) HVR-H1 comprises amino acid sequence D1-D10 wherein D1-D10 is GFFITNNYWG (SEQ ID NO:4), (v) HVR-H2 comprises amino acid sequence E1-E17 wherein E1-E17 is GYISYSGSTSYNPSLKS (SEQ ID NO:5), or a variant of SEQ ID NO:5 wherein amino acid E2 is selected from the group consisting of Y, F, V, and D, and/or amino acid E6 is selected from the group consisting of S and G, and/or amino acid E10 is selected from the group consisting of S and Y, and/or amino acid E12 is selected from the group consisting of N, T, A, and D, and/or amino acid 13 is selected from the group consisting of P, H, D, and A, and/or amino acid E15 is selected from the group consisting of L and V, and/or amino acid E17 is selected from the group consisting of S and G, and (vi) HVR-H3 comprises amino acid sequence F2-F11 wherein F2-F11 is MTGSSGYFDF (SEQ ID NO:6) or RTGSSGYFDF (SEQ ID NO:66); or comprises amino acid sequence F1-F11, wherein F1-F11 is AMTGSSGYFDF (SEQ ID NO:63), ARTGSSGYFDF (SEQ ID NO:64), or AQTGSSGYFDF (SEQ ID NO:65), or a variant of SEQ ID NOs:6, 63, 64, 65, or 66 wherein amino acid F2 is R, M, A, E, G, Q, S, and/or amino acid F11 is selected from the group consisting of F and Y.

In one embodiment of claim 1 or any of the antibodies of the invention, the amino acid at heavy chain framework position 71 (according to the Kabat numbering system) is selected from the group consisting of R, A, and T, and/or the amino acid at heavy chain framework position 73 (Kabat numbering system) is selected from the group consisting of N and T, and/or the amino acid at heavy chain framework position 78 (Kabat numbering system) is selected from the group consisting of F, A, and L.

In one embodiment of claim 1 or any of the antibodies of the invention, HVR-L1 of an antibody of the invention comprises the sequence of SEQ ID NO:1. In one embodiment, HVR-L2 of an antibody of the invention comprises the sequence of SEQ ID NO:2. In one embodiment, HVR-L3 of an antibody of the invention comprises the sequence of SEQ ID NO:3. In one embodiment, HVR-H1 of an antibody of the invention comprises the sequence of SEQ ID NO:4. In one embodiment, HVR-H2 of an antibody of the invention comprises the sequence of SEQ ID NO:5. In one embodiment, HVR-H3 of an antibody of the invention comprises the sequence of SEQ ID NOs:6 or 66 for relative positions F2-F11 or SEQ ID NOs:63, 64, or 65 for relative positions F1-F11. In one embodiment, HVR-L1 comprises RASESVDSLLH (SEQ ID NO: 7). In one embodiment, HVR-L1 comprises RASESVDTLLH (SEQ ID NO: 8). In one embodiment, HVR-L1 comprises RASESVDDLLH (SEQ ID NO:9). In one embodiment, an antibody of the invention comprising these sequences (in combinations as described herein) is humanized or human.

In one aspect, the invention provides an antibody comprising one, two, three, four, five or six HVRs, wherein each HVR comprises, consists or consists essentially of a sequence selected from the group consisting of SEQ ID NOs:1, 2, 3, 4, 5, 6, 7, 8 and 9, and wherein SEQ ID NO:1, 7, 8 or 9 corresponds to an HVR-L1, SEQ ID NO:2 corresponds to an HVR-L2, SEQ ID NO:3 corresponds to an HVR-L3, SEQ ID NO:4 corresponds to an HVR-H1, SEQ ID NO:5 corresponds to an HVR-H2, and SEQ ID NOs:6 corresponds to an HVR-H3. In one embodiment, an antibody of the invention comprises HVR-L1, HVR-L2, HVR-L3, HVR-H1, HVR-H2, and HVR-H3, wherein each, in order, comprises SEQ ID NO:1, 2, 3, 4, 5 and 6. In one embodiment, an antibody of the invention comprises HVR-L1, HVR-L2, HVR-L3, HVR-Hi, HVR-H2, and HVR-H3, wherein each, in order, comprises SEQ ID NO:7, 2, 3, 4, 5 and 6. In one embodiment, an antibody of the invention comprises HVR-L1, HVR-L2, HVR-L3, HVR-H1, HVR-H2, and HVR-H3, wherein each, in order, comprises SEQ ID NO:8, 2, 3, 4, 5 and 6. In one embodiment, an antibody of the invention comprises HVR-L1, HVR-L2, HVR-L3, HVR-H1, HVR-H2, and HVR-H3, wherein each, in order, comprises SEQ ID NO:9, 2, 3, 4, 5 and 6. In one embodiment, an antibody of the invention comprises HVR-L1, HVR-L2, HVR-L3, HVR-H1, HVR-H2, and HVR-H3, wherein each, in order, comprises SEQ ID NO:9, 2, 3, 4, 5 and 66, or SEQ ID NO:9, 2, 3, 4, 5, 63 or SEQ ID NO:9, 2, 3, 4, 5, 64 or SEQ ID NO:9, 2, 3, 4, 5, and 65 or SEQ ID NO:9, 67, 3, 4, 5, 64 or SEQ ID NO:9, 68, 3, 4, 5, 64.

Variant HVRs in an antibody of the invention can have modifications of one or more residues within the HVR and the HVRs and/or framework regions may be humanized. Embodiments of the invention in which there is an HVR and/or framework modification include, without limitation, the following potential claims for this application:

2. The antibody of claim 1 or any of its embodiments, wherein A8 in a variant HVR-L1 is S, D or T and A9 is L.

3. The antibody of claim 1 or any of its embodiments, wherein the antibody is humanized.

4. The antibody of claim 1 or any of its embodiments, wherein at least a portion of the framework sequence is a human consensus framework sequence.

5. The antibody of claim 1 or any of its embodiments, wherein said modification is substitution, insertion or deletion.

6. The antibody of claim 1 or any of its embodiments, wherein a HVR-L1 variant comprises 1-10 (1, 2, 3, 4, 5, 6, 7, 8, 9, or 10) substitutions in any combination of the following positions: A2 (G, S, T, or V); A3 (G, I, K, N, P, Q, R, or T), A4 (A, D, G, H, I, K, L, N, Q, R, or V), A5 (A, D, G, H, I, K, N, P, R, T, V, or Y), A6 (A, G, I, K, L, M, Q, or R), A7 (A, E, G, H, I, K, L, N, P, S, T, or V), A8 (S, D, E, G, P, or N) and A9 (L, I, or M), A10 (A, I, M, or V), and A11 (F, S, or Y).

7. The antibody of claim 1 or any of its embodiments, wherein a HVR-L2 variant comprises 1-4 (1, 2, 3, or 4) substitutions in any combination of the following positions: B1 (N), B5 (S), B6 (R or L), and B7 (T, E, K, or V).

8. The antibody of claim 1 or any of its embodiments, wherein a HVR-L3 variant comprises at least one substitution at position C8 (W, Y, R, S, A, F, H, I, L, M, N, T, or V).

9. The antibody of claim 1 or any of its embodiments, wherein a HVR-H2 variant comprises 1-7 (1, 2, 3, 4, 5, 6, or 7) substitutions in any combination of the following positions: E2 (V, D, or F), E6 (G), E10 (Y), E12 (A, D, or T), E13 (D, A, or H), E15 (V), E17 (G).

10. The antibody of claim 1 or any of its embodiments, wherein a HVR-H3 variant comprises at 1 or 2 substitutions in any combination of the following positions: F2 (A, E, G, Q, R, or S), and F11 (Y).

11. The antibody of claim 1 or any of its embodiments, comprising an HVR-L1 having the sequence of SEQ ID NO:7.
12. The antibody of claim 1 or any of its embodiments, comprising an HVR-L1 having the sequence of SEQ ID NO:8.
13. The antibody of claim 1 or any of its embodiments, comprising an HVR-L1 having the sequence of SEQ ID NO:9.
14. The antibody of any one of claims 11-13 comprising a heavy chain human subgroup III heavy chain consensus framework sequence comprising a substitution at position 71, 73 and/or 78.
15. The antibody of claim 14, wherein the substitution is R71A, N73T and/or N78A.
16. The antibody of claim 1 or any of its embodiments, comprising an HVR-L3 having the sequence of SEQ ID NO:3.
17. The antibody of claim 1 or any of its embodiments, wherein A8 in a variant HVR-L1 is S.
18. The antibody of claim 1 or any of its embodiments, wherein A8 in a variant HVR-L1 is D.
19. The antibody of claim 1 or any of its embodiments, wherein A9 in a variant HVR-L1 is L.
20. The antibody of claim 1 or any of its embodiments, wherein a framework sequence between sequence E1-E17 and F1-F11 is HFR3-1-HFR3-31 and wherein HFR3-6 is A or R, HFR3-8 is N or T, and HFR3-13 is L or A or F.
21. A humanized anti-beta7 antibody wherein monovalent affinity of the antibody to human beta7 is substantially the same as monovalent affinity of a rat antibody comprising a light chain and heavy chain variable sequence as depicted in FIG. 9.
22. A humanized anti-beta7 antibody wherein monovalent affinity of the antibody to human beta7 is at least 3-fold greater than monovalent affinity of a rat antibody comprising a light chain and heavy chain variable sequence as depicted in FIG. 9.
23. The humanized antibody of claim 21 or 22 wherein the rat antibody is produced by hybridoma cell line deposited under American Type Culture Collection Accession Number ATCC with designation HB-293.
24. The antibody of any of claims 21-23 wherein the binding affinity is expressed as a Kd value.
25. The antibody of any of claim 21-24 wherein the binding affinity is measured by Biacore™ or radioimmunoassay.
26. The antibody of claim 1 comprising human κ subgroup 1 light chain consensus framework sequence.
27. The antibody of claim 1 comprising heavy chain human subgroup III heavy chain consensus framework sequence.
28. The antibody of claim 27 wherein the framework sequence comprises a substitution at position 71, 73 and/or 78.
29. The antibody of claim 28 wherein said substitution is R71A, N73T and/or N78A or wherein the substituted amino acid at position 71 is R or A, and/or the amino acid substitution at position 78 is N or T, and/or the amino acid substitution at position 78 is L or A or F.
30. The antibody of claim 28 wherein said substitution is L78F or A78F or A78L or L78A.
31. A method of inhibiting the interaction of a human beta7 integrin subunit with a second integrin subunit and/or a ligand by contacting the antibody of any one of claims 1-30 with the second integrin subunit and/or the ligand.
32. The method of claim 31, wherein the second integrin subunit is alpha4 integrin subunit, and wherein the ligand is MAdCAM, VCAM or fibronectin.
33. The method of claim 32, wherein the alpha4 integrin subunit is human.
34. The method of claim 33, wherein the ligand is human.
35. The method of claim 32, wherein the second integrin subunit is alphaE integrin subunit, and wherein the ligand is E-cadherein.
36. The method of claim 35, wherein the alphaE integrin subunit is human.
37. The method of claim 36, wherein the ligand is human.
38. The method of claim 31, wherein the inhibiting reduces or alleviates symptoms of a disorder selected from inflammation, asthma, inflammatory bowel disease, Crohn's disease, ulcerative colitis, diabetes, inflammation resulting of organ transplantation, graft versus host disorder, and inflammation associated with allograft disorders.

Further embodiments of the invention include without limitation the following:

In one embodiment, a HVR-L1 is SEQ ID NO:1, 7, 8, or 9 or a HVR-L1 variant of SEQ ID NO:1, 7, 8, or 9 which comprises 1-10 (1, 2, 3, 4, 5, 6, 7, 8, 9, or 10) substitutions at relative positions A1-A11, in any combination of the following positions: A2 (A, G, S, T, or V); A3 (S, G, I, K, N, P, Q, R, or T), A4 (E, A, D, G, H, I, K, L, N, Q, R, or V), A5 (S, A, D, G, H, I, K, N, P, R, T, V, or Y), A6 (V, A, G, I, K, L, M, Q, or R), A7 (D, A, E, G, H, I, K, L, N, P, S, T, or V), A8 (T, S, D, E, G, P, or N) and A9 (Y, L, I, or M), A10 (L, A, I, M, or V), and A11 (H, F, S, or Y). In one embodiment, a HVR-L2 is SEQ ID NO:2, 67, or 68 or a HVR-L2 variant of SEQ ID NO:2, 67, or 68 which HVR-L2 variant comprises 1-4 (1, 2, 3, 4, 4 or 5) substitutions at relative positions B1-B8, in any combination of the following positions: B1 (K, R, N, V, A, F, Q, H, P, I, L, Y or X (where X represents any amino acid), B4 (S), B5 (Q or S), B6 (S, R or L), and B7 (I, T, E, K, or V). In one embodiment, a HVR-L3 is SEQ ID NO:3 or a HVR-L3 variant of SEQ ID NO:3 which comprises at least one substitution at relative positions C1-C8, such as at position C8 (W, Y, R, S, A, F, H, I, L, M, N, T, or V). In one embodiment, a HVR-H1 is SEQ ID NO:4. In one embodiment, a HVR-H2 is SEQ ID NO:5 or a HVR-H2 variant of SEQ ID NO:5 which HVR-H2 variant comprises 1-7 (1, 2, 3, 4, 5, 6, or 7) substitutions at relative positions E1-E17 in any combination of the following positions: E2 (Y, V, D, or F), E6 (S or G), E10 (S or Y), E12 (N, A, D, or T), E13 (P, D, A, or H), E15 (L or V), E17 (S or G). In one embodiment, a HVR-H3 is SEQ ID NOs:6, 63, 64, 65, or 66 or a HVR-H3 variant of SEQ ID NOs:6, 63, 64, 65, or 66 which comprises at relative positions F1-F11 for SEQ ID NOs:63, 64, and 65 or at relative positions F2-F11 for SEQ ID NOs:6 and 66, 1 or 2 substitutions in any combination of the following positions: F2 (M, A, E, G, Q, R, or S), and F11 (F or Y). Letter(s) in parenthesis following each position indicates an illustrative substitution (i.e., replacement) amino acid for a consensus or other amino acid as would be evident to one skilled in the art, suitability of other amino acids as substitution amino acids in the context described herein can be routinely assessed using techniques known in the art and/or described herein.

In one embodiment, a HVR-L1 comprises the sequence of SEQ ID NO:1. In one embodiment, A8 in a variant HVR-L1 is D. In one embodiment, A8 in a variant HVR-L1 is S. In one embodiment, A9 in a variant HVR-L1 is L. In one embodiment, A8 in a variant HVR-L1 is D and A9 in a variant HVR-L1 is L. In one embodiment, A8 in a variant HVR-L1 is S and A9 in a variant HVR-L1 is L. In some embodiments of the invention comprises these variations in the HVR-L1, the HVR-L2, HVR-L3, HVR-H1, HVR-H2, and HVR-H3 comprises or consists of or consists essentially of, in order, SEQ ID NO:2, 3, 4, 5, and 6. In some embodiments, HVR-H3 comprises or consists or consists essentially of SEQ ID NO:6 or 66 (for relative positions F2-F11) or SEQ ID NO:63 or 64 or 65 (for relative positions F1-F11).

In one embodiment, A8 in a variant HVR-L1 is I and the and A9 in a variant HVR-L1 is L, which variant further comprises the HVR-L2, HVR-L3, HVR-H1, HVR-H2, and HVR-H3, each HVR comprising, consisting of, or consist essentially of, in order, SEQ ID NO:2, 3, 4, 5, and 6.

In one embodiment, A8, A9, and A10 in a variant HVR-L1 are D, L, and V, respectively, which variant further comprises the HVR-L2, HVR-L3, HVR-H1, HVR-H2, and HVR-H3, each HVR comprising, consisting of, or consist essentially of, in order, SEQ ID NO:2, 3, 4, 5, and 6.

In one embodiment, A8 and A9 in a variant HVR-L1 are N and L, respectively, which variant further comprises the HVR-L2, HVR-L3, HVR-H1, HVR-H2, and HVR-H3, each HVR comprising, consisting of, or consist essentially of, in order, SEQ ID NO:2, 3, 4, 5, and 6.

In one embodiment, A8 and A9 in a variant HVR-L1 are P and L, respectively, and B6 and B7 in a variant HVR-L2 are R and T, respectively, which variant further comprises the HVR-L2, HVR-L3, HVR-H1, HVR-H2, and HVR-H3, each HVR comprising, consisting of, or consist essentially of, in order, SEQ ID NO:3, 4, 5, and 6.

In one embodiment, A2, A4, A8, A9, and A10 in a variant HVR-L1 are S, D, S, L, and V, respectively, which variant further comprises the HVR-L2, HVR-L3, HVR-H1, HVR-H2, and HVR-H3, each HVR comprising, consisting of, or consist essentially of, in order, SEQ ID NO:2, 3, 4, 5, and 6.

In one embodiment, A5 and A9 in a variant HVR-L1 are D and T, respectively, which variant further comprises the HVR-L2, HVR-L3, HVR-H1, HVR-H2, and HVR-H3, each HVR comprising, consisting of, or consist essentially of, in order, SEQ ID NO:2, 3, 4, 5, and 6.

In one embodiment, A5 and A9 in a variant HVR-L1 are N and L, respectively, which variant further comprises the HVR-L2, HVR-L3, HVR-H1, HVR-H2, and HVR-H3, each HVR comprising, consisting of, or consist essentially of, in order, SEQ ID NO:2, 3, 4, 5, and 6.

In one embodiment, A9 in a variant HVR-L1 is L, which variant further comprises the HVR-L2, HVR-L3, HVR-H1, HVR-H2, and HVR-H3, each HVR comprising, consisting of, or consist essentially of, in order, SEQ ID NO:2, 3, 4, 5, and 6.

In one embodiment, the antibody or anti-beta7 binding polypeptide of the invention comprises an HVR-L1, HVR-L2, HVR-L3, HVR-H1, HVR-H2, and HVR-H3, each HVR comprising, consisting of, or consisting essentially of, in order, SEQ ID NO:9, 2, 3, 4, 5, and 64. In another embodiment, each HVR comprises, consists of, or consists essentially of, in order, SEQ ID NO:9, 67, 3, 4, 5, and 64. In another embodiment, each HVR comprises, consists of, or consists essentially of, in order, SEQ ID NO:9, 68, 3, 4, 5, and 64. In another embodiment, each HVR comprises, consists of, or consists essentially of, in order, SEQ ID NO:9, 2 or 67 or 68, 3, 4, 5, and 66.

In some embodiments, said variant HVR-L1 antibody variants further comprises HVR-L2, HVR-L3, HVR-L3, HVR-H1, HVR-H2, and HVR-H3, wherein each comprises, in order, the sequence depicted in SEQ ID NOs:2 3, 4, 5, and 6. Where the antibody variant comprises HVR-L1 A8(P) and A9(L) and HVR-L2 B6(R) and B7(T), in some embodiments said HVR-L1, HVR-L2 variant further comprises HVR-L3, HVR-H1, HVR-H2, and HVR-H3, wherein each comprises, in order, the sequence depicted in SEQ ID NOs:3, 4, 5, and 6.

In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In one embodiment, an antibody of the invention comprises a HVR-L1 comprising SEQ ID NO:1. In one embodiment, a variant antibody of the invention comprises a variant HVR-L1 wherein A10 is V. In one embodiment, said variant antibody further comprises HVR-L2, HVR-L3, HVR-H1, HVR-H2 and HVR-H3, wherein each comprises, in order, the sequence depicted in SEQ ID NOs:2, 3, 4, 5 and 6. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In one embodiment, an antibody of the invention comprises a HVR-L3 comprising SEQ ID NO:3. In one embodiment, a variant antibody of the invention comprises a variant HVR-L3 wherein C8 is L. In one embodiment, said variant antibody further comprises HVR-L1, HVR-L2, HVR-H1, HVR-H2 and HVR-H3, wherein each comprises, in order, the sequence depicted in SEQ ID NOs:1, 2, 4, 5 and 6. In one embodiment, an antibody of the invention comprises a variant HVR-L3 wherein C8 is W. In one embodiment, said variant antibody further comprises HVR-L1, HVR-L2, HVR-H1, HVR-H2 and HVR-H3, wherein each comprises, in order, the sequence depicted in SEQ ID NOs:1, 2, 4, 5 and 6. In some embodiment, HVR-L1 comprises SEQ ID NO:7, 8, or 9. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In one embodiment, an antibody of the invention comprises a HVR-H3 comprising SEQ ID NO:6. In one embodiment, a variant of said antibody comprises a variant HVR-H3 wherein F1 is Q. In one embodiment, said variant antibody further comprises HVR-L1, HVR-L2, HVR-L3, HVR-H1 and HVR-H2, wherein each comprises, in order, the sequence depicted in SEQ ID NOs:1, 2, 3, 4, and 5. In one embodiment, an antibody of the invention comprises a variant HVR-H3 wherein F1 is R. In one embodiment, said variant antibody further comprises HVR-L1, HVR-L2, HVR-L3, HVR-H1 and HVR-H2, wherein each comprises, in order, the sequence depicted in SEQ ID NOs:1, 2, 3, 4, and 5. In one embodiment, HVR-L1 comprises SEQ ID NO:7, 8, or 9. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In one embodiment, an antibody of the invention comprises a HVR-L1 comprising SEQ ID NO:1. In one embodiment, the antibody comprises a variant HVR-L1 wherein A4 is Q. In one embodiment, said variant antibody further comprises HVR-L2, HVR-L3, HVR-H1, HVR-H2 and HVR-H3, wherein each comprises, in order, the sequence depicted in SEQ ID NOs:2, 3, 4, 5, and 6. In one embodiment, an antibody of the invention comprises a variant HVR-L1 wherein A6 is I. In one embodiment, said variant antibody further comprises HVR-L2, HVR-L3, HVR-H1, HVR-H2 and HVR-H3, wherein each comprises, in order, the sequence depicted in SEQ ID NOs:2, 3, 4, 5, and 6. In one embodiment, an antibody of the invention comprises a variant HVR-L1 wherein A7 is S. In one embodiment, said variant antibody further comprises HVR-L2, HVR-L3, HVR-H1, HVR-H2 and HVR-H3, wherein each comprises, in order, the sequence depicted in SEQ ID NOs:2, 3, 4, 5, and 6. In one embodiment, an antibody of the invention comprises a variant HVR-L1 wherein A8 is D or N. In one embodiment, said variant antibody further comprises HVR-L2, HVR-L3, HVR-Hi, HVR-H2 and HVR-H3, wherein each comprises, in order, the sequence depicted in SEQ ID NOs:2, 3, 4, 5, and 6. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In one embodiment, an antibody of the invention comprises a HVR-L2 comprising SEQ ID NO:2. In one embodiment, an antibody of the invention comprises a variant HVR-L2 wherein BI is N. In one embodiment, an antibody of the invention comprises a variant HVR-L2 wherein B5 is S. In one embodiment, an antibody of the invention comprises a variant HVR-L2 wherein B6 is L. In one embodiment, an antibody of the invention comprises a variant HVR-L2 wherein B7 is V. In one embodiment, an antibody of the invention comprises a variant HVR-L2 wherein B7 is E or K. In some embodiments, said variant antibody further comprises HVR-L1, HVR-L3, HVR-H1, HVR-H2 and HVR-H3, wherein each comprises, in order, the sequence depicted in SEQ ID NOs:1, 3, 4, 5, and 6. In some embodiments, HVR-L1 comprises SEQ ID NO:7, 8, or 9. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In one embodiment, an antibody of the invention comprises a HVR-L3 comprising SEQ ID NO:3. In one embodiment, an antibody of the invention comprises a variant HVR-L3 wherein C8 is W, Y, R, or S. In some embodiments, said variant antibody further comprises HVR-L1, HVR-L2, HVR-H1, HVR-H2 and HVR-H3, wherein each comprises, in order, the sequence depicted in SEQ ID NOs:1, 2, 4, 5, and 6. In some embodiments, HVR-L1 comprises SEQ ID NO:7, 8, or 9. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In one embodiment, an antibody of the invention comprises a HVR-H2 comprising SEQ ID NO:5. In one embodiment, an antibody of the invention comprises a variant HVR-H2 wherein E2 is F. In one embodiment, an antibody of the invention comprises a variant HVR-H2 wherein E2 is V or D. In one embodiment, an antibody of the invention comprises a variant HVR-H2 wherein E6 is G. In one embodiment, an antibody of the invention comprises a variant HVR-H2 wherein E10 is Y. In one embodiment, an antibody of the invention comprises a variant HVR-H2 wherein E12 is A, D, or T. In one embodiment, an antibody of the invention comprises a variant HVR-H2 wherein E13 is D, A, or N. In one embodiment, an antibody of the invention comprises a variant HVR-H2 wherein E15 is V. In one embodiment, an antibody of the invention comprises a variant HVR-H2 wherein E17 is G. In some embodiments, said variant antibody further comprises HVR-L1, HVR-L2, HVR-L3, HVR-H1 and HVR-H3, wherein each comprises, in order, the sequence depicted in SEQ ID NOs:1, 2, 3, 4, and 6. In some embodiments, HVR-L1 comprises SEQ ID NO:7, 8, or 9. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In one embodiment, an antibody of the invention comprises a HVR-H3 comprising SEQ ID NO:6. In one embodiment, an antibody of the invention comprises a variant HVR-H3 wherein F11 is Y. In some embodiments, said variant antibody further comprises HVR-L1, HVR-L2, HVR-L3, HVR-H1 and HVR-H3, wherein each comprises, in order, the sequence depicted in SEQ ID NOs:1, 2, 3, 4, and 6. In some embodiments, HVR-L1 comprises SEQ ID NO:7, 8, or 9. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

A therapeutic agent for use in a host subject preferably elicits little to no immunogenic response against the agent in said subject. In one embodiment, the invention provides such an agent. For example, in one embodiment, the invention provides a humanized antibody that elicits and/or is expected to elicit a human anti-rodent antibody response (such as anti-mouse or anti-rat response) or a human anti-human response at a substantially reduced level compared to an antibody comprising the sequence comprising SEQ ID NOs:10 and/or 11 (FIGS. 1A and 1B) or SEQ ID NOs:12 and/or 13 (FIGS. 9A and 9B depicting rat anti-mouse Fib504 amino acid sequences) in a host subject. In another example, the invention provides a humanized antibody that elicits and/or is expected to elicit no human anti-rodent (such as human anti-mouse (HAMA) or human anti-mouse) or human anti-human antibody response (HAHA).

A humanized antibody of the invention may comprise one or more human and/or human consensus non-hypervariable region (e.g., framework) sequences in its heavy and/or light chain variable domain. In some embodiments, one or more additional modifications are present within the human and/or human consensus non-hypervariable region sequences. In one embodiment, the heavy chain variable domain of an antibody of the invention comprises a human consensus framework sequence, which in one embodiment is the subgroup III consensus framework sequence. In one embodiment, an antibody of the invention comprises a variant subgroup III consensus framework sequence modified at least one amino acid position. For example, in one embodiment, a variant subgroup III consensus framework sequence may comprise a substitution at one or more of positions 71, 73, 78 and/or 94. In one embodiment, said substitution is R71A, N73T, L78A, and/or R94M, in any combination thereof.

As is known in the art, and as described in greater detail hereinbelow, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below). The invention provides antibodies comprising modifications in these hybrid hypervariable positions. In one embodiment, these hybrid hypervariable positions include one or more of positions 26-30, 33-35B, 47-49, 49, 57-65, 93, 94 and 102 in a heavy chain variable domain. In one embodiment, these hybrid hypervariable positions include one or more of positions 24-29, 35-36, 46-49, 49, 56 and 97 in a light chain variable domain. In one embodiment, an antibody of the invention comprises a variant human subgroup consensus framework sequence modified at one or more hybrid hypervariable positions. In one embodiment, an antibody of the invention comprises a heavy chain variable domain comprising a variant human subgroup III consensus framework sequence modified at one or more of positions 28-35, 49, 50, 52a, 53, 54, 58-61, 63, 65, 94 and 102. In one embodiment, the antibody comprises a, T28F, F29I, S30T, S31N, Y32N, A33Y, M34W, and S35G substitution. In one embodiment, the antibody comprises a S49G substitution. In one embodiment, the antibody comprises a V50F or V50D or V50Y substitution. In one embodiment, the antibody comprises a G53Y substitution. In one embodiment, the antibody comprises a G54S substitution. In one embodiment, the antibody comprises a Y58S substitution. In one embodiment, the antibody comprises a A60N or A60D or A60T substitution. In one embodiment, the antibody comprises a D61P or D61A or D61H substitution. In one embodiment, the antibody comprises a V63L substitution. In one embodiment, the antibody comprises a G65S substitution. In one embodiment, the antibody comprises a R94M substitution. In one embodiment, the antibody comprises a R94A or R94E or R94G or R94Q or R94S substitution. In one embodiment, the antibody comprises a G95T substitution. In one embodiment, the antibody comprises one or more of the substitutions at positions 28-35, 49, 50, 52a, 53, 54, 58-61, 63, 65, 94 and 102 and further comprises one or more of the substitutions at positions R71A or N73T or L78A or L78F. In one embodiment, the antibody comprises a Y102F substitution. It can be seen by reference to FIG. 1B that these substitutions are in the HVR-H1, HVR-H2, and/or HVR-H3 of the heavy chain.

In one embodiment, an antibody of the invention comprises a light chain variable domain comprising a variant human subgroup I consensus framework sequence modified at one or more of positions 27, 29-31, 33, 34, 49, 50, 53-55, 91 and 96. In one embodiment, the antibody comprises a Q27E substitution. In one embodiment, the antibody comprises a I29V substitution. In one embodiment, the antibody comprises a S30D substitution. In one embodiment, the antibody comprises a N31T or N31S or N31D substitution. In one embodiment, the antibody comprises a Y32L. In one embodiment, the antibody comprises a A34H substitution. In one embodiment, the antibody comprises a Y49K substitution. In one embodiment, the antibody comprises a A50Y substitution. In one embodiment, the antibody comprises a S53Q substitution. In one embodiment, the antibody comprises a L54S substitution. In one embodiment, the antibody comprises a E55I or E55V substitution. In one embodiment, the antibody comprises a Y91G substitution. In one embodiment, the antibody comprises a W96N or W96L substitution. In one embodiment, the antibody comprises a A25S substitution. In one embodiment, the antibody comprises a A25 to G, S, T, or V substitution. In one embodiment, the antibody comprises a modification selected from one or more of the following groups of substitutions. For example, in one embodiment, the antibody comprises a S26 to G, I, K, N, P, Q, or T substitution. In one embodiment, the antibody comprises a Q27 to E, A, D, G, H, I, K, L, N, Q, R, or V substitution. In one embodiment, the antibody comprises a S28 to A, D, G, H, I, K, N, P, R, T, V, or Y substitution. In one embodiment, the antibody comprises a I29 to V, A, G, K, L, M, Q or R substitution. In one embodiment, the antibody comprises a S30 to D, A, E, G, H, I, K, L, N, P, S, T or V substitution. In one embodiment, the antibody comprises a N31 to D, T, E, or G substitution. In one embodiment, the antibody comprises a Y32 to L, I or M substitution. In one embodiment, the antibody comprises a L33 to A, I, M or V substitution. In one embodiment, the antibody comprises a A34 to H, F, Y or S substitution. In one embodiment, the antibody comprises a Y49 to K or N substitution. In one embodiment, the antibody comprises a A50Y substitution. In one embodiment, the antibody comprises S53Q substitution. In one embodiment, the antibody comprises a L54S substitution. In one embodiment, the antibody comprises a E55 to V, I or K substitution. In one embodiment, the antibody comprises a Y91G substitution. In one embodiment, the antibody comprises a W96 to N, L, W, Y, R, S, A, F, H, I, M, N, R, S, T, V or Y substitution. It can be seen by reference to FIG. 1A that these substitutions are in the HVR-L1, HVR-L2, and/or HVR-L3 of the light chain.

An antibody of the invention can comprise any suitable human or human consensus light chain framework sequences, provided the antibody exhibits the desired biological characteristics (e.g., a desired binding affinity). In one embodiment, an antibody of the invention comprises at least a portion (or all) of the framework sequence of human κ light chain. In one embodiment, an antibody of the invention comprises at least a portion (or all) of human κ subgroup I framework consensus sequence.

In one embodiment, an antibody of the invention comprises a heavy and/or light chain variable domain comprising framework sequences depicted SEQ ID NOS:34-41 and in FIGS. 1, 7 and 8, provided positions 49 of the light chain and 94 of the heavy chain are included in the extended HVRs, and provided said position 49 is K and said position 94 is preferably but not necessarily M and may be R.

Antagonists of the invention can be used to modulate one or more aspects of beta7 associated effects, including but not limited to association with alpha4 integrin subunit, association with alphaE integrin subunit, binding of alpha4beta7 integrin to MAdCAM, VCAM-1 or fibronectin and binding of alphaEbeta7 integrin to E-caderin. These effects can be modulated by any biologically relevant mechanism, including disruption of ligand binding to beta7 subunit or to the alpha4beta7 or alphaEbeta dimeric integrin, and/or by disrupting association between the alpha and beta integrin subunits such that formation of the dimeric integrin is inhibited. Accordingly, in one embodiment, the invention provides a beta7 antagonist antibody that inhibits binding of alpha4 to beta7. In one embodiment, a beta7 antagonist antibody of the invention disrupts binding of alpha4beta7 to MAdCAM. In one embodiment, a beta7 antagonist antibody of the invention disrupts binding of alpha4beta7 to VCAM-1. In one embodiment, a beta7 antagonist antibody of the invention disrupts binding of alpha4beta7 to fibronectin. In one embodiment, a beta7 antagonist antibody of the invention disrupts binding of beta7 to alphaE. In one embodiment, a beta7 antagonist antibody of the invention disrupts binding alphaEbeta7 integrin to E-cadherin. Interference can be direct or indirect. For example, a beta7 antagonist antibody may bind to beta7 within a sequence of the alpha4beta7 or alphaEbeta7 dimerization region, and thereby inhibit interaction of the integrin subunits and formation of an integrin dimer. In a further example, a beta7 antagonist antibody may bind to a sequence within the ligand binding domain of beta7 subunit and thereby inhibit interaction of said bound domain with its binding partner (such as fibronectin, VCAM, and/or MAdCAM for the alpha4beta7 integrin; or E-cadherin for the alphaEbeta7 integrin). In another example, a beta7 antagonist antibody may bind to a sequence that is not within the integrin subunit dimerization domain or a ligand binding domain, but wherein said beta7 antagonist antibody binding results in disruption of the ability of the beta7 domain to interact with its binding partner (such as an alpha4 or alphaE integrin subunit and/or a ligand such as fibronectin, VCAM, MAdCAM, or E-cadherein). In one embodiment, an antagonist antibody of the invention binds to beta7 (for example, the extracellular domain) such that beta7 dimerization with the alpha4 or alphaE subunit is disrupted. In one embodiment, an antagonist antibody of the invention binds to beta7 such that ability of beta7 and/or an alpha4beta7 and/or an alphaEbeta7 integrin to bind to its respective ligand or ligands is disrupted. For example, in one embodiment, the invention provides an antagonist antibody which upon binding to a beta7 molecule inhibits dimerization of said molecule. In one embodiment, a beta7 antagonist antibody of the invention specifically binds a sequence in the ligand binding domain of beta7. In one embodiment, a beta7 antagonist antibody of the invention specifically binds a sequence in the ligand binding domain of beta7 such that ligand binding (i.e., fibronectin, VCAM, and/or MAdCAM) to the alpha4beta7 integrin is disrupted. In one embodiment, a beta7 antagonist antibody of the invention specifically binds a sequence in the ligand binding domain of beta7 such that ligand binding (i.e., E-cadherin) to the alphaEbeta7 integrin is disrupted.

In one embodiment, an antagonist antibody of the invention disrupts beta7 dimerization comprising heterodimerization (i.e., beta7 dimerization with an alpha4 or alphaE integrin subunit molecule).

In one embodiment, an antagonist antibody of the invention binds to an epitope on the beta7 integrin subunit that maps to amino acids 176-237. In another embodiment, an antagonist antibody of the invention binds to the same epitope on the beta7 integrin that is the substantially the same epitope as Fib504.64 (ATCC HB-293). Determination of epitope binding is by standard techniques including without limitation competition binding analysis.

In one aspect, the invention provides an antibody comprising a combination of one, two, three, four, five or all of the HVR sequences depicted in the table of amino acid substitutions in FIG. 13.

A therapeutic agent for use in a host subject preferably elicits little to no immunogenic response against the agent in said subject. In one embodiment, the invention provides such an agent. For example, in one embodiment, the invention provides a humanized antibody that elicits and/or is expected to elicit a human anti-rat or human anti-mouse or human anti-human antibody response at a substantially reduced level compared to an antibody comprising the sequence of SEQ ID NOS:10, 11, 12 and/or SEQ ID NO:13 (rat anti-mouse Fib504 (ATCC HB-293), FIGS. 1 and 9) in a host subject. In another example, the invention provides a humanized antibody that elicits and/or is expected to elicit no human anti-mouse, human anti-rat, or human anti-human antibody response.

A humanized antibody of the invention may comprise one or more human and/or human consensus non-hypervariable region (e.g., framework) sequences in its heavy and/or light chain variable domain. In some embodiments, one or more additional modifications are present within the human and/or human consensus non-hypervariable region sequences. In one embodiment, the heavy chain variable domain of an antibody of the invention comprises a human consensus framework sequence, which in one embodiment is the subgroup III consensus framework sequence. In one embodiment, an antibody of the invention comprises a variant subgroup III consensus framework sequence modified at least one amino acid position. For example, in one embodiment, a variant subgroup III consensus framework sequence may comprise a substitution at one or more of positions 71, 73, 78 and/or 94, although position 94 is part of an extended heavy chain hypervariable region-H3 of the present invention. In one embodiment, said substitution is R71A, N73T, N78A, and/or R94M, in any combination thereof.

An antibody of the invention can comprise any suitable human or human consensus light chain framework sequences, provided the antibody exhibits the desired biological characteristics (e.g., a desired binding affinity). In one embodiment, an antibody of the invention comprises at least a portion (or all) of the framework sequence of human κ light chain. In one embodiment, an antibody of the invention comprises at least a portion (or all) of human κ subgroup I framework consensus sequence.

Antagonists of the invention can be used to modulate one or more aspects of beta7 associated effects. For example, a beta7 antagonist antibody may bind to beta7 within a sequence of the alpha4beta7 or alphaEbeta7 dimerization region, and thereby inhibit interaction of the integrin subunits and formation of an integrin dimer. In a further example, a beta7 antagonist antibody may bind to a sequence within the ligand binding domain of beta7 subunit and thereby inhibit interaction of said bound domain with its binding partner (such as fibronectin, VCAM, and/or MAdCAM for the alpha4beta7 integrin; or E-cadherin for the alphaEbeta7 integrin). In another example, a beta7 antagonist antibody may bind to a sequence that is not within the integrin subunit dimerization domain or a ligand binding domain, but wherein said beta7 antagonist antibody binding results in disruption of the ability of the beta7 domain to interact with its binding partner (such as an alpha4 or alphaE integrin subunit and/or a ligand such as fibronectin, VCAM, MAdCAM, or E-cadherein). In one embodiment, an antagonist antibody of the invention binds to beta7 (for example, the extracellular domain) such that beta7 dimerization with the alpha4 or alphaE subunit is disrupted. In one embodiment, an antagonist antibody of the invention binds to beta7 such that ability of beta7 and/or an alpha4beta7 and/or an alphaEbeta7 integrin to bind to its respective ligand or ligands is disrupted. For example, in one embodiment, the invention provides an antagonist antibody which upon binding to a beta7 molecule inhibits dimerization of said molecule. In one embodiment, a beta7 antagonist antibody of the invention specifically binds a sequence in the ligand binding domain of beta7. In one embodiment, a beta7 antagonist antibody of the invention specifically binds a sequence in the ligand binding domain of beta7 such that ligand binding (i.e., fibronectin, VCAM, and/or MAdCAM) to the alpha4beta7 integrin is disrupted. In one embodiment, a beta7 antagonist antibody of the invention specifically binds a sequence in the ligand binding domain of beta7 such that ligand binding (i.e., E-cadherin) to the alphaEbeta7 integrin is disrupted.

In one embodiment, an antagonist antibody of the invention disrupts beta7 dimerization comprising heterodimerization (i.e., beta7 dimerization with an alpha4 or alphaE integrin subunit molecule.

In some instances, it may be advantageous to have a beta7 antagonist antibody that does not interfere with binding of a ligand (such as fibronectin, VCAM, MAdCAM, or alphaE) to beta7 subunit as part of an integrin or to an alpha4beta7 integrin or an alphaEbeta7 integrin as a dimer. Accordingly, in one embodiment, the invention provides an antibody that does not bind a fibronectin, VCAM, MAdCAM, or E-cadherin binding site on beta7 but, instead, inhibits interaction between beta7 subunit and an alpha subunit (such as alpha4 or alphaE integrin subunit) such that a biologically active integrin is prevented from forming. In one example, an antagonist antibody of the invention can be used in conjunction with one or more other antagonists, wherein the antagonists are targeted at different processes and/or functions within the beta7 integrin axis. Thus, in one embodiment, a beta7 antagonist antibody of the invention binds to an epitope on beta7 distinct from an epitope bound by another beta7 or an alpha/beta integrin antagonist (such as an alpha4beta7 antibody, including monoclonal antibody or an antibody, such as a humanized antibody or monoclonal antibody derived from and/or having the same or effectively the same binding characteristics or specificity as an antibody derived from a murine antibody).

In one embodiment, the invention provides a beta7 antagonist antibody that disrupts beta7-alpha4 or -alphaE multimerization into the respective integrin as well as ligand binding. For example, an antagonist antibody of the invention that inhibits beta7 dimerization with alpha4 or alphaE integrin subunit may further comprise an ability to compete with ligand for binding to beta7 or the integrin dimer (e.g., it may interfere with the binding of fibronectin, VCAM, and/or MAdCAM to beta7 and/or alpha4beta7; or it may interfere with the binding of E-cadherin to beta7 or alphaEbeta7.)

In one embodiment of a beta7 antagonist antibody of the invention, binding of the antagonist to beta7 inhibits ligand binding activated cellular adhesion. In another embodiment of a beta7 antagonist antibody of the invention, binding of the antagonist to beta7 in a cell inhibits recruitment of the cell to the cells and/or tissue in which the beta7-containing integrin is expressed.

In one embodiment, a beta7 antagonist antibody of the invention specifically binds at least a portion of amino acids 176-250 (optionally amino acids 176-237) of the beta7 extracellular domain (see Tidswell, M. et al. (1997) J. Immunol. 159:1497-1505) or variant thereof, and reduces or blocks binding of ligands MAdCAM, VCAM-1, fibronectin, and/or E-cadherin. In one embodiment, such blocking of ligand binding disrupts, reduces and/or prevents adhesion of a cell expressing the ligand to a cell expressing the beta7-containing ligand. In one embodiment, an antagonist antibody of the invention specifically binds an amino acid sequence of beta7 comprising residues 176-237. In one embodiment, an antagonist antibody of the invention specifically binds a conformational epitope formed by part or all of at least one of the sequences selected from the group consisting of residues 176-237 of beta7. In one embodiment, an antagonist antibody of the invention specifically binds an amino acid sequence having at least 50%, at least 60%, at least 70%, at least 80%, at least 90%, at least 95%, at least 98%, at least 99% sequence identity or similarity with the amino acid sequence of residues 176-237 or residues 176-250 of human beta7. In one embodiment, the antagonist anti-beta7 antibody of the invention binds the same epitope as the anti-beta7 antibody Fib504 produced by hybridoma ATCC HB-293.

In one aspect, the invention provides compositions comprising one or more antagonist antibodies of the invention and a carrier. In one embodiment, the carrier is pharmaceutically acceptable.

In one aspect, the invention provides nucleic acids encoding a beta7 antagonist antibody of the invention.

In one aspect, the invention provides vectors comprising a nucleic acid of the invention.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, E. coli. In one embodiment, a host cell is a eukaryotic cell, for example a mammalian cell such as Chinese Hamster Ovary (CHO) cell.

In one aspect, the invention provides methods for making an antagonist of the invention. For example, the invention provides a method of making a beta7 antagonist antibody (which, as defined herein includes full length and fragments thereof), said method comprising expressing in a suitable host cell a recombinant vector of the invention encoding said antibody (or fragment thereof), and recovering said antibody.

In one aspect, the invention provides an article of manufacture comprising a container; and a composition contained within the container, wherein the composition comprises one or more beta7 antagonist antibodies of the invention. In one embodiment, the composition comprises a nucleic acid of the invention. In one embodiment, a composition comprising an antagonist antibody further comprises a carrier, which in some embodiments is pharmaceutically acceptable. In one embodiment, an article of manufacture of the invention further comprises instructions for administering the composition (for example, the antagonist antibody) to a subject.

In one aspect, the invention provides a kit comprising a first container comprising a composition comprising one or more beta7 antagonist antibodies of the invention; and a second container comprising a buffer. In one embodiment, the buffer is pharmaceutically acceptable. In one embodiment, a composition comprising an antagonist antibody further comprises a carrier, which in some embodiments is pharmaceutically acceptable. In one embodiment, a kit further comprises instructions for administering the composition (for example, the antagonist antibody) to a subject.

Beta7 integrins and their ligands are variously expressed in disease states. [The expression of MAdCAM-1 on gut endothelium is increased in sites of mucosal inflammation in patients with inflammatory bowel disease (UC and CD) and colonic lamina propria of UC and CD patients also show increased CD3+ and a4b7+ cells compared to IBS controls (see Souza H., et al., Gut 45:856 (1999)). MAdCAM-1 expression was observed to be associated with portal tract inflammation in liver diseases and may be important in recruitment of alpha4beta7+ lymphocytes to the liver during inflammation. (Hillan, K., et al., Liver. 19(6):509-18 (1999)) MAdCAM-1 on hepatic vessels supports adhesion of a4b7+ lymphocytes from patients with IBD and primary sclerosing cholangitis. The adhesion was inhibited by anti-MAdCAM-1, anti-alpha4beta7, or anti-alpha4 antibodies. (Grant A J. et al., Hepatology. 33(5):1065-72 (2001)). MAdCAM-1, VCAM-1 and E-cadherin are expressed on brain endothelial cells and/or on microvessels in the inflamed central nervous system. Beta7 integrins contribute to demyelinating disease of the CNS (Kanwar et al., J. Neuroimmunology 103, 146 (2000)). Expression of alpha4beta7 was significantly higher in the LPL of CD than in controls and patients with UC (Oshitani, N. et al., International Journal of Molecule Medicine 12, 715-719 (2003)). IELs from CD patients may be chronically stimulated and recruited from the periphery (Meresse, B., et al., Human Immunology, 62, 694-700 (2001)). In human liver disease, alphaEbeta7 T cells (CD4+ and CD8+) are preferentially accumulated in human livers where E-cadherin is expressed on hepatocytes and bile duct epithelium (Shimizu, Y., et al., Journal of Hepatology 39, 918-924 (2003)). In chronic pancreatitis, CD8+ CD103+ T cells, analogous to intestinal intraepithelial lymphocytes, infiltrate the pancreas in chronic pancreatitis (Matthias, P., et al., Am J Gastroenterol 93:2141-2147 (1998)). Upregulation of alphaEbeta7 is found in systemic lupus erythematosus patients with specific epithelial involvement (Pang et al., Arthritis & Rheumatism 41:1456-1463 (1998)). In Sjogren's Syndrome, CD8+ alphaEbeta7+ T cells adhere and kill acinar epithelial cells by inducing apoptosis (Kroneld et al., Scand J Rheumatol 27:215-218, 1998) Integrin alpha4beta7 and alphaEbeta7 play a role in T cell epidermotropism during skin inflammation and contribute to skin allograft rejection (Sun et al., Transplantation 74, 1202, 2002). Teraki and Shiohara showed preferential expression of aEb7 integrin on CD8+ T cells in psoriatic epidermis (Teraki and Shiohara, Br. J. Dermatology 147, 1118, 2002). Sputum T lymphocytes are activated IELs (CD69+ CD103+) in asthma, COPD, and normal subjects (Leckie et. al., Thorax 58, 23, 2003). CD103+ (aEb7+) CTL accumulate with graft epithelium during clincial renal allograft rejection (Hadley et al., Transplantation 72, 1548, 2001)] Thus, in one aspect, the invention provides use of a beta7 antagonist antibody of the invention to inhibit beta7 integrin-ligand interaction to reduce or alleviate disease, such as one or more of the above described disease states. In one embodiment, the antibody of the invention is used in the preparation of a medicament for the therapeutic and/or prophylactic treatment of a disease, such as an inflammatory disease including without limitation inflammatory bowel disease (such as Crohn's disease and ulcerative colitis), inflammatory liver disease, inflammation of the CNS, chronic pancreatitis, systemic lupus erythematosus, Sjogren's syndrome, psoriasis and skin inflammation, asthma, chronic obstructive pulmonary disease (COPD), interstitial lung disease, allergy, autoimmune disease, transplantation rejection, renal graft rejection, graft versus host disease, diabetes, and cancer.

In one aspect, the invention provides use of a nucleic acid of the invention in the preparation of a medicament for the therapeutic and/or prophylactic treatment of a disease, such as an immune (such as autoimmune or inflammatory) disorder including without limitation, inflammatory bowel disease (such as Crohn's disease or ulcerative colitis) and allergic reaction (such as disorders of the respiratory system, skin, joints, allergic asthma and other organs affected by allergic reaction mediated by a beta7-containing integrin).

In one aspect, the invention provides use of an expression vector of the invention in the preparation of a medicament for the therapeutic and/or prophylactic treatment of a disease, such as an immune (such as autoimmune or inflammatory) disorder including without limitation, inflammatory bowel disease (such as Crohn's disease or ulcerative colitis) and allergic reaction (such as disorders of the respiratory system, skin, joints, and other organs affected by allergic reaction mediated by a beta7-containing integrin).

In one aspect, the invention provides use of a host cell of the invention in the preparation of a medicament for the therapeutic and/or prophylactic treatment of a disease, such as an immune (such as autoimmune or inflammatory) disorder including without limitation, inflammatory bowel disease (such as Crohn's disease or ulcerative colitis) and allergic reaction (such as disorders of the respiratory system, skin, joints, and other organs affected by allergic reaction mediated by a beta7-containing integrin).

In one aspect, the invention provides use of an article of manufacture of the invention in the preparation of a medicament for the therapeutic and/or prophylactic treatment of a disease, such as an immune (such as autoimmune or inflammatory) disorder including without limitation, inflammatory bowel disease (such as Crohn's disease or ulcerative colitis) and allergic reaction (such as disorders of the respiratory system, skin, joints, and other organs affected by allergic reaction mediated by a beta7-containing integrin).

In one aspect, the invention provides use of a kit of the invention in the preparation of a medicament for the therapeutic and/or prophylactic treatment of a disease, such as an immune (such as autoimmune or inflammatory) disorder including without limitation, inflammatory bowel disease (such as Crohn's disease or ulcerative colitis) and allergic reaction (such as disorders of the respiratory system, skin, joints, and other organs affected by allergic reaction mediated by a beta7-containing integrin).

The invention provides methods and compositions useful for modulating disease states associated with dysregulation of the beta7 integrin mediated cell-cell interaction process. The beta7 integrins are involved in multiple biological and physiological functions, including, for example, inflammatory disorders and allergic reactions. Thus, in one aspect, the invention provides a method comprising administering to a subject an antibody of the invention.

In one aspect, the invention provides a method of inhibiting beta7 integrin mediated inflammation, said method comprising contacting a cell or tissue with an effective amount of a antibody of the invention, whereby lymphocyte or B-cell interaction and binding to a beta7 integrin-expressing cell is inhibited.

In one aspect, the invention provides a method of treating a pathological condition associated with dysregulation of beta7 integrin binding in a subject, said method comprising administering to the subject an effective amount of an antibody of the invention, whereby said condition is treated.

In one aspect, the invention provides a method of inhibiting the binding of a lymphocyte expressing a beta7 integrin ligand (such as a cell expressing MAdCAM, VCAM, E-cadherin or fibronectin) to a cell that expresses beta7 integrin (such as alpha4beta7 or alphaEbeta7 integrins), said method comprising contacting said cell with an antibody of the invention thereby inhibiting or preventing adhesion of the cells and causing a reduction of inflammatory reaction.

In one aspect, the invention provides a method for treating or preventing an inflammatory disorder associated with increased expression or activity of beta7 integrin or increased interaction between a beta7 integrin on one cell and a beta7 integrin receptor on another cell, said method comprising administering to a subject in need of such treatment an effective amount of an antibody of the invention, thereby effectively treating or preventing said inflammatory disorder. In one embodiment, said inflammatory disorder is inflammatory bowel disease (IBD). In another embodiment, said inflammatory disorder is an allergic reaction.

Methods of the invention can be used to affect any suitable pathological state, for example, cells and/or tissues associated with dysregulation of the beta7 integrin binding pathway. Beta7 integrins are expressed primarily on leukocytes (Tidswell, M. et al. (1997) supra). In one embodiment, a leukocyte is targeted in a method of the invention and is prevented from binding to a cell expressing a ligand of the beta7 integrin. For example, an an intra-epithelial lymphocyte expressing E-cadherin is prevented, according to the invention, from binding to an alphaEbeta7-expressing cell by an antagonist anti-beta7 antibody. Cells expressing MAdCAM, VCAM-1 or fibronectin are prevented by an antagonist anti-beta7 antibody of the invention from binding to a leukocyte expressing alpha4beta7.

Methods of the invention can further comprise additional treatment steps. For example, in one embodiment, a method further comprises a step wherein a targeted cell and/or tissue (for example, an endothelial cell of the intestinal lining) is exposed to an anti-TNF antibody or a small molecule therapeutic agent including without limitation 5-ASA compounds (including without limitation As described herein, beta7 integrins mediate important biological processes the dysregulation of which leads to numerous pathological conditions. Accordingly, in one embodiment of methods of the invention, a cell that is targeted (for example, an endothelial cell) is one in which adhesion of a cell expressing a beta7 integrin ligand of a beta7 integrin (where the cell may be, without limitation, a lymphocyte, and the ligand may be MAdCAM, VCAM or E-cadherin) is disrupted, inhibited, or prevented as compared to the cells in the absence of the anti-beta7 antagonist antibody of the invention. In one embodiment, a method of the invention inhibits lymphocyte homing, thereby inhibiting inflammation at the site of beta7 integrin expression. For example, contact with an antagonist of the invention may result in a cell's inability to adhere to a cell expressing a ligand of a beta7 integrin.

BRIEF DESCRIPTION OF THE DRAWINGS

FIGS. 1A and 1B depict alignment of sequences of the variable light and heavy chains for the following: light chain human subgroup kappa I consensus sequence (FIG. 1A, SEQ ID NO:23), heavy chain human subgroup III consensus sequence (FIG. 1B, SEQ ID NO:24), rat anti-mouse beta7 antibody (Fib504) variable light chain (FIG. 1A, SEQ ID NO:10), rat anti-mouse beta7 antibody (Fib504) variable heavy chain (FIG. 1B, SEQ ID NO:11), and humanized antibody vairiants: Humanized hu504 K graft variable light chain (FIG. 1A, SEQ ID NO:25), humanized hu504K graft variable heavy chain (FIG. 1B, SEQ ID NO:26), variant hu504.5 (amino acid variations from humanized hu504K graft are indicated in FIG. 1A (light chain) and FIG. 1B (heavy chain) for variants hu504.5, hu504.16, and hu504.32. Additional amino acid substitutions in the HVR-H1 and HVR-H2 of the hu504K graft which resulted in beta7 binding antibodies are indicated in FIG. 1C.

FIGS. 2A and 2B depict the full length sequence of the human consensus subgroup III sequence light chain (FIG. 2A, SEQ ID NO:27) and heavy chain (FIG. 2B, SEQ ID NO:28). HVRs are underlined.

FIGS. 3A and 3B depict the full length sequence of the humanized504 graft containing rat Fib504 hypervariable regions (as described herein) grafted into the human kappa I consensus sequence light chain (FIG. 3A, SEQ ID NO:29) and into the human subgroup III consensus sequence heavy chain (FIG. 3B, SEQ ID NO:30). HVRs are underlined.

FIGS. 4A and 4B depict the full length sequence of the humanized 504 Kgraft in which position 49 of the light chain of the hu504 graft is a Y49K substitution. The hu504 Kgraft light chain is depicted by SEQ ID NO:31 and the hu504 Kgraft heavy chain is depicted by SEQ ID NO:30. HVRs are underlined.

FIGS. 5A and 5B depict the full length sequence of the hu504K-RF graft in which positions 71 and 78 of the heavy chain of the hu504 graft are an A71R substitution and a A78F substitution from the hu504 Kgraft sequence. The hu504K-RF graft light chain is depicted by SEQ ID NO:31 and the hu504K-RF graft heavy chain is depicted by SEQ ID NO:32. HVRs are underlined.

FIGS. 6A and 6B depict the full length sequence of the hu504.32 variant comprising the heavy chain of the hu504K-RF graft (SEQ ID NO:32) and T31D and Y32L substitutions in the light chain of the hu504 Kgraft (SEQ ID NO:33). HVRs are underlined.

FIG. 7A-FIG. 7B and FIG. 8A-FIG. 8B depict exemplary acceptor human consensus framework sequences for use in practicing the instant invention with sequence identifiers as follows:

Variable Light (VL) Consensus Frameworks (FIG. 7A,B)

human VL kappa subgroup I consensus framework (SEQ ID NO:14)
human VL kappa subgroup I consensus framework minus extended HVR-L2 (SEQ ID NO:15)
human VL kappa subgroup II consensus framework (SEQ ID NO:16)
human VL kappa subgroup III consensus framework (SEQ ID NO:17)
human VL kappa subgroup IV consensus framework (SEQ ID NO:18)
Shaded regions represent light chain HVRs (indicated as L1, L2, and L3).

Variable Heavy (VH) Consensus Frameworks (FIG. 8a, B)

human VH subgroup I consensus framework minus Kabat CDRs (SEQ ID NO:19)
human VH subgroup I consensus framework minus extended hypervariable regions (SEQ ID NOs:20-22)
human VH subgroup II consensus framework minus Kabat CDRs (SEQ ID NO:48)
human VH subgroup II consensus framework minus extended hypervariable regions (SEQ ID NOs:49-51)
human VH subgroup III consensus framework minus Kabat CDRs (SEQ ID NO:52)
human VH subgroup III consensus framework minus extended hypervariable regions (SEQ ID NOs:53-55)

human VH acceptor framework minus Kabat CDRs (SEQ ID NO:56)
human VH acceptor framework minus extended hypervariable regions (SEQ ID NOs:57-58)
human VH acceptor 2 framework minus Kabat CDRs (SEQ ID NO:59)
human VH acceptor 2 framework minus extended hypervariable regions (SEQ ID NOs:60-62)

FIGS. 9A and 9B depict an amino acid sequence of the variable chains of rat anti-mouse integrin beta7 Fib504 antibody produced by the hybridoma ATCC HB-293. HVRs are underlined. Variable light chain is depicted in FIG. 9A (SEQ ID NO:12) and variable heavy chain is depicted in FIG. 9B (SEQ ID NO:13).

Figure 10B:
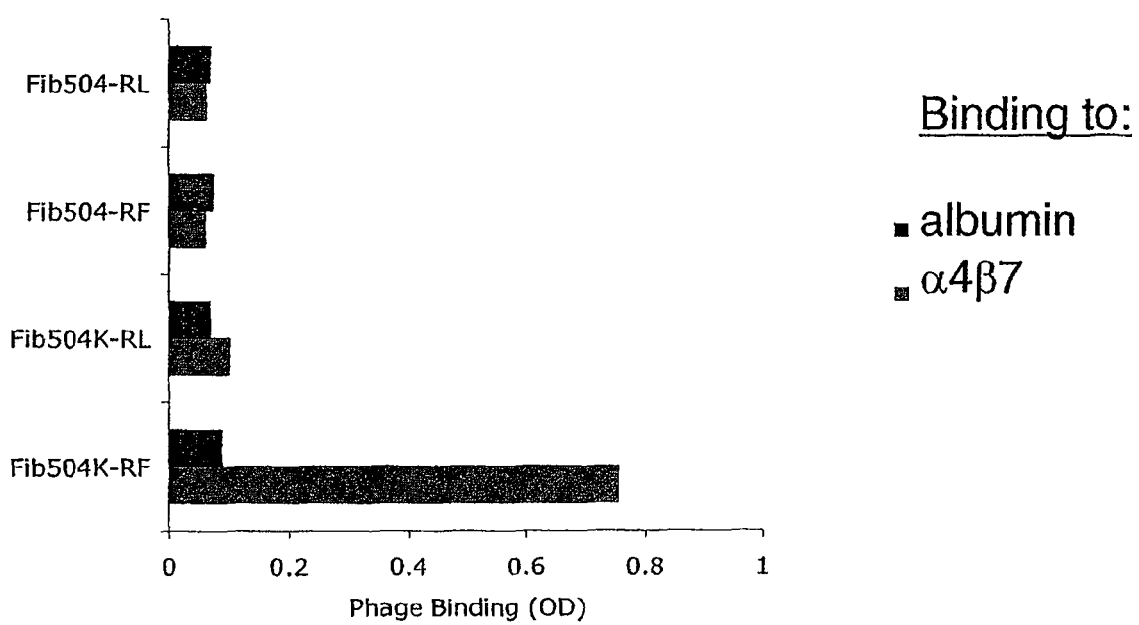

FIG. 10A depicts amino acid positions in the heavy chain of various consensus sequences (hu subgroups I-III). The consensus sequence used for development of the Herceptin® anti-HER2 antibody, rat Fib504, and hu504-RL and hu504-RF frameworks are described in the Examples herein. FIG. 10B is a bar graph showing the relative binding of alpha4beta7 to hu504graft antibody and hu504 Kgraft antibody as a function of "RL" or "RF" framework modifications as described in Example 1.

Figure 11A:
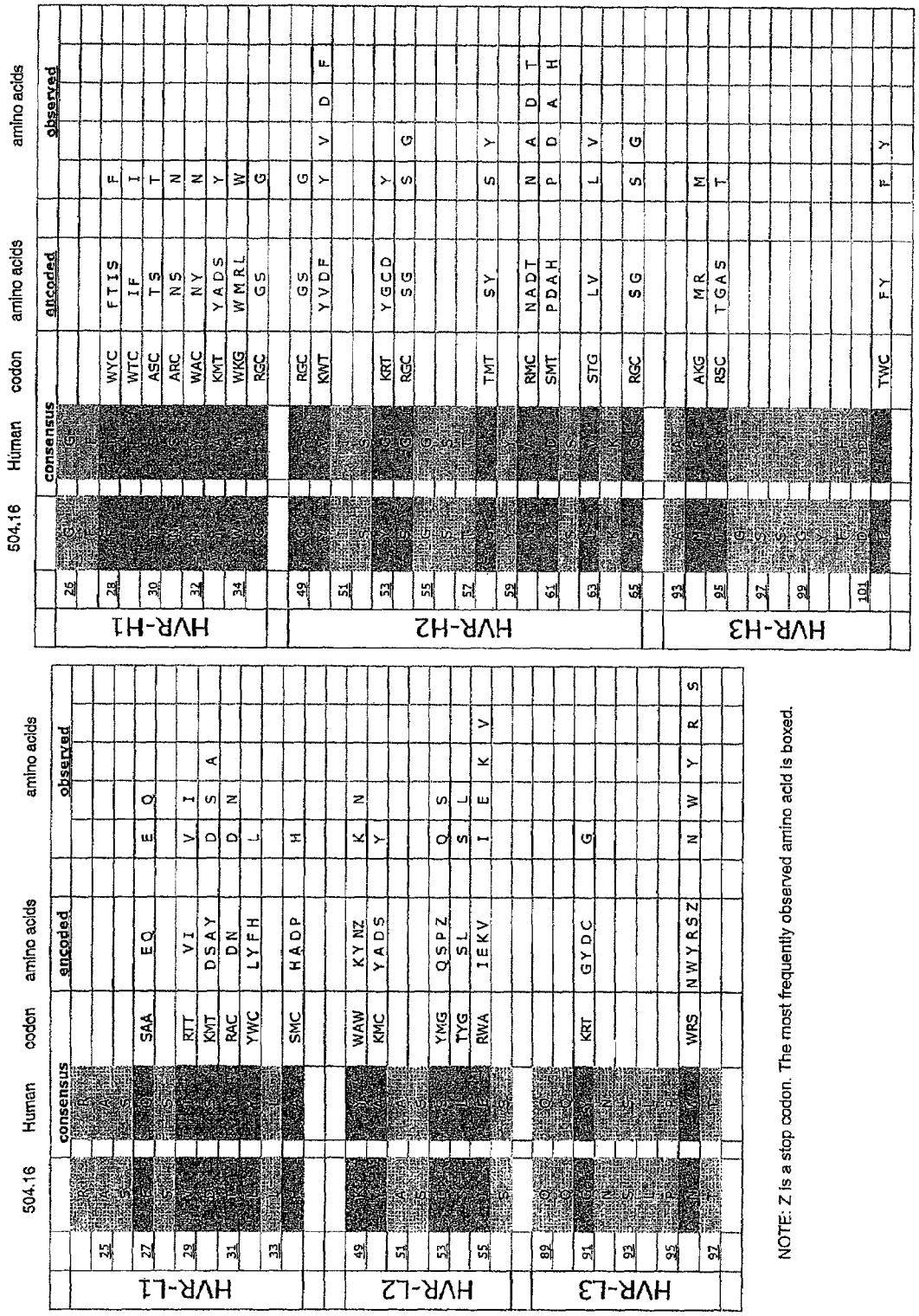
Figure 11B:
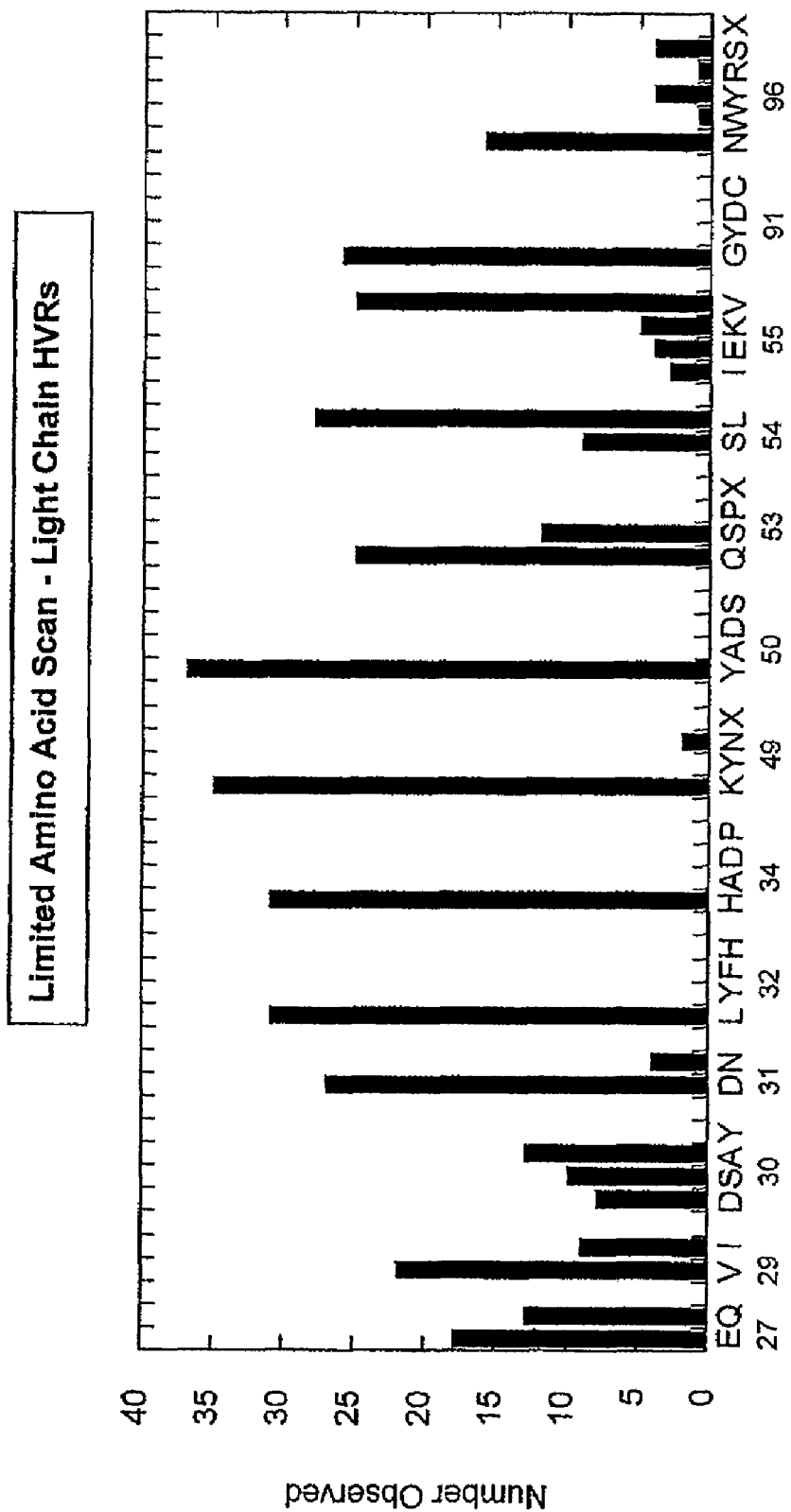

FIG. 11A-11C. FIG. 11A tabulates the HVR changes resulting from affinity-maturation performed by offering a limited range of amino acid substitutions in the hu504.16 variant. The results are from libraries with individually modified HVRs in the hu504.16 variant as described in Example 2 herein. Amino acid abbreviations in boxes are amino acids found more frequently in the beta7-binding antibodies (phage-selected antibodies). FIGS. 11B and 11C are bar graphs of the results in FIG. 11A indicating the number and type of amino acid substitutions in the hu504.16 variant (light chain, FIG. 11B; heavy chain, FIG. 11C) detectable by the mutagenesis and selection methods of Example 2.

FIG. 12 tabulates the results of affinity maturation performed by offering a broad range of possible amino acid substitutions in the HVRs of hu504.32 variant as described in Example 2. The shaded boxes indicate the amino acid that was detected most frequently in antibodies detected as beta7-binding antibodies by the mutagenesis and selection methods of Example 2.

FIG. 13 depicts HVR sequences of rat anti-mouse Fib504 (ATCC-293), and the human consensus (left columns). Examples of amino acid substitutions observed for each HVR position (not meant to be limiting) by the assays described in the Examples (amino acid substitutions observed by soft amino acid randomization, broad amino acid substitution scan, and limited amino acid substitution scan) are shown to the right, (a useful method of modifying HVRs for humanization, applicable to variants of the present invention, is found in U.S. Application Ser. No. 60/545,840, filed Feb. 19, 2004).

Figure 14:
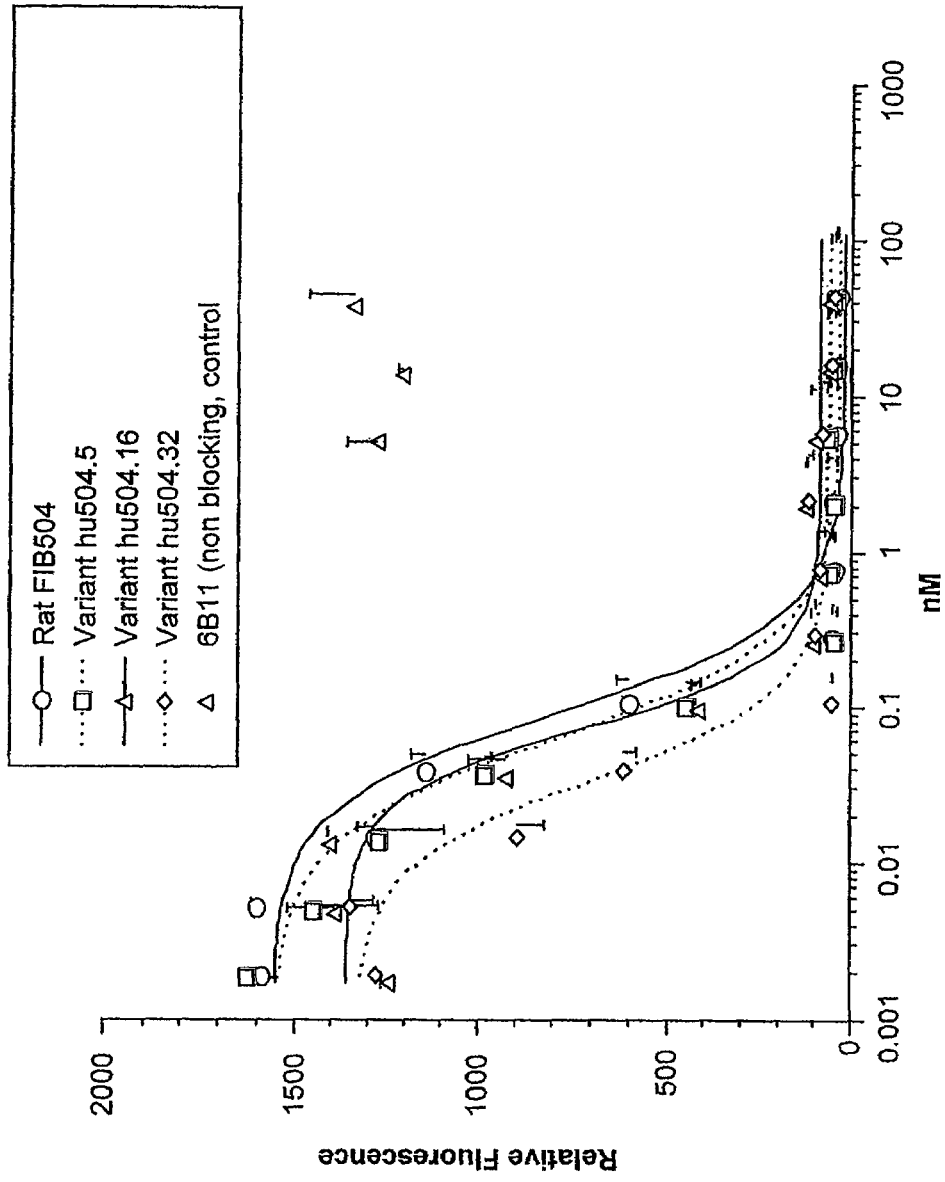

FIG. 14 is an exemplary graphical representation of Fib504 and variant antibody binding to MAdCAM as a function of antibody concentration as described in Example 3. $IC_{50}$ and $IC_{90}$ values for the antibodies were determined.

FIG. 15 depicts the light and heavy chain HVR amino acid sequences for the 504.32R anti-beta7 antibody with respect to position according to the Kabat numbering system and a relative numbering system (A-F) for the six HVRs of the antibody. Amino acids at positions 71, 73, and 78 of the heavy chain FR3 region are also depicted. Useful amino acid substitutions are also listed for many of the positions in the HVRs or the heavy chain FR3 region.

Figure 16:
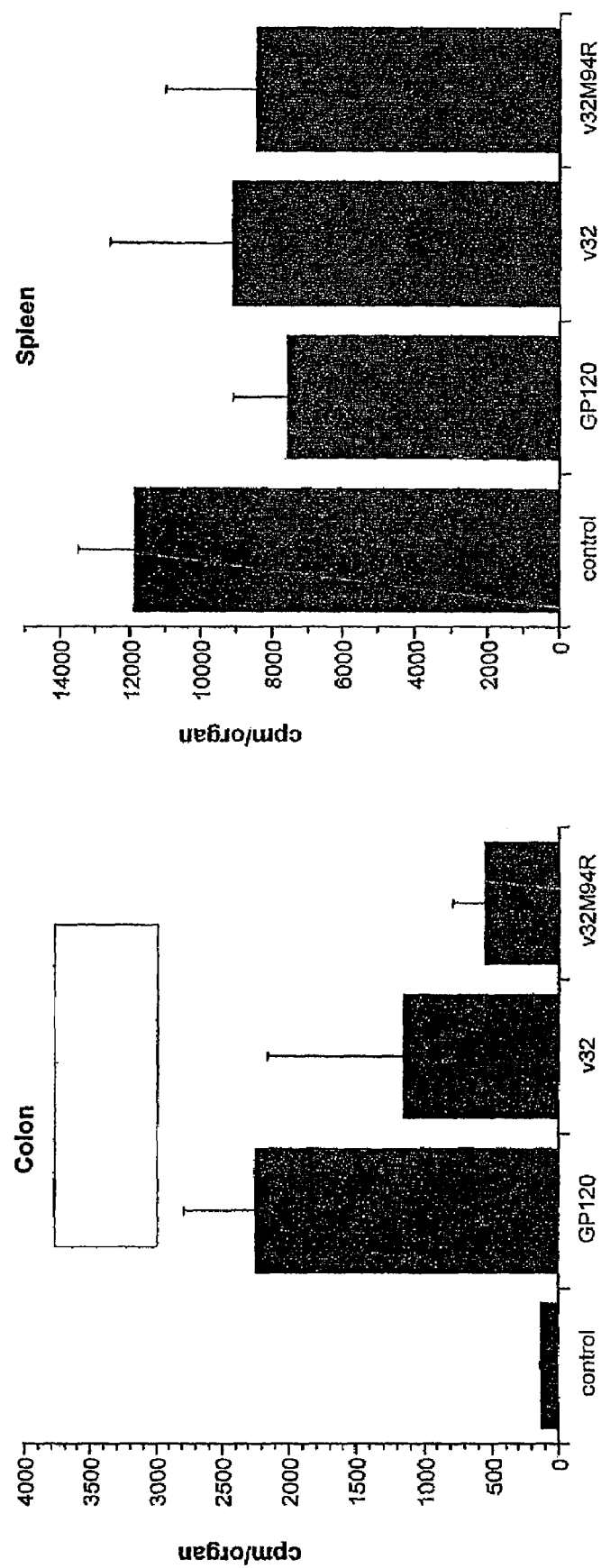

FIG. 16 shows bar graphs of the relative ability of the 504.32M and 504.32R antibodies to block homing of radio-labelled T cells to the colon of mice experiencing inflammatory bowel disease.

MODES FOR CARRYING OUT THE INVENTION

The invention provides methods, compositions, kits and articles of manufacture for identifying and/or using inhibitors of the beta7 signaling pathway.

Details of these methods, compositions, kits and articles of manufacture are provided herein.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

DEFINITIONS

By "beta7 subunit" or "β7 subunit" is meant the human β7 integrin subunit (Erle et al., (1991) J. Biol. Chem. 266:11009-11016). The beta7 subunit associates with alpha4 intetrin subunit, such as the human α4 subunit (Kilger and Holzmann (1995) J. Mol. Biol. 73:347-354). The alpha4beta7 integrin is expressed on a majority of mature lymphocytes, as well as a small population of thymocytes, bone marrow cells and mast cells. (Kilshaw and Murant (1991) Eur. J. Immunol. 21:2591-2597; Gurish et al., (1992) 149: 1964-1972; and Shaw, S. K. and Brenner, M. B. (1995) Semin. Immunol. 7:335). The beta7 subunit also associates with the alphaE subunit, such as the human alphaE integrin subunit (Cepek, K. L, et al. (1993) J. Immunol. 150:3459). The alphaEbeta7 integrin is expressed on intra-intestinal epithelial lymphocytes (iIELs) (Cepek, K. L. (1993) supra). The beta7 subunit that binds to the humanized anti-beta7 antibody of the invention may be naturally occurring and may be soluble or localized to the surface of a cell.

By "alphaE subunit" or "alphaE integrin subunit" or "αE subunit" or "αE integrin subunit" or "CD103" is meant an integrin subunit found to be associated with beta7 integrin on intra-epithelial lymphocytes, which alphaEbeta7 integrin mediates binding of the iELs to intestinal epithelium expressing E-caderin (Cepek, K. L. et al. (1993) J. Immunol. 150: 3459; Shaw, S. K. and Brenner, M. B. (1995) Semin. Immunol. 7:335).

"MAdCAM" or "MAdCAM-1" are used interchangeably in the context of the present invention and refer to the protein mucosal addressin cell adhesion molecule-1, which is a single chain polypeptide comprising a short cytoplasmic tail, a transmembrane region and an extracellular sequence composed of three immunoglobulin-like domains. The cDNAs for murine, human and macaque MAdCAM-1 have been cloned (Briskin, et al, (1993) Nature, 363:461-464; Shyjan et al., (1996) J. Immunol. 156:2851-2857).

"VCAM-1" or "vascular cell adhesion molecule-1" "CD106" refers to a ligand of alpha4beta7 and alpha4beta1, expressed on activated endothelium and important in endothelial-leukocyte interactions such as binding and transmigration of leukocytes during inflammation.

"E-cadherin" refers to a member of the family of cadherins, where E-cadherin is expressed on epithelial cells. E-cadherin is a ligand of the alphaEbeta7 integrin and mediates binding of iEL-expressed alphaEbeta7 to intestinal epithelium, although its function in lymphocyte homing is unclear (. E-cadherin expression is upregulated by TGF-beta1.

"Fibronectin" refers to Fibronectin is involved in tissue repair, embryogenesis, blood clotting, and cell migration/adhesion. It serves as a linker in the ECM (extracellular matrix), and as dimer found in the plasma (plasma fibronectin). The plasma form is synthesized by hepatocytes, while the ECM form is made by fibroblasts, chondrocytes, endothelial cells, macrophages, as well as certain epithelial cells. In this context, it interacts with the alpha4beta7 integrin to mediate aspects of lymphocyte homing or adhesion. The ECM form of fibronectin serves as a general cell adhesion molecule by anchoring cells to collagen or proteoglycan substrates. Fibronectin also can serve to organize cellular interaction with the ECM by binding to different components of the extracellular matrix and to membrane-bound fibronectin receptors on cell surfaces. Finally, fibronectin is important in cell migration events during embryogenesis.

"Gastrointestinal inflammatory disorders" are a group of chronic disorders that cause inflammation and/or ulceration in the mucous membrane. These disorders include, for example, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis.

"Inflammatory Bowel Disease" or "IBD" is used interchangeably herein to refer to diseases of the bowel that cause inflammation and/or ulceration and includes without limitation Crohn's disease and ulcerative colitis.

"Crohn's disease (CD)" or "ulcerative colitis (UC)" are chronic inflammatory bowel diseases of unknown etiology. Crohn's disease, unlike ulcerative colitis, can affect any part of the bowel. The most prominent feature Crohn's disease is the granular, reddish-purple edmatous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual.

Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils.

Anti-inflammatory drugs sulfasalazine and 5-aminosalysylic acid (5-ASA) are useful for treating mildly active colonic Crohn's disease and is commonly perscribed to maintain remission of the disease. Metroidazole and ciprofloxacin are similar in efficacy to sulfasalazine and appear to be particularly useful for treating perianal disease. In more severe cases, corticosteroids are effective in treating active exacerbations and can even maintain remission. Azathioprine and 6-mercaptopurine have also shown success in patients who require chronic administration of cortico steroids. It is also possible that these drugs may play a role in the long-term prophylaxis. Unfortunately, there can be a very long delay (up to six months) before onset of action in some patients.

Antidiarrheal drugs can also provide symptomatic relief in some patients. Nutritional therapy or elemental diet can improve the nutritional status of patients and induce symtomatic improvement of acute disease, but it does not induce sustained clinical remissions. Antibiotics are used in treating secondary small bowel bacterial overgrowth and in treatment of pyogenic complications.

"Ulcerative colitis (UC)" afflicts the large intestine. The course of the disease may be continuous or relapsing, mild or severe. The earliest lesion is an inflammatory infiltration with abscess formation at the base of the crypts of Lieberkühn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis.

The clinical features of UC are highly variable, and the onset may be insidious or abrupt, and may include diarrhea, tenesmus and relapsing rectal bleeding. With fulminant involvement of the entire colon, toxic megacolon, a life-threatening emergency, may occur. Extraintestinal manifestations include arthritis, pyoderma gangrenoum, uveitis, and erythema nodosum.

Treatment for UC includes sulfasalazine and related salicylate-containing drugs for mild cases and corticosteroid drugs in severe cases. Topical administration of either salicylates or corticosteroids is sometimes effective, particularly when the disease is limited to the distal bowel, and is associated with decreased side effects compared with systemic use. Supportive measures such as administration of iron and antidiarrheal agents are sometimes indicated. Azathioprine, 6-mercaptopurine and methotrexate are sometimes also prescribed for use in refractory corticosteroid-dependent cases.

A "modification" of an amino acid residue/position, as used herein, refers to a change of a primary amino acid sequence as compared to a starting amino acid sequence, wherein the change results from a sequence alteration involving said amino acid residue/positions. For example, typical modifications include substitution of the residue (or at said position) with another amino acid (e.g., a conservative or non-conservative substitution), insertion of one or more (generally fewer than 5 or 3) amino acids adjacent to said residue/position, and deletion of said residue/position. An "amino acid substitution," or variation thereof, refers to the replacement of an existing amino acid residue in a predetermined (starting) amino acid sequence with a different amino acid residue. Generally and preferably, the modification results in alteration in at least one physicobiochemical activity of the variant polypeptide compared to a polypeptide comprising the starting (or "wild type") amino acid sequence. For example, in the case of an antibody, a physicobiochemical activity that is altered can be binding affinity, binding capability and/or binding effect upon a target molecule.

The term "amino acid" within the scope of the present invention is used in its broadest sense and is meant to include the naturally occurring L α-amino acids or residues. The commonly used one- and three-letter abbreviations for naturally occurring amino acids are used herein (Lehninger, A. L., Biochemistry, 2d ed., pp. 71-92, (Worth Publishers, New York, N.Y., 1975). The term includes D-amino acids as well as chemically modified amino acids such as amino acid analogs, naturally occurring amino acids that are not usually incorporated into proteins such as norleucine, and chemically synthesized compounds having properties known in the art to be characteristic of an amino acid. For example, analogs or mimetics of phenylalanine or proline, which allow the same conformational restriction of the peptide compounds as natural Phe or Pro are included within the definition of amino acid. Such analogs and mimetics are referred to herein as "functional equivalents" of an amino acid. Other examples of amino acids are listed by Roberts and Vellaccio, The Peptides Analysis, Synthesis, Biology, Gross and Meiehofer, Eds., Vol. 5, p. 341 (Academic Press, Inc., New York, N.Y., 1983), which is incorporated herein by reference. Where a single letter is used to designate one of the naturally occurring amino acid, the designations are as commonly found in the relevant literature (see, for example, Alberts, B. et al. Molecular Biology of the Cell, 3rd ed., Garland Publishing, Inc. 1994, page 57).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol Biol 293: 865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) *J. Mol Biol* 293:865-881. If the on-rate exceeds 106 $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25° C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of 1M ethanolamine to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$ See, e.g., Chen, Y., et al., (1999) *J. Mol Biol* 293:865-881. However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette. The "Kd" or "Kd value" according to this invention is in one embodiment measured by a radiolabeled antigen binding assay (RIA) performed with the Fab version of the antibody and antigen molecule as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol Biol* 293: 865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment, the Kd or Kd value is measured by using surface plasmon resonance assays using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) *J. Mol Biol* 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

In one embodiment, an "on-rate" or "rate of association" or "association rate" or "$k_{on}$" according to this invention is determined with the same surface plasmon resonance technique described above using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of 1M ethanolamine to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) *J. Mol Biol* 293:865-881. However, if the on-rate exceeds $10^6 M^{-1} S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

The phrase "substantially reduced," or "substantially different", as used herein, denotes a sufficiently high degree of difference between two numeric values (generally one associated with an antibody of the invention and the other associated with a reference/comparator antibody) such that one of skill in the art would consider the difference between the two values to be of statistical significance within the context of the biological characteristic measured by said values (e.g., Kd values, HAMA response). The difference between said two values is preferably greater than about 10%, preferably greater than about 20%, preferably greater than about 30%, preferably greater than about 40%, preferably greater than about 50% as a function of the value for the reference/comparator antibody.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table A below. The ALIGN-2 sequence comparison computer program was authored by Genentech, Inc. and the source code shown in Table A below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in FIG. 8 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Unless specifically stated otherwise, all % amino acid sequence identity values used herein are obtained as described in the immediately preceding paragraph using the ALIGN-2 computer program.

TABLE A

```
/*
*
* C-C increased from 12 to 15
* Z is average of EQ
* B is average of ND
* match with stop is _M; stop-stop = 0; J (joker) match = 0
*/
#define _M     -8      /* value of a match with a stop */
int     _day[26][26] = {
/*       A B C D E F G H I J K L M N O P Q R S T U V W X Y Z */
/* A */  { 2, 0,-2, 0, 0,-4, 1,-1,-1, 0,-1,-2,-1, 0,_M, 1, 0,-2, 1, 1, 0, 0,-6, 0,-3, 0},
/* B */  { 0, 3,-4, 3, 2,-5, 0, 1,-2, 0, 0,-3,-2, 2,_M,-1, 1, 0, 0, 0, 0,-2,-5, 0,-3, 1},
/* C */  {-2,-4,15,-5,-5,-4,-3,-3,-2, 0,-5,-6,-5,-4,_M,-3,-5,-4, 0,-2, 0,-2,-8, 0, 0,-5},
/* D */  { 0, 3,-5, 4, 3,-6, 1, 1,-2, 0, 0,-4,-3, 2,_M,-1, 2,-1, 0, 0, 0,-2,-7, 0,-4, 2},
/* E */  { 0, 2,-5, 3, 4,-5, 0, 1,-2, 0, 0,-3,-2, 1,_M,-1, 2,-1, 0, 0, 0,-2,-7, 0,-4, 3},
/* F */  {-4,-5,-4,-6,-5, 9,-5,-2, 1, 0,-5, 2, 0,-4,_M,-5,-5,-4,-3,-3, 0,-1, 0, 0, 7,-5},
/* G */  { 1, 0,-3, 1, 0,-5, 5,-2,-3, 0,-2,-4,-3, 0,_M,-1,-1,-3, 1, 0, 0,-1,-7, 0,-5, 0},
/* H */  {-1, 1,-3, 1, 1,-2,-2, 6,-2, 0, 0,-2,-2, 2,_M, 0, 3, 2,-1,-1, 0,-2,-3, 0, 0, 2},
/* I */  {-1,-2,-2,-2,-2, 1,-3,-2, 5, 0,-2, 2, 2,-2,_M,-2,-2,-2,-1, 0, 0, 4,-5, 0,-1,-2},
/* J */  { 0, 0, 0, 0, 0, 0, 0, 0, 0, 0, 0, 0, 0, 0,_M, 0, 0, 0, 0, 0, 0, 0, 0, 0, 0, 0},
/* K */  {-1, 0,-5, 0, 0,-5,-2, 0,-2, 0, 5,-3, 0, 1,_M,-1, 1, 3, 0, 0, 0,-2,-3, 0,-4, 0},
/* L */  {-2,-3,-6,-4,-3, 2,-4,-2, 2, 0,-3, 6, 4,-3,_M,-3,-2,-3,-3,-1, 0, 2,-2, 0,-1,-2},
/* M */  {-1,-2,-5,-3,-2, 0,-3,-2, 2, 0, 0, 4, 6,-2,_M,-2,-1, 0,-2,-1, 0, 2,-4, 0,-2,-1},
/* N */  { 0, 2,-4, 2, 1,-4, 0, 2,-2, 0, 1,-3,-2, 2,_M,-1, 1, 0, 1, 0, 0,-2,-4, 0,-2, 1},
/* O */  {_M,_M,_M,_M,_M,_M,_M,_M,_M,_M,_M,_M,_M,_M,_M,
0,_M,_M,_M,_M,_M,_M,_M,_M,_M,_M,_M},
/* P */  { 1,-1,-3,-1,-1,-5,-1, 0,-2, 0,-1,-3,-2,-1,_M, 6, 0, 0, 1, 0, 0,-1,-6, 0,-5, 0},
```

TABLE A-continued

```
/* Q */      { 0, 1,-5, 2, 2,-5,-1, 3,-2, 0, 1,-2,-1, 1,_M, 0, 4, 1,-1,-1, 0,-2,-5, 0,-4, 3},
/* R */      {-2, 0,-4,-1,-1,-4,-3, 2,-2, 0, 3,-3, 0, 0,_M, 0, 1, 6, 0,-1, 0,-2, 2, 0,-4, 0},
/* S */      { 1, 0, 0, 0, 0,-3, 1,-1,-1, 0, 0,-3,-2, 1,_M, 1,-1, 0, 2, 1, 0,-1,-2, 0,-3, 0},
/* T */      { 1, 0,-2, 0, 0,-3, 0,-1, 0, 0, 0,-1,-1, 0,_M, 0,-1,-1, 1, 3, 0, 0,-5, 0,-3, 0},
/* U */      { 0, 0, 0, 0, 0, 0, 0, 0, 0, 0, 0, 0, 0, 0,_M, 0, 0, 0, 0, 0, 0, 0, 0, 0, 0, 0},
/* V */      { 0,-2,-2,-2,-2,-1,-1,-2, 4, 0,-2, 2, 2,-2,_M,-1,-2,-2,-1, 0, 0, 4,-6, 0,-2,-2},
/* W */      {-6,-5,-8,-7,-7, 0,-7,-3,-5, 0,-3,-2,-4,-4,_M,-6,-5, 2,-2,-5, 0,-6,17, 0, 0,-6},
/* X */      { 0, 0, 0, 0, 0, 0, 0, 0, 0, 0, 0, 0, 0, 0,_M, 0, 0, 0, 0, 0, 0, 0, 0, 0, 0, 0},
/* Y */      {-3,-3, 0,-4,-4, 7,-5, 0,-1, 0,-4,-1,-2,-2,_M,-5,-4,-4,-3,-3, 0,-2, 0, 0,10,-4},
/* Z */      { 0, 1,-5, 2, 3,-5, 0, 2,-2, 0, 0,-2,-1, 1,_M, 0, 3, 0, 0, 0, 0,-2,-6, 0,-4, 4}
};
/*
*/
#include <stdio.h>
#include <ctype.h>
#define MAXJMP    16       /* max jumps in a diag */
#define MAXGAP    24       /* don't continue to penalize gaps larger than this */
#define JMPS      1024     /* max jmps in an path */
#define MX        4        /* save if there's at least MX-1 bases since last jmp */
#define DMAT      3        /* value of matching bases */
#define DMIS      0        /* penalty for mismatched bases */
#define DINS0     8        /* penalty for a gap */
#define DINS1     1        /* penalty per base */
#define PINS0     8        /* penalty for a gap */
#define PINS1     4        /* penalty per residue */
struct jmp {
        short          n[MAXJMP];      /* size of jmp (neg for dely) */
        unsigned short x[MAXJMP];      /* base no. of jmp in seq x */
};                                     /* limits seq to 2^16 -1 */
struct diag {
        int            score;          /* score at last jmp */
        long           offset;         /* offset of prev block */
        short          ijmp;           /* current jmp index */
        struct jmp     jp;             /* list of jmps */
};
struct path {
        int            spc;            /* number of leading spaces */
        short          n[JMPS];        /* size of jmp (gap) */
        int            x[JMPS];        /* loc of jmp (last elem before gap) */
};
char        *ofile;                    /* output file name */
char        *namex[2];                 /* seq names: getseqs( ) */
char        *prog;                     /* prog name for err msgs */
char        *seqx[2];                      /* seqs: getseqs( ) */
int         dmax;                      /* best diag: nw( ) */
int         dmax0;                     /* final diag */
int         dna;                       /* set if dna: main( ) */
int         endgaps;                       /* set if penalizing end gaps */
int         gapx, gapy;                /* total gaps in seqs */
int         len0, len1;                /* seq lens */
int         ngapx, ngapy;              /* total size of gaps */
int         smax;                      /* max score: nw( ) */
int         *xbm;                      /* bitmap for matching */
long        offset;                    /* current offset in jmp file */
struct  diag    *dx;                   /* holds diagonals */
struct  path    pp[2];                 /* holds path for seqs */
char        *calloc( ), *malloc( ), *index( ), *strcpy( );
char        *getseq( ), *g_calloc( );
/* Needleman-Wunsch alignment program
*
* usage: progs file1 file2
* where file1 and file2 are two dna or two protein sequences.
* The sequences can be in upper- or lower-case an may contain ambiguity
* Any lines beginning with ';', '>' or '<' are ignored
* Max file length is 65535 (limited by unsigned short x in the jmp struct)
* A sequence with 1/3 or more of its elements ACGTU is assumed to be DNA
* Output is in the file "align.out"
*
* The program may create a tmp file in /tmp to hold info about traceback.
* Original version developed under BSD 4.3 on a vax 8650
*/
#include "nw.h"
#include "day.h"
static   _dbval[26] = {
        1,14,2,13,0,0,4,11,0,0,12,0,3,15,0,0,0,5,6,8,8,7,9,0,10,0
};
```

TABLE A-continued

```
static      __pbval[26] = {
        1, 2|(1<<('D'-'A'))|(1<<('N'-'A')), 4, 8, 16, 32, 64,
        128, 256, 0xFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};
main(ac, av)
main
        int      ac;
        char     *av[ ];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? __dbval : __pbval;
        endgaps = 0;                       /* 1 to penalize endgaps */
        ofile = "align.out";               /* output file */
        nw( );          /* fill in the matrix, get the possible jmps */
        readjmps( );    /* get the actual jmps */
        print( );       /* print stats, alignment */
        cleanup(0);     /* unlink any tmp files */
}
/* do the alignment, return best score: main( )
* dna: values in Fitch and Smith, PNAS, 80, 1382-1386, 1983
* pro: PAM 250 values
* When scores are equal, we prefer mismatches to any gap, prefer
* a new gap to extending an ongoing gap, and prefer a gap in seqx
* to a gap in seq y.
*/
nw( )
nw
{
        char           *px, *py;             /* seqs and ptrs */
        int            *ndely, *dely;        /* keep track of dely */
        int            ndelx, delx;          /* keep track of delx */
        int            *tmp;                 /* for swapping row0, row1 */
        int            mis;                  /* score for each type */
        int            ins0, ins1;           /* insertion penalties */
        register       id;                   /* diagonal index */
        register       ij;                   /* jmp index */
        register       *col0, *col1;         /* score for curr, last row */
        register       xx, yy;               /* index into seqs */
        dx = (struct diag *)g__calloc("to get diags", len0+len1+1, sizeof(struct diag));
        ndely = (int *)g__calloc("to get ndely", len1+1, sizeof(int));
        dely = (int *)g__calloc("to get dely", len1+1, sizeof(int));
        col0 = (int *)g__calloc("to get col0", len1+1, sizeof(int));
        col1 = (int *)g__calloc("to get col1", len1+1, sizeof(int));
        ins0 = (dna)? DINS0 : PINS0;
        ins1 = (dna)? DINS1 : PINS1;
        smax = −10000;
        if (endgaps) {
                for (col0[0] = dely[0] = −ins0, yy = 1; yy <= len1; yy++) {
                        col0[yy] = dely[yy] = col0[yy−1] − ins1;
                        ndely[yy] = yy;
                }
                col0[0] = 0;     /* Waterman Bull Math Biol 84 */
        }
        else
                for (yy = 1; yy <= len1; yy++)
                        dely[yy] = −ins0;
        /* fill in match matrix
        */
        for (px = seqx[0], xx = 1; xx <= len0; px++, xx++) {
                /* initialize first entry in col
                */
                if (endgaps) {
                        if (xx == 1)
                                col1[0] = delx = −(ins0+ins1);
```

TABLE A-continued

```
                    else
                            col1[0] = delx = col0[0] – ins1;
                    ndelx = xx;
            }
            else {
                    col1[0] = 0;
                    delx = –ins0;
                    ndelx = 0;
            }
...nw
            for (py = seqx[1], yy = 1; yy <= len1; py++, yy++) {
                    mis = col0[yy–1];
                    if (dna)
                            mis += (xbm[*px–'A']&xbm[*py–'A'])? DMAT : DMIS;
                    else
                            mis += _day[*px–'A'][*py–'A'];
                    /* update penalty for del in x seq;
                     * favor new del over ongong del
                     * ignore MAXGAP if weighting endgaps
                     */
                    if (endgaps || ndely[yy] < MAXGAP) {
                            if (col0[yy] – ins0 >= dely[yy]) {
                                    dely[yy] = col0[yy] – (ins0+ins1);
                                    ndely[yy] = 1;
                            } else {
                                    dely[yy] –= ins1;
                                    ndely[yy]++;
                            }
                    } else {
                            if (col0[yy] – (ins0+ins1) >= dely[yy]) {
                                    dely[yy] = col0[yy] – (ins0+ins1);
                                    ndely[yy] = 1;
                            } else
                                    ndely[yy]++;
                    }
                    /* update penalty for del in y seq;
                     * favor new del over ongong del
                     */
                    if (endgaps || ndelx < MAXGAP) {
                            if (col1[yy–1] – ins0 >= delx) {
                                    delx = col1[yy–1] – (ins0+ins1);
                                    ndelx = 1;
                            } else {
                                    delx –= ins1;
                                    ndelx++;
                            }
                    } else {
                            if (col1[yy–1] – (ins0+ins1) >= delx) {
                                    delx = col1[yy–1] – (ins0+ins1);
                                    ndelx = 1;
                            } else
                                    ndelx++;
                    }
                    /* pick the maximum score; we're favoring
                     * mis over any del and delx over dely
                     */
...nw
                    id = xx – yy + len1 – 1;
                    if (mis >= delx && mis >= dely[yy])
                            col1[yy] = mis;
                    else if (delx >= dely[yy]) {
                            col1[yy] = delx;
                            ij = dx[id].ijmp;
                            if (dx[id].jp.n[0] && (!dna || (ndelx >= MAXJMP
                            && xx > dx[id].jp.x[ij]+MX) || mis > dx[id].score+DINS0))
{
                                    dx[id].ijmp++;
                                    if (++ij >= MAXJMP) {
                                            writejmps(id);
                                            ij = dx[id].ijmp = 0;
                                            dx[id].offset = offset;
                                            offset += sizeof(struct jmp) + sizeof(offset);
                                    }
                            }
                            dx[id].jp.n[ij] = ndelx;
                            dx[id].jp.x[ij] = xx;
                            dx[id].score = delx;
                    }
```

TABLE A-continued

```
                    else {
                            col1[yy] = dely[yy];
                            ij = dx[id].ijmp;
                if (dx[id].jp.n[0] && (!dna || (ndely[yy] >= MAXJMP
                                    && xx > dx[id].jp.x[ij]+MX) || mis > dx[id].score+DINS0))
{
                                        dx[id].ijmp++;
                                        if (++ij >= MAXJMP) {
                                                writejmps(id);
                                                ij = dx[id].ijmp = 0;
                                                dx[id].offset = offset;
                                                offset += sizeof(struct jmp) + sizeof(offset);
                                        }
                            }
                            dx[id].jp.n[ij] = -ndely[yy];
                            dx[id].jp.x[ij] = xx;
                            dx[id].score = dely[yy];
                    }
                    if (xx == len0 && yy < len1) {
                            /* last col
                             */
                            if (endgaps)
                                    col1[yy] -= ins0+ins1*(len1-yy);
                            if (col1[yy] > smax) {
                                    smax = col1[yy];
                                    dmax = id;
                            }
                    }
            }
            if (endgaps && xx < len0)
                    col1[yy-1] -= ins0+ins1*(len0-xx);
            if (col1[yy-1] > smax) {
                    smax = col1[yy-1];
                    dmax = id;
            }
            tmp = col0; col0 = col1; col1 = tmp;
    }
    (void) free((char *)ndely);
    (void) free((char *)dely);
    (void) free((char *)col0);
    (void) free((char *)col1);                          }
/*
 *
 * print( ) -- only routine visible outside this module
 *
 * static:
 * getmat( ) -- trace back best path, count matches: print( )
 * pr_align( ) -- print alignment of described in array p[ ]: print( )
 * dumpblock( ) -- dump a block of lines with numbers, stars: pr_align( )
 * nums( ) -- put out a number line: dumpblock( )
 * putline( ) -- put out a line (name, [num], seq, [num]): dumpblock( )
 * stars( ) - -put a line of stars: dumpblock( )
 * stripname( ) -- strip any path and prefix from a seqname
 */
#include "nw.h"
#define SPC     3
#define P_LINE          256     /* maximum output line */
#define P_SPC 3                 /* space between name or num and seq */
extern  _day[26][26];
int     olen;                   /* set output line length */
FILE    *fx;                    /* output file */
print( )
print
{
        int     lx, ly, firstgap, lastgap; /* overlap */
        if ((fx = fopen(ofile, "w")) == 0) {
                fprintf(stderr, "%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) { /* leading gap in x */
                pp[0].spc = firstgap = len1 - dmax - 1;
                ly -= pp[0].spc;
        }
```

TABLE A-continued

```
                else if (dmax > len1 – 1) {          /* leading gap in y */
                        pp[1].spc = firstgap = dmax – (len1 – 1);
                        lx –= pp[1].spc;
                }
                if (dmax0 < len0 – 1) {              /* trailing gap in x */
                        lastgap = len0 – dmax0 –1;
                        lx –= lastgap;
                }
                else if (dmax0 > len0 – 1) {         /* trailing gap in y */
                        lastgap = dmax0 – (len0 – 1);
                        ly –= lastgap;
                }
                getmat(lx, ly, firstgap, lastgap);
                pr_align( );
}
/*
* trace back the best path, count matches
*/
static
getmat(lx, ly, firstgap, lastgap)
getmat
        int       lx, ly;                            /* "core" (minus endgaps) */
        int       firstgap, lastgap;                 /* leading trailing overlap */
{
        int                 nm, i0, i1, siz0, siz1;
        char                outx[32];
        double              pct;
        register            n0, n1;
        register char       *p0, *p1;
        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0–'A']&xbm[*p1–'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }
        /* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
        fprintf(fx, "<gaps in first sequence: %d", gapx);
...getmat
        if (gapx) {
                (void) sprintf(outx, " (%d %s%s)",
                        ngapx, (dna)? "base":"residue", (ngapx == 1)? "":"s");
                fprintf(fx, "%s", outx);
```

TABLE A-continued

```
                fprintf(fx, ", gaps in second sequence: %d", gapy);
                if (gapy) {
                        (void) sprintf(outx, " (%d %s%s)",
                                ngapy, (dna)? "base":"residue", (ngapy == 1)? "":"s");
                        fprintf(fx, "%s", outx);
                }
                if (dna)
                        fprintf(fx,
                        "\n<score: %d (match = %d, mismatch = %d, gap penalty = %d + %d per
base)\n",
                                smax, DMAT, DMIS, DINS0, DINS1);
                else
                        fprintf(fx,
                        "\n<score: %d (Dayhoff PAM 250 matrix, gap penalty = %d + %d per
residue)\n",
                                smax, PINS0, PINS1);
                if (endgaps)
                        fprintf(fx,
                        "<endgaps penalized. left endgap: %d %s%s, right endgap: %d %s%s\n",
                                firstgap, (dna)? "base" : "residue", (firstgap == 1)? "" : "s",
                                lastgap, (dna)? "base" : "residue", (lastgap == 1)? "" : "s");
                else
                        fprintf(fx, "<endgaps not penalized\n");
}
static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE];         /* output line */
static char     star[P_LINE];   /* set by stars( ) */
/*
* print alignment of described in struct path pp[ ]
*/
static
pr_align( )
pr_align
{
                int             nn;     /* char count */
                int             more;
                register        i;
                for (i = 0, lmax = 0; i < 2; i++) {
                        nn = stripname(namex[i]);
                        if (nn > lmax)
                                lmax = nn;
                        nc[i] = 1;
                        ni[i] = 1;
                        siz[i] = ij[i] = 0;
                        ps[i] = seqx[i];
                        po[i] = out[i]; }
                for (nn = nm = 0, more = 1; more; ) {
...pr_align
                        for (i = more = 0; i < 2; i++) {
                                /*
                                * do we have more of this sequence?
                                */
                                if (!*ps[i])
                                        continue;
                                more++;
                                if (pp[i].spc) { /* leading space */
                                        *po[i]++ = ' ';
                                        pp[i].spc--;
                                }
                                else if (siz[i]) { /* in a gap */
                                        *po[i]++ = '-';
                                        siz[i]--;
                                }
                                else {          /* we're putting a seq element
                                                */
                                        *po[i] = *ps[i];
                                        if (islower(*ps[i]))
                                                *ps[i] = toupper(*ps[i]);
                                        po[i]++;
                                        ps[i]++;
                                        /*
                                        * are we at next gap for this seq?
                                        */
```

TABLE A-continued

```
                                if (ni[i] == pp[i].x[ij[i]]) {
                                        /*
                                         * we need to merge all gaps
                                         * at this location
                                         */
                                        siz[i] = pp[i].n[ij[i]++];
                                        while (ni[i] == pp[i].x[ij[i]])
                                                siz[i] += pp[i].n[ij[i]++];
                                }
                                ni[i]++;
                        }
                }
                if (++nn == olen || !more && nn) {
                        dumpblock( );
                        for (i = 0; i < 2; i++)
                                po[i] = out[i];
                        nn = 0;
                }
        }
}
/*
 * dump a block of lines, including numbers, stars: pr_align( )
 */
static
dumpblock( )
dumpblock
{
        register                i;
        for (i = 0; i < 2; i++)
                *po[i]-- = '\0';
...dumpblock
        (void) putc('\n', fx);
        for (i = 0; i < 2; i++) {
                if (*out[i] && (*out[i] != ' ' || *(po[i]) != ' ')) {
                        if (i == 0)
                                nums(i);
                        if (i == 0 && *out[1])
                                stars( );
                        putline(i);
                        if (i == 0 && *out[1])
                                fprintf(fx, star);
                        if (i == 1)
                                nums(i);
                }
        }
}
/*
 * put out a number line: dumpblock( )
 */
static
nums(ix)
nums
        int             ix;      /* index in out[ ] holding seq line */
{
        char            nline[P_LINE];
        register                i, j;
        register char   *pn, *px, *py;
        for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
```

TABLE A-continued

```
                for (pn = nline; *pn; pn++)
                        (void) putc(*pn, fx);
                (void) putc('\n', fx);
}
/*
 * put out a line (name, [num], seq, [num]): dumpblock( )
 */
static
putline(ix)
putline
                int     ix;                             {
...putline
                int             i;
                register char   *px;
                for (px = namex[ix], i = 0; *px && *px != ':'; px++, i++)
                        (void) putc(*px, fx);
                for (; i < lmax+P_SPC; i++)
                        (void) putc(' ', fx);
                /* these count from 1:
                 * ni[ ] is current element (from 1)
                 * nc[ ] is number at start of current line
                 */
                for (px = out[ix]; *px; px++)
                        (void) putc(*px&0x7F, fx);
                (void) putc('\n', fx);
}
/*
 * put a line of stars (seqs always in out[0], out[1]): dumpblock( )
 */
static
stars( )
stars
{
                int             i;
                register char   *p0, *p1, cx, *px;
                if (!*out[0] || (*out[0] == ' ' && *(po[0]) == ' ') ||
                    !*out[1] || (*out[1] == ' ' && *(po[1]) == ' '))
                        return;
                px = star;
                for (i = lmax+P_SPC; i; i--)
                        *px++ = ' ';
                for (p0 = out[0], p1 = out[1]; *p0 && *p1; p0++, p1++) {
                        if (isalpha(*p0) && isalpha(*p1)) {
                                if (xbm[*p0-'A']&xbm[*p1-'A']) {
                                        cx = '*';
                                        nm++;
                                }
                                else if (!dna && _day[*p0-'A'][*p1-'A'] > 0)
                                        cx = '.';
                                else
                                        cx = ' ';
                        }
                        else
                                cx = ' ';
                        *px++ = cx;
                }
                *px++ = '\n';
                *px = '\0';
}
/*
 * strip path or prefix from pn, return len: pr_align( )
 */
static
stripname(pn)
stripname
                char    *pn;    /* file name (may be path) */
{
                register char   *px, *py;
                py = 0;
                for (px = pn; *px; px++)
                        if (*px == '/')
                                py = px + 1;
                if (py)
                        (void) strcpy(pn, py);
                return(strlen(pn));
}
```

TABLE A-continued

```
/*
 * cleanup( ) -- cleanup any tmp file
 * getseq( ) -- read in seq, set dna, len, maxlen
 * g__calloc( ) -- calloc( ) with error checkin
 * readjmps( ) -- get the good jmps, from tmp file if necessary
 * writejmps( ) -- write a filled array of jmps to a tmp file: nw( )
 */
#include "nw.h"
#include <sys/file.h>
char      *jname = "/tmp/homgXXXXXX";       /* tmp file for jmps */
FILE      *fj;
int       cleanup( );                        /* cleanup tmp file */
long      lseek( );
/*
 * remove any tmp file if we blow
 */
cleanup(i)
cleanup
          int       i;
{
          if (fj)
                    (void) unlink(jname);
          exit(i);
}
/*
 * read, return ptr to seq, set dna, len, maxlen
 * skip lines starting with ';', '<', or '>'
 * seq in upper or lower case
 */
char      *
getseq(file, len)
getseq
          char      *file;     /* file name */
          int       *len;      /* seq len */
{
          char                 line[1024], *pseq;
          register char        *px, *py;
          int                  natgc, tlen;
          FILE                 *fp;
          if ((fp = fopen(file,"r")) == 0) {
                    fprintf(stderr,"%s: can't read %s\n", prog, file);
                    exit(1);
          }
          tlen = natgc = 0;
          while (fgets(line, 1024, fp)) {
                    if (*line == ';' || *line == '<' || *line == '>')
                              continue;
                    for (px = line; *px != '\n'; px++)
                              if (isupper(*px) || islower(*px))
                                        tlen++;
          }
          if ((pseq = malloc((unsigned)(tlen+6))) == 0) {
                    fprintf(stderr,"%s: malloc( ) failed to get %d bytes for %s\n", prog, tlen+6, file);
                    exit(1);
          }
          pseq[0] = pseq[1] = pseq[2] = pseq[3] = '\0';
...getseq
          py = pseq + 4;
          *len = tlen;
          rewind(fp);
          while (fgets(line, 1024, fp)) {
                    if (*line == ';' || *line == '<' || *line == '>')
                              continue;
                    for (px = line; *px != '\n'; px++) {
                              if (isupper(*px))
                                        *py++ = *px;
                              else if (islower(*px))
                                        *py++ = toupper(*px);
                              if (index("ATGCU",*(py-1)))
                                        natgc++;
                    }
          }
          *py++ = '\0';
          *py = '\0';
          (void) fclose(fp);
          dna = natgc > (tlen/3);
          return(pseq+4);
}
```

TABLE A-continued

```
char       *
g_calloc(msg, nx, sz)
g_calloc
        char       *msg;             /* program, calling routine */
        int        nx, sz;           /* number and size of elements */
{
        char             *px, *calloc( );
        if ((px = calloc((unsigned)nx, (unsigned)sz)) == 0) {
                if (*msg) {
                        fprintf(stderr, "%s: g_calloc( ) failed %s (n=%d, sz=%d)\n", prog, msg,
nx, sz);
                        exit(1);
                }
        }
        return(px);
}
/*
 * get final jmps from dx[ ] or tmp file, set pp[ ], reset dmax: main( )
 */
readjmps( )
readjmps
{
        int              fd = -1;
        int              siz, i0, i1;
        register         i, j, xx;
        if (fj) {
                (void) fclose(fj);
                if ((fd = open(jname, O_RDONLY, 0)) < 0) {
                        fprintf(stderr, "%s: can't open( ) %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
...readjmps
                        if (j < 0 && dx[dmax].offset && fj) {
                                (void) lseek(fd, dx[dmax].offset, 0);
                                (void) read(fd, (char *)&dx[dmax].jp, sizeof(struct jmp));
                                (void) read(fd, (char *)&dx[dmax].offset,
sizeof(dx[dmax].offset));
                                dx[dmax].ijmp = MAXJMP-1;
                        }
                        else
                                break;
                }
                if (i >= JMPS) {
                        fprintf(stderr, "%s: too many gaps in alignment\n", prog);
                        cleanup(1);
                }
                if (j >= 0) {
                        siz = dx[dmax].jp.n[j];
                        xx = dx[dmax].jp.x[j];
                        dmax += siz;
                        if (siz < 0) {             /* gap in second seq */
                                pp[1].n[i1] = -siz;
                                xx += siz;
                                /* id = xx - yy + len1 - 1
                                 */
                                pp[1].x[i1] = xx - dmax + len1 - 1;
                                gapy++;
                                ngapy -= siz;
/* ignore MAXGAP when doing endgaps */
                                siz = (-siz < MAXGAP || endgaps)? -siz : MAXGAP;
                                i1++;
                        }
                        else if (siz > 0) {        /* gap in first seq */
                                pp[0].n[i0] = siz;
                                pp[0].x[i0] = xx;
                                gapx++;
                                ngapx += siz;
/* ignore MAXGAP when doing endgaps */
                                siz = (siz < MAXGAP || endgaps)? siz : MAXGAP;
                                i0++;
                        }
                }
                else
                        break;
        }
```

TABLE A-continued

```
        /* reverse the order of jmps
         */
        for (j = 0, i0--; j < i0; j++, i0--) {
                i = pp[0].n[j]; pp[0].n[j] = pp[0].n[i0]; pp[0].n[i0] = i;
                i = pp[0].x[j]; pp[0].x[j] = pp[0].x[i0]; pp[0].x[i0] = i;
        }
        for (j = 0, i1--; j < i1; j++, i1--) {
                i = pp[1].n[j]; pp[1].n[j] = pp[1].n[i1]; pp[1].n[i1] = i;
                i = pp[1].x[j]; pp[1].x[j] = pp[1].x[i1]; pp[1].x[i1] = i;
        }
        if (fd >= 0)
                (void) close(fd);
        if (fj) {
                (void) unlink(jname);
                fj = 0;
                offset = 0;
        }                                       }
/*
 * write a filled jmp struct offset of the prev one (if any): nw( )
 */
writejmps(ix)
writejmps
        int     ix;
{
        char    *mktemp( );
        if (!fj) {
                if (mktemp(jname) < 0) {
                        fprintf(stderr, "%s: can't mktemp( ) %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
```

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR.sub.2 ("amidate"), P(O)R, P(O)OR', CO or CH.sub.2 ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The terms "antibody" and "immunoglobulin" are used interchangeably in the broadest sense and include monoclonal antibodies (for example, full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide. An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VL subgroup I consensus framework" comprises the consensus sequence obtained from the amino acid sequences in variable light kappa subgroup I of Kabat et al. In one embodiment, the VL subgroup I consensus framework amino acid sequence comprises at least a portion or all of each of the following sequences:

```
DIQMTQSPSSLSASVGDRVTITC-          (SEQ ID NO:34)

L1-WYQQKPGKAPKLLI-                (SEQ ID NO:35)

L2-GVPSRFSGSGSGTDFTLTISSLQPEDFATYYC- (SEQ ID NO:36)

L3-FGQGTKVEIKR.                   (SEQ ID NO:37)
```

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences:

```
EVQLVESGGGLVQPGGSLRLSCAAS-        (SEQ ID NO:38)

H1-WVRQAPGKGLEWV-                 (SEQ ID NO:39)

H2-RFTISRDNSKNTLYLQMNSLRAEDTAVYYCA- (SEQ ID NO:40)

H3-WGQGTLVTVSS.                   (SEQ ID NO:41)
```

An "unmodified human framework" is a human framework which has the same amino acid sequence as the acceptor human framework, e.g. lacking human to non-human amino acid substitution(s) in the acceptor human framework.

An "altered hypervariable region" for the purposes herein is a hypervariable region comprising one or more (e.g. one to about 16) amino acid substitution(s) therein.

An "un-modified hypervariable region" for the purposes herein is a hypervariable region having the same amino acid sequence as a non-human antibody from which it was derived, i.e. one which lacks one or more amino acid substitutions therein.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

TABLE 1

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 Kabat numbering | H31-H35B | H26-H35B | H26-H32 | H30-H35B |

TABLE 1-continued

| Loop | Kabat | AbM | Chothia | Contact |
|---|---|---|---|---|
| H1 Chothia numbering | H31-H35 | H26-H35 | H26-H32 | H30-H35 |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 49-56 or 50-56 or 52-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues as herein defined.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it bind. Preferred blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections.

An "autoimmune disorder" or "autoimmune disease" as used interchangeably herein is a non-malignant disease or disorder arising from and directed against an individual's own tissues. The autoimmune diseases described herein specifically exclude malignant or cancerous diseases or conditions, particularly excluding B cell lymphoma, acute lymphoblastic leukemia (ALL), chronic lymphocytic leukemia (CLL), Hairy cell leukemia, and chronic myeloblastic leukemia. Examples of autoimmune diseases or disorders include, but are not limited to, inflammatory responses such as inflammatory skin diseases including psoriasis and dermatitis (for example, atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitis); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc.

The term "gastrointestinal inflammatory disorders" is a group of chronic disorders that cause inflammation and/or ulceration in the mucous membrane. As such, the term includes inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

Dysregulation of angiogenesis can lead to many disorders that can be treated by compositions and methods of the invention. These disorders include both non-neoplastic and neoplastic conditions. Neoplastics include but are not limited those described above. Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $R^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell whose growth is dependent upon beta7 activation either in vitro or in vivo. Thus, the growth inhibitory agent may be one which significantly reduces the percentage of beta7-dependent cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

Compounds useful in combination therapy with an antagonist anti-beta7 antibody of the invention include antibodies (including without limitation other anti-beta7 antagonist antibodies (Fib 21, 22, 27, 30 (Tidswell, M. (1997) supra) or humanized derivatives thereof), anti-alpha4 antibodies (such as ANTEGEN®), anti-TNF (REMICADE®)) or non-protein compounds including without limitation 5-ASA compounds ASACOL®), PENTASA™, ROWASA™, COLAZAL™, and other compounds such as Purinethol and steroids such as prednisone. In an embodiment, the invention encompasses a method of treating a patient, such as a human patient, with the antagonist anti-beta7 antibody of the invention alone or in combination with a second compound that is also useful in treating inflammation. In one embodiment the second compound is selected from the group consisting of Fib 21, 22, 27, 30, or humanized derivatives thereof), anti-alpha4 antibodies, ANTEGEN®, anti-TNF, REMICADE®, 5-ASA compounds, ASACOL®, PENTASA™, ROWASA™, COLAZAL™, Purinethol, steroids, and prednisone. In one embodiment of the invention, administration of the antagonist anti-beta7 antibody of the invention substantially reduces the dose of the second compound. In one embodiment, said reduction in the dose of the second compound is at least 30%, at least 40%, at least 50%, at least 60%, at least 70%, at least 80%, at least 90%, at least 95%. In one embodiment of the invention, the combination of the antibody of the invention and the reduced dose of the second compound relieves symptoms in the patient to substantially the same degree or better than administration of the second compound alone.

Generating Variant Antibodies Exhibiting Reduced or Absence of HAMA Response

Reduction or elimination of a HAMA (human anti-mouse (also applicable to human anti-rat or human anti-human) response is a significant aspect of clinical development of suitable therapeutic agents. See, e.g., Khaxzaeli et al., J. Natl. Cancer Inst. (1988), 80:937; Jaffers et al., Transplantation (1986), 41:572; Shawler et al., J. Immunol. (1985), 135:1530; Sears et al., J. Biol. Response Mod. (1984), 3:138; Miller et al., Blood (1983), 62:988; Hakimi et al., J. Immunol. (1991), 147:1352; Reichmann et al., Nature (1988), 332:323; Junghans et al., Cancer Res. (1990), 50:1495. As described herein, the invention provides antibodies that are humanized such that HAMA response is reduced or eliminated. Variants of these antibodies can further be obtained using routine methods known in the art, some of which are further described below.

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), preferably the acceptor human frameworks are from, or derived from, a human consensus framework sequence as such frameworks have been demonstrated to have minimal, or no, immunogenicity in human patients.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor.

In one embodiment, human consensus frameworks herein are from, or derived from, VH subgroup III and/or VL kappa subgroup I consensus framework sequences.

Thus, the VH acceptor human framework may comprise one, two, three or all of the following framework sequences:
FR1 comprising EVQLVESGGGLVQPGGSLRLSCAAS (SEQ ID NO:38),
FR2 comprising WVRQAPGKGLEWV (SEQ ID NO:39),
FR3 comprising FR3 comprises RFTISX1DX2SKNTX3YLQMNSLRAEDTAVYYCA (SEQ ID NO:42), wherein X1 is A or R, X2 is T or N, and X3 is A, L, or F,
FR4 comprising WGQGTLVTVSS (SEQ ID NO:41).
Examples of VH consensus frameworks include:
human VH subgroup I consensus framework minus Kabat CDRs (SEQ ID NO:19);
human VH subgroup I consensus framework minus extended hypervariable regions (SEQ ID NOs:20-22);
human VH subgroup II consensus framework minus Kabat CDRs (SEQ ID NO:48);
human VH subgroup II consensus framework minus extended hypervariable regions (SEQ ID NOs:49-51);
human VH subgroup III consensus framework minus Kabat CDRs (SEQ ID NO:52);
human VH subgroup III consensus framework minus extended hypervariable regions (SEQ ID NO:53-55);
human VH acceptor framework minus Kabat CDRs (SEQ ID NO:56);
human VH acceptor framework minus extended hypervariable regions (SEQ ID NOs:57-58);
human VH acceptor 2 framework minus Kabat CDRs (SEQ ID NO:59); or
human VH acceptor 2 framework minus extended hypervariable regions (SEQ ID NOs:60-62).

In one embodiment, the VH acceptor human framework comprises one, two, three or all of the following framework sequences:
FR1 comprising EVQLVESGGGLVQPGGSLRLSCAAS (SEQ ID NO:38),
FR2 comprising WVRQAPGKGLEWV (SEQ ID NO:39),
FR3 comprising FR3 comprises RFTISADTSKNTAYLQMNSLRAEDTAVYYCA (SEQ ID NO:43), RFTISRDTSKNTAYLQMNSLRAEDTAVYYCA (SEQ ID NO:44), RFTISRDTSKNTFYLQMNSLRAEDTAVYYCA (SEQ ID NO:45), RFTISADTSKNTFYLQMNSLRAEDTAVYYCA (SEQ ID NO:46),
FR4 comprising WGQGTLVTVSS (SEQ ID NO:41).

The VL acceptor human framework may comprise one, two, three or all of the following framework sequences:
FR1 comprising DIQMTQSPSSLSASVGDRVTITC (SEQ ID NO:34),
FR2 comprising WYQQKPGKAPKLLI (SEQ ID NO:35),
FR3 comprising GVPSRFSGSGSGTDFTLTISSLQPEDFATYYC (SEQ ID NO:36),
FR4 comprising FGQGTKVEIKR (SEQ ID NO:37).
Examples of VL consensus frameworks include:
human VL kappa subgroup I consensus framework (SEQ ID NO:14);
human VL kappa subgroup I consensus framework (extended HVR-L2) (SEQ ID NO:15);
human VL kappa subgroup II consensus framework (SEQ ID NO:16);
human VL kappa subgroup III consensus framework (SEQ ID NO:17); or
human VL kappa subgroup IV consensus framework (SEQ ID NO:18)

While the acceptor may be identical in sequence to the human framework sequence selected, whether that is from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-34 (L1), 49-56 (L2) and 89-97 (L3), 26-35 (H1), 50-65 or 49-65 (H2) and 93-102, 94-102, or 95-102 (H3).

While "incorporation" of hypervariable region residues is discussed herein, it will be appreciated that this can be achieved in various ways, for example, nucleic acid encoding the desired amino acid sequence can be generated by mutating nucleic acid encoding the mouse variable domain sequence so that the framework residues thereof are changed to acceptor human framework residues, or by mutating nucleic acid encoding the human variable domain sequence so that the hypervariable domain residues are changed to non-human residues, or by synthesizing nucleic acid encoding the desired sequence, etc.

In the examples herein, hypervariable region-grafted variants were generated by Kunkel mutagenesis of nucleic acid encoding the human acceptor sequences, using a separate oligonucleotide for each hypervariable region. Kunkel et al., *Methods Enzymol.* 154:367-382 (1987). Appropriate changes can be introduced within the framework and/or hypervariable region, using routine techniques, to correct and re-establish proper hypervariable region-antigen interactions.

Phage(mid) display (also referred to herein as phage display in some contexts) can be used as a convenient and fast method for generating and screening many different potential variant antibodies in a library generated by sequence randomization. However, other methods for making and screening altered antibodies are available to the skilled person.

Phage(mid) display technology has provided a powerful tool for generating and selecting novel proteins which bind to a ligand, such as an antigen. Using the techniques of phage (mid) display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, S., *Proteins*, 8:309 (1990); Lowman and Wells, *Methods: A Companion to Methods in Enzymology*, 3:205 (1991)). In a monovalent phagemid display system, the gene fusion is expressed at low levels and wild type gene III proteins are also expressed so that infectivity of the particles is retained. Methods of generating peptide libraries and screening those libraries have been disclosed in many patents (e.g. U.S. Pat. No. 5,723,286, U.S. Pat. No. 5,432,018, U.S. Pat. No. 5,580,717, U.S. Pat. No. 5,427,908 and U.S. Pat. No. 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage(mid) display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

Methods of substituting an amino acid of choice into a template nucleic acid are well established in the art, some of which are described herein. For example, hypervariable region residues can be substituted using the Kunkel method. See, for example, Kunkel et al., *Methods Enzymol.* 154:367-382 (1987).

The sequence of oligonucleotides includes one or more of the designed codon sets for the hypervariable region residues to be altered. A codon set is a set of different nucleotide triplet sequences used to encode desired variant amino acids. Codon sets can be represented using symbols to designate particular nucleotides or equimolar mixtures of nucleotides as shown in below according to the IUB code.

IUB CODES
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T) H
N (A or C or G or T)

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al. *Nucleic Acids Res.* 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., *Proc. Nat'l. Acad. Sci. USA,* 75:5765 (1978).

The DNA template is generated by those vectors that are either derived from bacteriophage M13 vectors (the commercially available M13 mp18 and M13 mp19 vectors are suitable), or those vectors that contain a single-stranded phage origin of replication as described by Viera et al., *Meth. Enzymol.,* 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. *Meth. Enzymol.*, 153:3 (1987). Thus, the DNA that is to be mutated must be inserted into one of these vectors in order to generate single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent accessible and highly diverse positions in a hypervariable region. As described above, a codon set is a set of different nucleotide triplet sequences used to encode desired variant amino acids.

Antibody selectants that meet the desired criteria, as selected through appropriate screening/selection steps can be isolated and cloned using standard recombinant techniques.

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

Generating Antibodies Using Prokaryotic Host Cells:
Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene,* 159:203 (1995).

The present invention provides an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology,* vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kan$^R$ (U.S. Pat. No. 5,639,635). Other strains and derivatives thereof, such as *E. coli* 294 (ATCC 31,446), *E. coli* B, *E. coli*$_\lambda$ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., *Proteins,* 8:309-314 (1990). It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, for example, Simmons et al., *J. Immunol. Methods* (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275:17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance*, 2:63-72 (1996).

In one embodiment, *E. coli* strains deficient for proteolytic enzymes and transformed with plasmids overexpressing one or more chaperone proteins are used as host cells in the expression system of the invention.

Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41kD cell wall protein from *Staphylococcus aureas* which binds with a high affinity to the Fc region of antibodies. Lindmark et al (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually alleukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma-Aldrich, St. Louis, Mo., USA), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Activity Assays

The antibodies of the present invention can be characterized for their physical/chemical properties and biological functions by various assays known in the art.

The purified immunoglobulins can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the immunoglobulins produced herein are analyzed for their biological activity. In some embodiments, the immunoglobulins of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. An illustrative antigen binding assay is provided below in the Examples section.

In one embodiment, the present invention contemplates an altered antibody that possesses some but not all effector functions, which make it a desired candidate for many applications in which the half life of the antibody in vivo is important yet certain effector functions (such as complement and ADCC) are unnecessary or deleterious. In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol* 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998). C1q binding assays may also be carried out to confirm that the antibody is unable to bind C1q and hence lacks CDC activity. To assess complement activation, a CDC assay, for example as described in Gazzano-Santoro et al., *J. Immunol. Methods* 202:163 (1996), may be performed. FcRn binding and in vivo clearance/half life determinations can also be performed using methods known in the art, for example those described in the Examples section.

Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Antibody Variants

In one aspect, the invention provides antibody fragment comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, for example, as described in U.S. Pat. No. 5,731,168.

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions" in Table 2, or as further described below in reference to amino acid classes, may be introduced and the products screened.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |

TABLE 2-continued

| Original Residue | Exemplary Substitutions | Preferred Substitutions |
|---|---|---|
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (O)
(3) acidic: Asp (D), Glu (E)
(4) basic: Lys (K), Arg (R), His (H)

Alternatively, naturally occurring residues may be divided into groups based on common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody used in methods of the invention may comprise one or more alterations as compared to the wild type counterpart antibody, for example in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), for example, as described in WO99/51642. See also Duncan & Winter Nature 322:738-40 (1988); U.S. Pat. No. 5,648,260; U.S. Pat. No. 5,624,821; and WO94/29351 concerning other examples of Fc region variants.

Immunoconjugates

The invention also pertains to immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19): 1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of an anti-prostate specific membrane antigen (PSMA) monoclonal antibody linked to the maytansinoid drug moiety, DM1, is under development for the potential treatment of prostate tumors. The auristatin peptides, auristatin E (AE), monomethylauristatin E (MMAE), and synthetic analogs of dolastatin, were conjugated to chimeric monoclonal antibodies cBR96 (specific to Lewis Y on carcinomas) and cAC10 (specific to CD30 on hematological malignancies) (Doronina et al. (2003) Nature Biotechnology 21 (7):778-784; and Francisco, et al. (2003) Blood, 102, 1458-1465) and are under therapeutic development. Other compounds for use as drug conjugate cytotoxic agents include without limitation auristatin E (AE), MMAF (a variant of auristatin E (MMAE) with a phenylalanine at the C-terminus of the drug), and AEVB (auristatin E valeryl benzylhydrazone, an acid labile linker through the C-terminus of AE). Useful conjugate linkers for attaching a drug to an antibody include without limitation MC (maleimidocaproyl), Val Cit (valine-citrulline, dipeptide site in protease cleavable linker), Citrulline (2-amino-5-ureido pentanoic acid), PAB (p-aminobenzylcarbamoyl, a "self immolative" portion of linker), Me (N-methyl-valine citrulline where the linker peptide bond has been modified to prevent its cleavage by cathepsin B), MC (PEG)6-OH (maleimidocaproyl-polyethylene glycol, attached to antibody cysteines), SPP (N-Succinimidyl 4-(2-pyridylthio) pentanoate), and SMCC (N-Succinimidyl 4-(N-maleimidomethyl)cyclohexane-1 carboxylate). These and other useful drug conjugates and their preparation are disclosed, for example, in Doronina, S. O. et al., Nature Biotechnology 21:778-794 (2003), incorporated herein by reference in its entirety. Particularly preferred linker molecules include, for example, N-succinimidyl 3-(2-pyridyldithio)propionate (SPDP) (see, e.g., Carlsson et al., Biochem. J., 173, 723-737 (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), N-succinimidyl 4-(N-maleimidomethyl)cyclohe-xane-1-carboxylate (SMCC) (see, e.g., Yoshitake et al., Eur. J. Biochem., 101, 395-399 (1979)), and N-succinimidyl 4-methyl-4-[2-(5-nitro-pyridyl)—dithio]pentanoate (SMNP) (see, e.g., U.S. Pat. No. 4,563,304).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothecene, and CC1065, and the derivatives of these toxins that have toxin activity, are also contemplated herein.

Maytansine and Maytansinoids

In one embodiment, an antibody (full length or fragments) of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866;

4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-Maytansinoid Conjugates (Immunoconjugates)

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^1$, $\alpha_2^1$, $\alpha_3^1$, N-acetyl-$\gamma_1^1$, PSAG and $\theta^1_1$, (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053, 394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR)

imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208, 020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

$$Ab\text{-}(L\text{-}D)_p \qquad I$$

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, *Bioconjugate Techniques*). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Pharmaceutical Formulations

Therapeutic formulations comprising an antibody of the invention are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the present invention may be used in, for example, in vitro, ex vivo and in vivo therapeutic methods. Antibodies of the invention can be used as an antagonist to partially or fully block the specific antigen activity in vitro, ex vivo and/or in vivo. Moreover, at least some of the antibodies of the invention can neutralize antigen activity from other species. Accordingly, the antibodies of the invention can be used to inhibit a specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, the antibody of the invention can be used for inhibiting antigen activities by contacting the antibody with the antigen such that antigen activity is inhibited. Preferably, the antigen is a human protein molecule.

In one embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. Preferably, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the immunoglobulin cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Blocking antibodies of the invention that are therapeutically useful include, for example but are not limited to, anti-HER2, anti-VEGF, anti-IgE, anti-CD11, anti-interferon and anti-tissue factor antibodies. The antibodies of the invention can be used to treat, inhibit, delay progression of, prevent/delay recurrence of, ameliorate, or prevent diseases, disorders or conditions associated with abnormal expression and/or activity of one or more antigen molecules, including but not limited to malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

In one aspect, a blocking antibody of the invention is specific to a ligand antigen, and inhibits the antigen activity by blocking or interfering with the ligand-receptor interaction involving the ligand antigen, thereby inhibiting the corresponding signal pathway and other molecular or cellular events. The invention also features receptor-specific antibodies which do not necessarily prevent ligand binding but interfere with receptor activation, thereby inhibiting any responses that would normally be initiated by the ligand binding. The invention also encompasses antibodies that either preferably or exclusively bind to ligand-receptor complexes. An antibody of the invention can also act as an agonist of a particular antigen receptor, thereby potentiating, enhancing or activating either all or partial activities of the ligand-mediated receptor activation.

In certain embodiments, an immunoconjugate comprising an antibody conjugated with a cytotoxic agent is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, chemotherapeutic agent(s) (including cocktails of chemotherapeutic agents), other cytotoxic agent(s), anti-angiogenic agent(s), cytokines, and/or growth inhibitory agent(s). Where an antibody of the invention inhibits tumor growth, it may be particularly desirable to combine it with one or more other therapeutic agent(s) which also inhibits tumor growth. For instance, an antibody of the invention may be combined with an anti-VEGF antibody (e.g., AVASTIN) and/or anti-ErbB antibodies (e.g. HERCEPTIN® anti-HER2 antibody) in a treatment scheme, e.g. in treating any of the diseases described herein, including colorectal cancer, metastatic breast cancer and kidney cancer. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the antibody of the invention can occur prior to, and/or following, administration of the adjunct therapy or therapies.

The antibody of the invention (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, for example by injections, such as intravenous or subcutaneous injections, depending in part on whether the administration is brief or chronic.

The antibody composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of an antibody of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody is an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein, wherein the composition comprises a further cytotoxic agent. The article of manufacture in this embodiment of the invention may further comprise a package insert indicating that the first and second antibody compositions can be used to treat a particular condition, for example cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

The examples herein describe the generation of humanized anti-beta7 antibodies from a rat anti-mouse antibody that binds to the beta7 subunit of the alpha4beta7 integrin.

Example 1

Humanization of a Beta7 Antagonist Antibody

Materials and Methods

Residue numbers are according to Kabat (Kabat et al., *Sequences of proteins of immunological interest*, 5th Ed., Public Health Service, National Institutes of Health, Bethesda, Md. (1991)). Single letter amino acid abbreviations are used. DNA degeneracies are represented using the IUB code (N=A/C/G/T, D=A/G/T, V=A/C/G, B=C/G/T, H=A/C/T, K=G/T, M=A/C, R=A/G, S=G/C, W=A/T, Y=C/T).

Direct hypervariable region grafts onto the acceptor human consensus framework—The phagemid used for this work, pVO350-2b, was a monovalent Fab-g3 display vector having 2 open reading frames under control of the phoA promoter, essentially as described in Lee et al., *J. Mol. Biol.* (2004), 340(5):1073-93. The first open reading frame consists of the stII signal sequence fused to the VL and CH1 domains of the acceptor light chain and the second consists of the stII signal sequence fused to the VH and CH1 domains of the acceptor heavy chain followed by a truncated form of the minor phage coat protein P3 (Lowman, H. et al. (1990) Biochemistry 30:10832).

The VL and VH domains from rat Fib504 (antibody FIB504.64 produced by hybridoma ATCC HB-293, American Type Culture Collection (ATCC), P.O. Box 1549, Manassas, Va. 20108, USA) were aligned with the human consensus kappa I (huKI) and human subgroup III consensus VH (huIII) domains. To make the hypervariable region (HVR) grafts, the following frameworks were used: HuKI was used for the light chain variable domain framework (see FIGS. 1A and 7). For the heavy chain variable domain framework, the acceptor VH framework, a modified human subgroup III (humIII) consensus VH domain which differs from the humIII sequence at 3 positions: R71A, N73T, and L78A may be used (see Carter et al., Proc. Natl. Acad. Sci. USA 89:4285 (1992)) (see FIG. 1B). In generation of antibodies of the present invention, the 504K-RF graft was also prepared from the modified human subgroupIII consensus VH domain by making the following amino acid substitutions: A71R and A78F.

Hypervariable regions from rat Fib504 (produced by hybridoma ATCC HB-293) antibody were engineered into the acceptor human subgroup III consensus VH framework to generate a direct HVR-graft (Fib504graft) (see FIG. 1B). In the VL domain the following regions from rat Fib504 were grafted to the human consensus acceptor, huKI: positions 24-34 (L1), 50-56 (L2) and 89-97 (L3) (FIG. 1A). In the VH domain, positions 26-35 (H1), 49-65 (H2) and 94-102 (H3) were grafted (FIG. 1B). In addition a second HVR graft, Fib504 Kgraft, was constructed that also included within the HVR, VL position 49, based on an extended definition for L2 (see MacCallum et al. *J. Mol. Biol.* 262: 732-745 (1996)). MacCallum et al. have analyzed antibody and antigen complex crystal structures and found position 49 of the light chain and positions 49 and 94 of the heavy chain are part of the antigen contact region thus, these positions were included in the definitions of HVR-L2, HVR-H2 and HVR-H3 for humanized anti-beta7 antibodies disclosed herein.

The direct-graft variants were generated by Kunkel mutagenesis (Kunkel et al. (1987) supra) using a separate oligonucleotide for each hypervariable region. Correct clones were assessed by DNA sequencing.

Soft Randomization of the Hypervariable Regions:—

The process of "soft randomization" (see U.S. Application Ser. No. 60/545,840) refers a procedure for biased mutagensis of a selected protein sequence, such as a hypervariable region of an antibody. The method maintains a bias towards the murine, rat, or other starting hypervariable region sequence, while introducing an approximately 10-50 percent mutation at each selected position. This technique increases the capacity of the library screening employed and avoids a change in the antigen epitope recognized by the antibody. According to this soft randomization technique, sequence diversity is introduced into each hypervariable region using a strategy that maintains a bias towards the murine hypervariable region sequence. This was accomplished using a poisoned oligonucleotide synthesis strategy first described by Gallop et al., *J. Med. Chem.* 37:1233-1251 (1994). However, other methods for maintaining a bias towards the non-human hypervariable region residue are available, such as error prone PCR, DNA shuffling, etc.

According to the method used herein, for a given position within a hypervariable region to be mutated, the codon encoding the wild-type amino acid is poisoned with a mixture (e.g. a 70-10-10-10 mixture) of nucleotides resulting in an approximately 50 percent mutation rate at each selected hypervariable region position. To achieve this, the codon encoding the wild-type hypervariable region amino acid to be mutated is synthesized with a low level of contaminating mixture of the other three nucleotides, such as a 70-10-10-10 mixture of nucleotides. Thus, by way of example, for soft randomization of PRO (CCG), the first position synthesized is a mixture of 70% C, and 10% each of G, T and A; the second position is a mixture of 70% C, and 10% each of A, G, and T; and the third position is a mixture of 70% G, and 10% each of A, C and T. It is understood that the bias can be adjusted up or down depending upon the codon being synthesized at a given position, the number of codons that code for a particular amino acid, and the degree that oligonucleotide synthesis is poisoned by the nucleotide composition of the synthesis mixture.

Soft randomized oligonucleotides can be patterned after the murine, rat or other starting hypervariable region sequences and encompass the same regions defined by the direct hypervariable region grafts. Optionally, two positions, amino acids at the beginning of H2 and H3 in the VH domain, may be limited in their diversity: the codon RGC may be used for position 49 encoding A, G, S or T and at position 94, the codon AKG may be used encoding M or R.

Generation of phage libraries—Randomized oligonucleotide pools designed for each hypervariable region were phoshorylated separately in six 20 µl reactions containing 660 ng of oligonucleotide, 50 mM Tris pH 7.5, 10 mM MgCl$_2$, 1 mM ATP, 20 mM DTT, and 5 U polynucleotide kinase for 1 h at 37° C. The six phosphorylated oligonucleotide pools were then combined with 20 µg of Kunkel template in 50 mM Tris pH 7.5, 10 mM MgCl$_2$ in a final volume of 500 µl resulting in an oligonucleotide to template ratio of 3. The mixture was annealed at 90° C. for 4 min, 50° C. for 5 min and then cooled on ice. Excess, unannealed oligonucleotide was removed with a QIAQUICK™ PCR purification kit (Qiagen kit 28106, Qiagen, Valencia, Calif.) using a modified protocol to prevent excessive denaturation of the annealed DNA. To the 500 µl of annealed mixture, 150 µl of Qiagen buffer PB was added, and the mixture was split between 2 silica columns. Following a wash of each column with 750 µl of Qiagen buffer PE and an extra spin to dry the columns, each column was eluted with 110 µl of 10 mM Tris, 1 mM EDTA, pH 8. The annealed and cleaned-up template (220 µl) was then filled in by adding 1 µl 100 mM ATP, 10 µl 25 mM dNTPs (25 mM each of dATP, dCTP, dGTP and dTTP), 15 µl 100 mM DTT, 25 µl 10×TM buffer (0.5 M Tris pH 7.5, 0.1 M MgCl$_2$), 2400 U T4 ligase, and 30 U T7 polymerase for 3 h at room temperature.

The filled-in product was analyzed on Tris-Acetate-EDTA/agarose gels (Sidhu et al., *Methods in Enzymology* 328:333-363 (2000)). Three bands are usually visible: the bottom band is correctly filled and ligated product, the middle band is filled but unligated and the top band is strand displaced. The top band is produced by an intrinsic side activity of T7 polymerase and is difficult to avoid (Lechner et al., *J. Biol. Chem.* 258:11174-11184 (1983)); however, this band transforms 30-fold less efficiently than the bottom band and usually contributes little to the library. The middle band is due to the absence of a 5' phosphate for the final ligation reaction; this band transforms efficiently and gives mainly wild type sequence.

The filled in product was then cleaned-up and electroporated into SS320 cells and propagated in the presence of M13/KO7 helper phage as described by Sidhu et al., *Methods in Enzymology* 328:333-363 (2000). Library sizes ranged from 1-2×10$^9$ independent clones. Random clones from the initial libraries were sequenced to assess library quality.

Phage Selection—Full length human integrin alpha4beta7 was expressed in 293 cells (Graham et al., *J. Gen Virol.* 36:59 (1977)), purified by Fib504 affinity chromatography and used as the target for phage selection. For immobilization on MaxiSorp™ microtiter plates (Nalge Nunc, Rochester, N.Y.), 100 µl of human integrin alpha4beta7 was coated at 5 µg/ml in 150 mM NaCl, 50 mM Tris pH 7.5, 2 mM CaCl$_2$, 2 mM MgCl$_2$ and 2 mM MnCl$_2$ (TBSM), overnight at 4 degrees C. Wells were blocked for 1 h using TBSM containing 1% BSA. For the first round of selection, 8 wells coated with target were used; a single target coated well was used for successive rounds of selection. Phage were harvested from the culture supernatant and suspended in TBSM containing 1% BSA and 0.05% TWEEN™ 20 (TBSMBT). After binding to the wells for 2 h, unbound phage were removed by extensive washing with TBS containing 0.05% TWEEN 20 (TBST). Bound phage were eluted by incubating the wells with 100 mM HCl for 30 min. Phage were amplified using Top10 cells and M13/KO7 helper phage and grown overnight at 37° C. in 2YT, 50 µg/ml carbanacillin. The titers of phage eluted from a target coated well were compared to titers of phage recovered from a non-target coated well to assess enrichment. After four rounds of selection were performed, random clones were selected for sequence analysis.

Fab Production and Affinity Determination—To express Fab protein for affinity measurements, a stop codon was introduced between the heavy chain and g3 in the phage display vector. Clones were transformed into *E. coli* 34B8 cells and grown in AP5 media at 30 C (Presta, L. et al., Cancer Res. 57:4593-4599 (1997)). Cells were harvested by centrifugation, suspended in 10 mM Tris, 1 mM EDTA pH 8 and broken open using a microfluidizer. Fab was purified with Protein G affinity hromatography.

Affinity determinations were performed by surface plasmon resonance using a BIAcore™-3000 (Biacore, Piscataway, N.J.). Humanized Fib504 Fab variants were immobilized in 10 mM acetate pH 4.5 (ranging from 250 to 1500 response units (RU)) on a CM5 sensor chip and 2-fold dilutions of human integrin alpha4beta7 (1.5 to 770 nM) in TBSM containing 2% n-octylglucoside were injected. Each sample was analyzed with 5-minute association and 5 to 60-minute dissociation times. After each injection, the chip was regenerated using three 1-minute injections of 8 M urea. Binding response was corrected by subtracting the RU from a blank flow cell. A 1:1 Languir model of simultaneous fitting of $k_{on}$ and $k_{off}$ was used for kinetics analysis.

Results and Discussion

Humanization of rat Fib504—The human acceptor framework used for humanization is based on the framework used for HERCEPTIN® and consists of the consensus human kappa I (huKI) VL domain and a variant of the human subgroup III (humIII) consensus VH domain. This variant VH domain has 3 changes from the human consensus: R71A, N73T and L78A. The VL and VH domains of rat Fib504 were each aligned with the human kappa I and subgroup III domains; each hypervariable region (HVR) was identified and grafted into the human acceptor framework to generate a HVR graft (504 graft) that could be displayed as an Fab on phage (FIGS. 1A and 1B).

Based on the analysis of available antibody and antigen complex crystal structures MacCallum et al. (MacCallum et al. *J. Mol. Biol.* 262: 732-745 (1996)) proposed HVR definitions based on variable domain residues that frequently contact antigens. Thus positions 49G and 94M of the heavy chain were included in the HVR graft of Fib504 (FIG. 1B). In addition, a second HVR graft, Fib504 Kgraft, was also generated which included position 49K of the light chain, because this position is also within the contact definition of HVR-L2 and can serve as an antigen contact (FIG. 1A). When either the Fib504 or Fib504K grafts were displayed on phage and tested for binding to immobilized alpha4beta7, no binding was observed.

Libraries were generated using both the Fib504 and Fib504-K HVR grafts in which each of the HVR regions were soft randomized simultaneously. Each HVR graft library was panned against immobilized alpha4beta7 for 4 rounds of selection. No enrichment was observed and clones picked for DNA sequence analysis displayed only random sequence changes targeted to the 6 HVR regions.

Two additional VH framework sequences, "RL" and "RF" were investigated as acceptor frameworks and contained changes at positions 71 and 78. Position 71 was changed to an Arginine as in the human subgroup III consensus, and position 78 was changed to a Leucine as in the human subgroup III consensus (acceptor framework "RL") or a Phenylalanine as in the human subgroup II consensus and the rat Fib504 VH framework (acceptor framework "RF") (FIG. 10A). When either the Fib504 or Fib504K graft in the "RL" (Fib504-RL and Fib504K-RL) or "RF" (Fib504-RF and Fib504K-RF) acceptor framework was displayed on phage and tested for binding to immobilized alpha4beta7. Specific phage binding was only observed for the Fib504K graft using the "RF" framework (FIG. 10B). The modest binding of phage displaying the Fib504-RF graft relative to the other grafts lacking Y49K (light chain) and L78F (heavy chain) indicates the importance of these positions in selecting a useful acceptor framework.

Libraries were generated as before using a soft randomization strategy simultaneously at each of the 6 HVRs for the Fib504K-RL and Fib504K-RF grafts and sorted on immobilized alpha4beta7 for 4 rounds of selection as described above. Enrichment was only observed for the library based on the Fib504K-RF graft. Clones from round 4 of the Fib504K-RF library were selected for sequence analysis and revealed amino acid changes targeted to HVR-L1. Most clones contained the change Y32L; in addition position 31 was frequently changed to D, S, P or N (FIG. 1C). In addition to the starting graft, Fib504K-RF, 3 clones were expressed and purified as Fab protein and further analyzed by Biacore as described above. Clones hu504-5, hu504-16 and hu504-32 (variants of SEQ ID NO:1 containing substitutions T31S plus Y32L (variant hu504.5), Y32L (variant hu504.16), or T31D plus Y32L (variant hu504.32); see FIG. 1C), showed excellent binding to alpha4beta7 relative to the Fib504K-RF graft and met or exceeded the affinity of the chimeric Fib504 Fab for binding to alpha4beta7. The results of the Biacore analysis are shown in Table 3, below, and indicate that selected variation in the HVRs and/or framework regions, disclosed herein, generated antagonist antibodies to alpha4beta7 having improved affinity relative to the starting antibody. The results in Table 3 indicate that humanized variant 504.32 showed the greatest increase in affinity relative to the starting rat antibody by binding 3-fold more tightly to alpha4beta7.

TABLE 3

| Fab (BIAcore ™ analysis) | Affinity to Alpha4beta7 (nM) |
| --- | --- |
| Fib504 | 11 |
| Variant 504.5 | 9 |
| Variant 504.16 | 23 |
| Variant 504.32 | 3 |

The results in Table 3 also indicate that the redesign of HVR-L1 was important to the restoration of high affinity antigen binding. In particular, the mutation Y32L was most frequent among the various clones. Other changes at position 31 and numerous other substitutions throughout HVR-H1 appear to be well tolerated and may provide additional improvement. From these results it is clear that there are multiple sequence changes that can improve the affinity of Fib504 grafted onto a human framework to generate affinities that meet or exceed that of the initial rat antibody.

Thus, starting from the graft of the 6 rat Fib504 HVRs into the human acceptor scaffold, the expansion of HVR-L2 to include position 49 (Lysine), expansion of HVR-H2 to include position 49 (Glycine), and the expansion of HVR-94 to include position 94 (Methionine) as well as amino acid changes at position 32 of VHR-L1 (where L or I replace Y) and, optionally, at position 31 of the VHR-L1 (where T is replaced by D or S, for example). Useful framework amino acid changes were made at positions 71 (A71R) and 78 (L78F) in the VH domain. Such amino acid changes lead to a fully human antibody, variant hu504.32, for example, with 3-fold improved binding affinity for alpha4beta7 integrin. Furthermore, selected humanized antibodies described herein have been determined to have at least comparable biological activity as the parent rat Fib504 antibody (see Example 3 herein).

Example 2

Additional Humanized Fib504 HVR Variants

The HVR amino acid sequences of humanized variant Fib504.32 were further modified to generated additional variants capable of antagonizing the activity of beta7 integrin subunit and/or integrins containing the beta7 subunit.

Generating a broad amino acid scan library—A library to scan selected HVR positions for other amino acid residues capable of generating beta7-binding variants of variant hu504.32 was generated using 3 oligonucleotides: 504-L1, designed to soft randomize a portion of HVR-L1 with a bias towards the hu504.32 HVR-L1 sequence (i.e. the sequence ASESVDDLLH (SEQ ID NO:47, for relative positions A2-A11) was soft randomized as described above); and HVR-L3 504-N96 and HVR-H3 504-M94 which introduce NNS at positions HVR-L3 position 96 in the light chain and HVR-H3 position 94 in the heavy chain, thus allowing all 20 amino acids at these positions. With these three oligonucleotides, the broad amino acid scan library was generated as described above using a template containing three stop codons in the light chain (positions 31 and 32 in HVR-L1 and position 96 in HVR-L3) and 1 stop codon in the heavy chain (position 94 in HVR-H3).

Broad amino acid scan of hu504-32—To more fully explore the preferred sequences allowed in HVR-L1 and to enhance the stability of 504-32, we designed a phage library that a) soft randomized HVR-L1 of 504-32 in the region where changes were observed (i.e. ASESVDDLLH (SEQ ID NO:47, for relative positions A2-A11) during humanization (FIG. 1C), and b) allowed all possible amino acids at N96 in HVR-L3 and M94 in HVR-H3. Following 4 rounds of selection against immobilized full-length human integrin alpha4beta7 as described above, 96 random clones were selected for sequence analysis. The frequency at which amino acids were found at each position in the broad amino acid scan library suggest that the HVR-L1 sequence present in hu504-32 and the methionine at position 94 in the heavy chain are optimum for high affinity binding (FIG. 12). The most preferred amino acids obtained by the selections starting from variant 504.32 (FIG. 12) are shown in yellow. In contrast, although asparagine is present at position 96 in the light chain of hu504-32, the high frequency of leucine observed at this position in the broad amino acid scan suggests the mutation N96L could further improve the affinity of humanized Fib504 variants for alpha4beta7 and also eliminate any potential deamidation problems at this position. The information in FIG. 12 also suggests that a number of replacement amino acids are likely to be tolerated at most positions without a substantial loss in affinity. For example, to eliminate oxidation of M94 in HVR-H3, glutamine or arginine could likely be substituted.

Generating the limited amino acid scan libraries—Six libraries for a limited amino acid scan utilized six different Kunkel templates, each containing one stop codon located within one of the six HVRs. Each library was generated using a single oligonucleotide encoding a single HVR and utilizing the codons listed in FIG. 11A ("codon" column) to alter amino acid residues for subsequent testing for binding to beta7 or alpha4beta7. The same procedures are used to alter amino acid residues of anti-beta7 antibodies and test them for binding to alphaEbeta7 integrins.

Limited amino acid scan of hu504-32—The limited amino acid scan of hu504-16 was designed to make hu504-16 even more like the human light and heavy chain consensus sequence and in the process identify the minimal sequence elements of rat Fib504 that are required for binding. Six libraries were generated and targeted at each HVR at positions that differed between the hu504-16 and human consensus kappa I light or subgroup III heavy chains (FIGS. 1A and 1B); either the rat or human amino acid was allowed at these positions in the library (FIG. 11A). In order to accommodate coding for both amino acids during the oligonucleotide synthesis and mutagenesis, additional amino acids were also introduced in some cases (see encoded amino acids, FIG. 11A). The limited amino acid scan libraries were selected against immobilized full-length human integrin alpha4beta7 as described above and approximately 32 random clones were sequenced from each library after round 3. The frequency of each amino acid found at each position is shown in FIG. 11B and 11C.

Like the broad amino acid scan, the limited amino acid scan also provides information about what changes are tolerated at many positions in humanized Fib504. Unlike the broad amino acid scan, however, the diversity allowed at each position randomized in the limited amino acid scan was restricted to a couple of amino acids. Thus the lack of any observed substitution at a given position does not indicate that a particular residue can not be changed nor does the high frequency of any particular amino acid at a given position necessarily indicate that it is the best solution for high affinity.

At some positions (positions 27, 29, 30, 53, 54 of the light chain and 50, 54, 58, 60, 61, and 65 of the heavy chain) the human consensus amino acid is selected quite frequently suggesting a back mutation to the human consensus would not dramatically alter binding to human alpha4beta7. In fact, at position 54 of the light chain (in HVR-L2), the human consensus amino acid is selected more frequently than the amino acid from rat Fib504 indicating that this change made to 504-32 provides a useful beta7 binding antibody.

Further, as a result of the library design, amino acids that are not derived from either the human consensus or rat Fib504 are selected more frequently at some positions and provide potential substitutions to improve the affinity of humanized Fib504 variants. These include, without limitation, D30A and I55V in the light chain and Y50F in the heavy chain The results from these 2 libraries indicate that many HVR positions tolerate other amino acid substitutions and still retain comparable biological activity.

Summaries of observed amino acid changes are shown in FIGS. 13 and 15. FIG. 15 summarizes the various amino acids useful at each of the positions in the CDRs of the antibody variants of the invention at positions numbered according to Kabat numbering or a relative numbering system. Each of the additional antibodies encompassed by the variants depicted in FIGS. 13 and 15 is an embodiment of the invention.

Example 3

Cell Adhesion Assays

The ability of some of the humanized Fib504 variants of the invention to bind ligands expressed on a cell surface was tested by cell adhesion assays. Binding to alpha4beta7 and another beta7 integrin, alphaEbeta7 were tested by the ability of the humanized variants to disrupt binding of the integrin to its natural receptor. Binding of the humanized Fib504 variants to beta7 subunit alone expressed on a cell surface was similarly tested. The procedures and the results are described below.

IgG production—Humanized Fib 504 IgG variants were expressed transiently in 293 cells (Graham et al. (1977) supra) using a separate vector for the light and heavy chains. The vectors were constructed by subcloning the light or heavy variable domains into suitable expression vectors for each of the light and heavy chains. Supernatant from 1.1 L CHO cell culture of a humanized Fib504 variant was filtered through a 0.45 um filter and applied to a new 1 mL HiTrap Protein A HP column (Amersham/Pharmacia) equilibrated in Buffer A (10 mM tris pH 7.5, 150 mM NaCl). Samples were applied at 0.8 mL/min, overnight, 4 degrees C. Each column was then washed and equilibrated with 30 mL Buffer A. Elution of antibody was accomplished by chromatography at room temperature on an FPLC (Amersham/Pharmacia) using a linear gradient of 14 min at 1 mL/min from 0 to 100% Buffer B (100 mM Glycine, pH 3.0). Resulting 1 mL fractions were immediately neutralized by the addition of 75 uL 1 M tris, pH 8. Eluted protein was detected by absorption at 280 nm, and peak fractions were pooled and desalted into PBS on PD10 G-25 sephadex disposable sizing columns (Amershai/Pharmacia). Protein was detected by OD280 and peak fractions were pooled. The antibody in PBS was 0.22 um filtered and stored at 4 degrees C. Amino acid analysis was used to quantify the concentrations of these purified antibodies, and values were assigned from the average of two separate determinations.

BCECF Labeling:

In each of the assays presented in this Example 3, cells were labeled according to the following procedure. All cells used in the adhesion assays were labeled with 2',7'-bis-(2-carboxylethyl)-5-(and-6)-carboxyfluorescein, acetoxymethyl ester (BCECF) at 10 uM in RPMI1640 media containing 10% FBS for RPMI8866 cells and 38C13 cells transfected with beta7 subunit (38C13 beta7 cells) and in F-12:DMEM mix (50:50) containing 10% FBS for alphaEbeta7-transfected 293 cells (alphaEbeta7 293 cells). Cells were labeled for 30 minutes and washed two times with assay media. Cell density was adjusted to $3\times10^6$ cells per ml for RPMI8866 and 38C13beta7 cells and $2.2\times10^6$ cells per ml for alphaEbeta7 293 cells.

Humanized Fib504 Variants Disrupt Alpha4Beta7 Binding to MAdCAM

RPMI8866/MAdCAM-1-Ig Cell Adhesion: RPMI8866 cells express alpha4beta7 on their surface (Roswell Park Memorial Institute, Buffalo, N.Y.). Humanized Fib504 variants (hu504 variants) were contacted with a mixture of RMPI8866 cells and MAdCAM fused to IgG coated on a solid support. Humanized Fib504 variant concentrations resulting in 50% inhibition ($IC_{50}$) of the binding of RPMI8866 cells to MAdCAM-1 were measured by coating Nunc Maxisorp™ 96-well plates with 2 μg/ml in PBS, 100

µl/well MAdCAM-1-Ig (Genentech, Inc., where Ig refers to fusion of MAdCAM-1 to an Fc region) overnight at 4° C. After blocking the plates with 200 ul/well of 5 mg/ml BSA for one hour at room temperature, 50 µl of humanized Fib504 variants in assay media (RPMI 1640 media, Hyclone®, Logan Utah, USA, supplemented with 5 mg/mL BSA) were added to each well and 150,000 BCECF-labeled cells (BCECF, Molecular Probes, Eugene, Oreg.) in 50 µl of assay media were added to each well and incubated for 15 minutes at 37° C. The wells were washed two times with 150 µl of assay media to remove unbound cells. The bound cells were solubilized with 100 µl of 0.1% SDS in 50 mM Tris/HCl pH7.5. The amount of fluorescence released from lysed cells was measured by SPECTRAmax GEMINI™ (Molecular Devices, Sunnyvale, Calif.) at 485 nm excitation 530 nm emission wavelengths. The fluorescence values were analyzed as a function of the concentrations of the humanized Fib504 variants added in each assay, using a four-parameter nonlinear least squares fit, to obtain the $IC_{50}$ values of each humanized Fib504 variant in the assay. $IC_{50}$ and $IC_{90}$ values were estimated from the four-parameter fit. FIG. 14 is an exemplary plot of the results. The $IC_{90}$ and $IC_{50}$ values for each of the variants tested are shown below in Table 4.

TABLE 4

Antibody binding to human MAdCAM-1

| Antibody Tested: Fib504 and hu504 variants | $IC_{50}$ (nM) Exp 1/Exp 2* | $IC_{90}$ (nM) Exp 1/Exp 2* |
|---|---|---|
| Rat Fib504 | 0.098/0.197 | 0.483/0.703 |
| Variant hu504.5 | 0.067/0.248 | 0.361/0.880 |
| Variant hu504.16 | 0.0768/0.206 | 0.244/0.551 |
| Variant hu504.32 | 0.036/0.119 | 0.150/0.396 |
| 6B11 (non-blocking control) | >100 | >100 |

*Exp 1/Exp 2 refers to the results of repeated assays.

Humanized Fib504 Variant Disruption of Alpha4Beta7 Binding to VCAM

RPMI8866/7dVCAM-1 Cell Adhesion: The RPMI8866/7dVCAM-1 assay is similar format to the RPMI8866/MAdCAM-1-Ig except that 7dVCAM-1 (ADP5, R&D Systems, Minneapolis, Minn.) was used at 2 ug/ml to coat plates. The results were analyzed as described above for the MAdCAM binding experiments. The $IC_{50}$ values for each of the variants tested are shown below in Table 5.

TABLE 5

Antibody binding to human VCAM

| Antibody Tested: Fib504 and hu504 variants | $IC_{50}$ (nM) Exp 1/Exp 2* | $IC_{90}$ (nM) Exp 1/Exp 2* |
|---|---|---|
| Rat Fib504 | 0.107/0.193 | 0.396/0.580 |
| Variant hu504.5 | 0.088/0.270 | 0.396/0.726 |
| Variant hu504.16 | 0.098/0.223 | 0.261/0.774 |
| Variant hu504.32 | 0.059/0.110 | 0.183/0.337 |
| 6B11 (non-blocking control) | >100 | >100 |

*Exp 1/Exp 2 refers to the results of repeated assays.

Humanized Fib504 Variant Disruption of alphaEbeta7 Binding to Human E-Cadherin

AlphaEbeta7 293/huE-Cadherin Cell Adhesion: 293 cells (Graham et al. (1977) supra) were transfected with alphaE and beta7 (Genentech, Inc.). The assay format is similar to the RPMI8866/MAdCAM-1-Ig assay except that the huE-Cadherin (648-EC, R&D Systems, Minneapolis, Minn.) was used at 2 µg/ml to coat the plates. Plates were then blocked with 5 mg/ml BSA as mentioned above and 50 µl of FIB504 variants in assay media (F-12:DMEM (50:50) supplemented with 5 mg/ml BSA) were add to each well and 110,000 BCECF labeled cells in 50 ul of assay media were added to each well and incubated for 15 minutes at 37° C. The wells were washed two times with 150 µl of assay media and the amount of fluorescence released by lysed cells was measured and analyzed as described above. Assay results from three experiments are shown in Table 6.

TABLE 6

Antibody binding to human E-Cadherin

| Antibody Tested: Fib504 and hu504 variants | $IC_{50}$ (nM) | $IC_{90}$ (nM) |
|---|---|---|
| Rat Fib504 | 2.047/7.89/4.19 | 8.80/24.5/9.95 |
| Variant hu504.5 | 2.132/10.18/4.77 | 7.99/28.7/10.19 |
| Variant hu504.16 | 1.957/10.05/4.58 | 7.03/33.7/13.51 |
| Variant hu504.32 | 1.814/6.99/3.47 | 8.8/24.5/11.73 |
| HP2/1 (anti-alpha4, control) | >100/>100/>100 | >100/>100/>100 |

Humanized Fib504 Variant Disruption of Beta7 Binding to MAdCAM

38C13beta7/muMAdCAM-1-Ig Cell Adhesion Assay: The 38C13beta7/muMAdCAM-1-Ig assay was similar format to the RPMI8866/MAdCAM-1-Ig except that muMAdCAM-1-Ig (Genentech, Inc.) was used at 2 µg/ml to coat plates. 38C13 alpha4+ murine lymphoma cells (Crowe, D. T. et al., J. Biol. Chem. 269:14411-14418 (1994)) were transfected with DNA encoding integrin beta7 such that alpha4beta7 was expressed on the cell surface. The ability of the antibodies variants to disrupt interaction between the cell membrane associated alpha4beta7 and MAdCAM was performed as above. Assay results are shown in Table 7. Assay results are shown in Table 7. ($IC_{50}$ and $IC_{90}$ values for 2 experiments are shown).

TABLE 7

Activity of hu504 variant antibodies in 38C13-beta7 expressing cells Binding to murine MAdCAM

| Antibody Tested: Fib504 and hu504 variants | $IC_{50}$ (nM) | $IC_{90}$ (nM) |
|---|---|---|
| Rat Fib504 | 0.682/0.306 | 2.869/1.51 |
| Variant hu504.5 | 0.8587/0.466 | 2.322/2.61 |
| Variant hu504.16 | 0.998/0.610 | 3.717/4.08 |
| Variant hu504.32 | 0.718/0.458 | 4.08/1.51 |

Humanized Fib504 Variant Disruption of Beta7 Binding to Murine VCAM

38C13beta7/muVCAM-1-Ig Cell Adhesion Assay: The 38C13beta7/muVCAM-1-Ig assay was performed according to the murine MAdCAM-1-Ig/RPMI8866 cell binding assay above, except that muVCAM-1-Ig (Genentech, Inc.) was used at 2 µg/ml to coat plates. Results of the assay are shown in Table 8. ($IC_{50}$ and $IC_{90}$ values for 2 experiments are shown).

TABLE 8

Activity of hu504 variant antibodies in 38C13-beta7 expressing cells Binding to murine VCAM-1-Ig

| Antibody Tested: Fib504 and hu504 variants | $IC_{50}$ (nM) | $IC_{90}$ (nM) |
|---|---|---|
| Rat Fib504 | 0.845/0.447 | 2.903/2.30 |
| Variant hu504.5 | 0.763/0.407 | 3.074/2.30 |

TABLE 8-continued

Activity of hu504 variant antibodies in 38C13-beta7 expressing cells Binding to murine VCAM-1-Ig

| Antibody Tested: Fib504 and hu504 variants | IC$_{50}$ (nM) | IC$_{90}$ (nM) |
|---|---|---|
| Variant hu504.16 | 0.835/0.584 | 2.857/1.84 |
| Variant hu504.32 | 0.562/0.330 | 2.004/1.84 |

The results of the humanized Fib504 variant binding studies demonstrate that the humanized antibody of the invention binds its target beta7 integrin subunit as well as the alpha4beta7 and alphaEbeta7 integrin with about the affinity of the starting rat antibody and, in some embodiments, with greater affinity. Thus, a humanized anti-beta7 antibody according to the invention has uses in anti-beta7 integrin therapies, particularly human therapies.

Relative Activity of Hu504.32 Variants of the Invention

Different amino acid variants of the hu504.32 antibody were tested in human and mouse cell adhesion assay for their ability to inhibit beta7-containing receptor binding to its ligand according to the cell adhesion assay methods disclosed herein. The RPMI8866/MAdCAM-1-Fc assay was performed as described herein above. The alphaEbeta7-293/hu E-cadherein assay was modified by the use of human E-cadherin-Fc as the ligand (human E-cadherin-Fc, 648-EC, R&D Systems, Minneapolis, Minn.). The relative ability of hu504.32 variants to inhibit interaction of human fibronectin (huFN40) with human alpha4beta7 receptor on PRMI8866 cells was also examined. The RPMI8866/hu Fibronectin (huFN40) assay used for these studies was similar in format to the RPMI8866/MAdCAM-1-Ig assay disclosed herein except that human fibronectin alpha-chymotryptic fragment 40 kDa (F1903, Chemicon International, Temecula, Calif.) was used at 2 µg/ml to coat plates.

The ability of the hu504.32 variants to inhibit interaction of murine beta7-containing receptors with murine MAdCAM-1 or murine VCAM-1 was examined. Murine MAdCAM-1-Fc and murine VCAM-1-Fc were inhibited from interacting with murine lymphoma alpha4+ cells expressing murine beta7 (38C13beta7 cells) by the hu504.32 variants. The murine MAdCAM-1-Fc and VCAM-1-Fc cell adhesion assays were performed similarly to those described herein above for human MAdCAM and VCAM. Where ligands were fused to Fc regions, the Fc receptors on the cells were blocked with 0.5 µg anti-CD16/32 antibody (anti-Fcgamma III/II receptor antibody, catalog No. 553142, BD Biosciences, San Jose, Calif.) per 1 million cells for 5 minutes at room temperature. 150,000 labeled cells in 50 µl of assay medium were added to each well and incubated for 13 minutes at 37° C. The wells were washed and the amount of fluorescence released from lysed cells was measured as disclosed herein above. The control antibody for the human cell adhesion assays was the mouse monoclonal antibody to human serum albumin, 6B11 (Catalog No. ab10244, Novus Biologicals, Littleton, Colo., USA). The control antibody for the murine cell adhesion assays was the rat anti-mouse integrin beta7 antibody, M293 (BD Biosciences, San Jose, Calif.), which does not compete with ligand or with Fib504 for binding to integrin beta7.

The results of triplicate assays for the human and murine cell adhesion assays are provided in Tables 9 and 10, respectively.

TABLE 9

Activity of hu504.32 Variant Antibodies in Human Cell Adhesion Assays

| | IC50 Ave ± SD | | | |
|---|---|---|---|---|
| Antibody Variant | RPMI8866/ huMAdCAM-1-Fc | RPMI8866/ hu7dVCAM-1 | αEβ7-293/ huE-Cadherin-Fc | RPMI8866/ huFN40 |
| hu504.32 | 0.088 ± 0.035 | 0.101 ± 0.021 | 3.970 ± 1.664 | 0.100 ± 0.046 |
| hu504.32M94Q | 0.090 ± 0.045 | 0.111 ± 0.035 | 4.130 ± 1.212 | 0.124 ± 0.056 |
| hu504.32M94R | 0.075 ± 0.034 | 0.089 ± 0.009 | 3.963 ± 1.776 | 0.119 ± 0.056 |
| Control (6B11) | >100 | >100 | >100 | >100 |

TABLE 10

Activity of hu504.32 Variant Antibodies in Murine Cell Adhesion Assays

| | IC50 Ave ± SD | |
|---|---|---|
| Antibody Variant | 38C13beta7/ muMAdCAM-1-Fc | 38C13beta7/ mu7dVCAM-1-Fc |
| hu504.32 | 0.270 ± 0.041 | 0.228 ± 0.065 |
| hu504.32M94Q | 0.370 ± 0.102 | 0.264 ± 0.083 |
| hu504.32M94R | 0.391 ± 0.112 | 0.228 ± 0.081 |
| Control (M293) | >100 | >100 |

The hu504.32 antibody has a methionine at position 94 of the heavy chain CDR3. The variants M94Q (or hu504.32Q) and M94R (or hu504.32R) have glutamine or arginine, respectively, at position 94 of the hu504.32 antibody variant. The hu504.32M, Q, and R antibodies substantially reduced integrin beta7 receptor-ligand interaction in in each of the assays and are, thus, potent inhibitors of beta7-mediated cell adhesion.

Antibody hu504.32R Activity In Vivo

The hu504.32R antibody variant was tested in vivo for its ability to reduce integrin beta7 receptor-ligand interaction and reduce lymphocyte recruitment to inflamed colon in an in vivo murine inflammatory bowel disease model. BALB/c mice and CB17 SCID mice were obtained from Charles River Laboratories International, Inc. (Wilmington, Mass., USA). CD4$^+$ CD45Rb high T cell reconsituted SCID colitic mice were prepared by isolating CD4$^+$ CD45Rb high T cells from donor BALB/c mice and transferring 3×10$^5$ cells in 100 µl PBS intravenously. Control SCID mice did not receive CD4$^+$ CD45Rb high T cells. Reconstituted CD4+ mice meeting the treatment group enrollment criteria of 10% weight loss from baseline or 15% from peak weight at week 4 were considered to have induced inflammatory bowel disease and were selected for treatment.

On the day of treatment with test antibodies, donor BALB/c mice mesenteric lymph node (MLN) cells were harvested and radiolabelled with Cr[51]. Treatment involved prior administration of anti-GP120 antibody, hu504.32 anti-beta7 antibody, hu504.32R anti-beta7 antibody, or no antibody (control) intravenously, 200 μg/100 μl PBS. Thirty minutes after antibody administration, Cr[51]-labelled MLN cells were injected, 4×10[6] cells/100 μl. One hour post-injection of labelled cells, mice were euthanized and spleen, colon, and peyers patch were collected, weighed, and total Cr[51] radioactivity per organ was determined. FIG. 16 is a bar graph of the results of these tests showing the relative ability of the antibodies to block homing of radiolabelled T cells to the colon of mice experiencing inflammatory bowel disease. Homing of T cells to inflamed colon was inhibited by hu504.32 and hu504.32R anti-beta7 antibodies relative to negative control, anti-GP120 antibody. Distribution to spleen was similar for all of the antibodies. Thus, the hu504.32 and hu504.32R anti-beta7 antibodies effectively inhibit homing of T cells to inflamed colon in vivo.

Antibody glycation does not affect the ability of hu504.32R variant to block MAdCAM-1 binding to alpha4beta7 receptor.

Glycation, the non-enzymatic glycosylation of proteins, can affect antibody-ligand interactions (see, for example, Kennedy, D. M. et al., Clin Exp Immunol. 98(2):245-51 (1994). Glycation of lysine at position 49 of the 504.32R Glycation of the lysine at light chain position 49 of the hu504.32R variant (HVR-L2 relative position B1) was observed but had no significant affect on the ability of the antibody variant to block the binding of MAdCAM-1 to alpha4beta7 receptor-expressing RPMI8866 cells. Determination of glycation and glycation levels was performed using standard elctrospray ionization-mass spectroscopy (ESI-MS) and by boronate affinity chromatography. Boronate affinity HPLC methods useful to test for glycation are found at, for example, Quan C. P. et al., Analytical Chemistry 71(20): 4445-4454 (1999) and Li Y. C. et al., J. Chromatography A, 909:137-145 (2001). The cell adhesion assay was performed according to the RPMI8866/MAdCAM-1-Fc cell adhesion assay disclosed herein.

In alternative embodiments of the invention, glycation at position 49 is reduced or eliminated where position 49 comprises an amino acid other than lysine. The polypeptide or antibody of the invention encompasses as an amino acid at position 49 (HVR-L2 relative position B1) any of amino acids A, C, D, E, F, G, H, I, L, M, N, P, Q, R, S, T, V, W, or Y, where each letter refers to a amino acid according to the standard single-letter amino acid designation. Alternatively, the amino acid at position 49 of the light chain of a 504.32R variant (or other 504 variant) is selected from the group consisting of R, N, V, A, F, Q, H, P, I, or L. An amino acid useful at position 49 is selected, for example, by displaying (preparing a phage library of) the hu504.32R Fab on phage (variant) and substituting separately, at the codon for position 49, a codon for each of the 20 naturally occurring amino acids. Phage expressing the hu504.32R variants altered at position 49 are tested for binding to integrin beta7 and/or to a receptor comprising integrin beta7, such as alpha4beta7 or alphaEbeta7 receptors. Those variants which bind to beta7 integrin or the alpha4beta7 or alphaEbeta7 receptors are further screened for the ability to inhibit integrin beta7 receptor-ligand binding and in vivo efficacy as described herein. Alternative, naturally or non-naturally occurring amino acids may be substituted at position 49 by standard mutagenesis techniques and tested in the cell adhesion and in vivo assays described herein. Alternatively, the amino acid at position 49 of the light chain is an amino acid other than lysine (K), and amino acids at any other HVR or framework position or positions in the light chain and/or heavy chain is altered to select for a variant anti-beta7 binding polypeptide or antibody that exhibits binding affinity, in vitro and in vivo biological activity, pharmacokinetics, drug clearance and immunogenicity useful for reduction of inflammation by reducing the biological activity of integrin beta7. Mutagenesis and selection of such a polypeptide or antibody variant is performed as disclosed herein and according to other standard techniques. Such a variant anti-beta7 binding polypeptide or antibody exhibits integrin beta7 binding affinity within 10,000-fold, 1000-fold, alternatively within 100-fold, alternatively within 10-fold, alternatively within 5-fold, alternatively within 2-fold of the binding affinity exhibited by the any of the humanized Fib504 variants disclosed herein.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method of inhibiting the interaction of a human beta7 integrin subunit with a second integrin subunit and/or a ligand by contacting a humanized antibody with the beta7 integrin, wherein said antibody is a humanized anti-integrin beta 7 antibody comprising three heavy chain hypervariable region (HVR-H1-H3) sequences and three light chain hypervariable region (HVR-L1-L3) sequences, wherein at least one HVR is a variant of SEQ ID NO. 1, 2, 3, 5, or 6, wherein:

(a)(i) HVR-L1 comprises sequence A1-A11, wherein A1-A11 is RASESVDTYLH (SEQ ID NO:1), or a variant thereof, wherein (1) in SEQ ID NO:1 at position A8 T is substituted by S, D or T and at position A9 Y is substituted by L, or wherein said variant comprises (2) 1-10 (1, 2, 3, 4, 5, 6, 7, 8, 9, or 10) substitutions in SEQ ID NO:1 in any combination of the following positions: A2 (A, G, S, T, or V); A3 (S, G, I, K, N, P, Q, R, or T), A4 (E, A, D, G, H, I, K, L, N, Q, R, or V), A5 (S, A, D, G, H, I, K, N, P, R, T, V, or Y), A6 (V, A, G, I, K, L, M, Q, or R), A7 (D, A, E, G, H, I, K, L, N, P, S, T, or V), A8 (S, D, E, G, P, T or N), A9 (L, Y, I, or M), A10 (L, A, I, M, or V), and A11 (H, F, S, or Y), or wherein (3) HVR-L1 comprises a sequence selected from the group consisting of SEQ ID NO:7, SEQ ID NO:8, and SEQ ID NO:9; and wherein the additional hypervariable sequences are: (ii) HVR-L2 comprising sequence B1-B8, wherein B1-B8 is KYASQSIS (SEQ ID NO: 2), or a variant thereof, wherein said variant comprises 1-4 (1, 2, 3, or 4) substitutions in SEQ ID NO: 2 in any combination of the following positions: B1 (K, R, N, V, A, F, Q, H, P, I, L, Y, T, H S, E, C, D, G, or M), B5 (Q or S), B6 (S, R or L), and B7 (I, T, E, K, or V); (iii) HVR-L3 comprising sequence C1-C9, wherein C1-C9 is QQGNSLPNT (SEQ ID NO: 3), or a variant thereof, wherein said variant comprises at least one of the following substitutions in SEQ ID NO: 3 at position C8 (W, Y, R, S, A, F, H, I, L, M, N, T, or V); (iv) HVR-H1 comprising sequence D1-D10, wherein D1-D10 is GFFITNNYWG (SEQ ID NO: 4); (v) HVR-H2 comprising sequence E1-E17, wherein E1-E17 is GYISYSGSTSYNPSLKS (SEQ ID NO: 5), or a variant thereof, wherein said variant comprises 1-7 (1, 2, 3, 4, 5, 6, or 7) substitutions in SEQ ID NO: 5 in any combination of the following positions: E2 (Y, V, D, or F), E6 (S or G), E10 (S or Y), E12 (N, A, D, or T), E13 (P, D, A, or H), E15 (L or V), E17 (S or G); and (vi) HVR-H3 comprising sequence F1-F11, wherein F1-F11 is MTGSSGYFDF (SEQ ID NO: 6), or a variant thereof, wherein said variant comprises at 1 or 2 substitutions in SEQ ID NO: 6 in any combination of the following positions: F2 (R, M, A, E, G, Q, R, or S), and F11 (F or Y); or (b)(i) HVR-L1 comprises a sequence selected from the group consisting of SEQ ID NO:1, SEQ ID NO: 7, SEQ ID NO: 8, and SEQ ID NO:9, (ii) HVR-L2 comprises a sequence selected from the group consisting of SEQ ID NO:2, SEQ ID NO: 67, and SEQ ID NO: 68, (iii) HVR-L3 comprises SEQ ID NO:3, (iv) HVR-H1 comprises SEQ ID NO:4, (v) HVR-H2 comprises SEQ ID NO:5, and (vi) HVR-H3 comprises SEQ ID NO:6 or 66 for relative positions F2-F11 or comprises SEQ ID NO:63 or 64 or 65 for relative positions F1-F11, wherein said humanized antibody binds integrin beta 7.

2. The method of claim 1, wherein the second integrin subunit is alpha4 integrin subunit, and wherein the ligand is MAdCAM, VCAM or fibronectin.

3. The method of claim 2, wherein the alpha4 integrin subunit is from human.

4. The method of claim 3, wherein the ligand is from human.

5. The method of claim 1, wherein the second integrin subunit is alphaE integrin subunit, and wherein the ligand is E-cadherin.

6. The method of claim 5, wherein the alphaE integrin subunit is from human.

7. The method of claim 6, wherein the ligand is from human.

8. The method of claim 1, wherein the inhibiting reduces or alleviates symptoms of a disorder selected from the group consisting of inflammation, asthma, inflammatory bowel disease, Crohn's disease, ulcerative colitis, diabetes, inflammation resulting of organ transplantation, graft versus host disorder, and inflammation associated with allograft disorders.

9. The method of claim 1, wherein said method modulates beta7 integrin-mediated cellular adhesion and/or recruitment in a mammal experiencing a disorder.

10. The method of claim 9, wherein the disorder is selected from the group consisting of inflammation, asthma, inflammatory bowel disease, Crohn's disease, ulcerative colitis, diabetes, inflammation resulting of organ transplantation, graft versus host disorder, and inflammation associated with allograft disorders.

11. The method of claim 9, wherein the mammal is a human.

12. The method of claim 9, wherein the modulating inhibits interaction of beta7 integrin with alpha4 integrin, alphaE integrin, MAdCam, VCAM, E-cadherin, and/or fibronectin.

13. The method of claim 9, wherein the contacting comprises administering to the mammal an effective amount of a composition comprising the humanized anti-integrin beta 7 antibody and a pharmaceutical carrier.

14. The method of claim 13, further comprising administering a second biopharmaceutical agent or chemotherapeutic agent.

* * * * *

UNITED STATES PATENT AND TRADEMARK OFFICE
CERTIFICATE OF CORRECTION

| | | |
|---|---|---|
| PATENT NO. | : 8,124,082 B2 | Page 1 of 1 |
| APPLICATION NO. | : 12/390730 | |
| DATED | : February 28, 2012 | |
| INVENTOR(S) | : Fong et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 125 days.

Signed and Sealed this
Twenty-sixth Day of June, 2012

David J. Kappos
*Director of the United States Patent and Trademark Office*